US012577726B2

(12) United States Patent
Subramaniam et al.

(10) Patent No.: US 12,577,726 B2
(45) Date of Patent: Mar. 17, 2026

(54) VESICLE-COATED FIBERS AND METHODS OF MAKING AND USING

(71) Applicant: The Regents of the University of California, Oakland, CA (US)

(72) Inventors: Anand Bala Subramaniam, Merced, CA (US); Joseph Pazzi, Merced, CA (US); Vaishnavi Girish, Merced, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1156 days.

(21) Appl. No.: 17/293,905

(22) PCT Filed: Nov. 14, 2019

(86) PCT No.: PCT/US2019/061569

§ 371 (c)(1),
(2) Date: May 13, 2021

(87) PCT Pub. No.: WO2020/102605

PCT Pub. Date: May 22, 2020

(65) Prior Publication Data

US 2022/0018060 A1 Jan. 20, 2022

Related U.S. Application Data

(60) Provisional application No. 62/834,279, filed on Apr. 15, 2019, provisional application No. 62/767,990, filed on Nov. 15, 2018.

(51) Int. Cl.

| | |
|---|---|
| ***D06M 23/02*** | (2006.01) |
| ***A61K 9/1272*** | (2025.01) |
| ***A61K 9/1273*** | (2025.01) |
| ***A61K 9/1277*** | (2025.01) |
| ***D06M 13/203*** | (2006.01) |
| ***D06M 15/647*** | (2006.01) |
| ***D21H 19/82*** | (2006.01) |

(52) U.S. Cl.

CPC ........... *D06M 23/02* (2013.01); *A61K 9/1272* (2013.01); *A61K 9/1273* (2013.01); *A61K 9/1277* (2013.01); *D06M 13/203* (2013.01); *D06M 15/647* (2013.01); *D21H 19/82* (2013.01)

(58) Field of Classification Search

CPC .. D06M 23/02; D06M 13/203; D06M 15/647; D21H 19/82; A61K 9/1272; A61K 9/1273; A61K 9/1277

USPC .......................................................... 8/115.6

See application file for complete search history.

(56) References Cited

U.S. PATENT DOCUMENTS

| | | | | |
|---|---|---|---|---|
| 5,173,219 A * | 12/1992 | Kim | A61K 9/1277 436/829 |
| 8,680,237 B2 | 3/2014 | Strome et al. | |
| 2004/0034336 A1 * | 2/2004 | Scott | A61K 31/727 514/17.4 |
| 2005/0010161 A1 | 1/2005 | Sun et al. | |
| 2008/0241200 A1 | 10/2008 | Sojka | |
| 2016/0000886 A1 | 1/2016 | Parker et al. | |
| 2016/0243171 A1 | 8/2016 | Shiels et al. | |

FOREIGN PATENT DOCUMENTS

| | | | |
|---|---|---|---|
| CN | 1980637 | * | 6/2007 |
| CN | 107427791 | * | 12/2011 |
| CZ | 2006192 | * | 10/2007 |
| WO | 9300888 | A1 | 1/1993 |
| WO | 2011095353 | A1 | 8/2011 |
| WO | 2017158302 | A1 | 9/2017 |

OTHER PUBLICATIONS

Li et al. Cellulose Abetted Assembly and Temporally Decoupled Loading of Cargo into Vesicles Synthesized from Functionally Diverse Lamellar Phase Forming Amphiphiles. Biomacromolecules, 2018, 19, 849-859.*

Kresse KM, Xu M, Pazzi J, García-Ojeda M, Subramaniam AB. Novel Application of Cellulose Paper as a Platform for the Macromolecular Self-Assembly of Biomimetic Giant Liposomes. ACS Appl Mater Interfaces. Nov. 30, 2016;8(47):32102-32107. doi: 10.1021/acsami.6b11960. Epub Nov. 15, 2016. PMID: 27933839.*

Kundu, Self-Assembly of Amphiphiles into Vesicles and Fibrils: Investigation of Structure and Dynamics Using Spectroscopy and Microscopy Techniques. Langmuir Mar. 15, 2018, 34, 39, 11637-11654.*

Akashi, K.; Miyata, H.; Itoh, H.; Kinosita, K., "Preparation of giant liposomes in physiological conditions and their characterization under an optical microscope", Biophys. J. 1996, 71, 3242-3250.

Angelova, M. I.; Dimitrov, D. S., "Liposome electroformation." Faraday Discuss. Chem. Soc. 1986, 81, 303-311.

Bagatolli, L. A.; Parasassi, T.; Gratton, E., "Giant phospholipid vesicles: Comparison among the whole lipid sample characteristics using different preparation methods—A two photon fluorescence microscopy study", Chem. Phys. Lipids 2000, 105, 135-147.

Blain, J. C.; Szostak, J. W., "Progress Toward Synthetic Cells", Annu. Rev. Biochem. 2014, 83, 615-640.

Dietrich, C.; Volovyk, Z. N.; Levi, M.; Thompson, N. L.; Jacobson, K., "Partitioning of Thy-1, GM1, and cross-linked phospholipid analogs into lipid rafts reconstituted in supported model membrane monolayers", Proc. Natl. Acad. Sci. U. S. A. 2001, 98, 10642-10647.

Dimova, R.; Aranda, S.; Bezlyepkina, N.; Nikolov, V.; Riske, K. A; Lipowsky, R., "A practical guide to giant vesicles. Probing the membrane nanoregime via optical microscopy", J. Phys. Condens. Matter 2006, 18, S1151-S1176.

(Continued)

*Primary Examiner* — Amina S Khan

(74) *Attorney, Agent, or Firm* — Platinum Intellectual Property PC

(57) ABSTRACT

Methods and compositions for rapid and efficient assembly of fibers coated with lamellar vesicles are provided. Cosmetic and therapeutic uses of vesicle-coated fibers are also provided.

5 Claims, 29 Drawing Sheets

(56) References Cited

OTHER PUBLICATIONS

Dominak, L. M.; Omiatek, D. M.; Gundermann, E. L.; Heien, M. L.; Keating, C. D., "Polymeric crowding agents improve passive biomacromolecule encapsulation in lipid vesicles", Langmuir 2010, 26, 13195-13200.
Estes, D. J.; Mayer, M., "Giant liposomes in physiological buffer using electroformation in a flow chamber", Biochim. Biophys. Acta—Biomembr. 2005, 1712, 152-160.
Girish, V.; Pazzi, J.; Li, A.; Subramaniam, A. B. "Fabrics of Diverse Chemistries Promote the Formation of Giant Vesicles from Phospholipids and Amphiphilic Block Copolymers", Langmuir 2019, 35, 9264-9273.
Has, C.; Sunthar, P. A, "Comprehensive Review on Recent Preparation Techniques of Liposomes", J. Liposome Res. 2019, 30, 336-365.
Horger, K. S.; Estes, D. J.; Capone, R.; Mayer, M., "Films of agarose enable rapid formation of giant liposomes in solutions of physiologic ionic strength", J. Am. Chem. Soc. 2009, 131, 1810-1819.
Kresse, K. M.; Xu, M.; Pazzi, J.; Garcia-Ojeda, M.; Subramaniam, A. B., "Novel Application of Cellulose Paper as a Platform for the Macromolecular Self-Assembly of Biomimetic Giant Liposomes", ACS Appl. Mater. Interfaces 2016, 8, 32102-32107.
Kubsch, B.; Robinson, T.; Steinkühler, J.; Dimova, R., "Phase behavior of charged vesicles under symmetric and asymmetric solution conditions monitored with fluorescence Microscopy", J. Vis. Exp. 2017, No. 128, 1-17.
Lopez, Mora, N.; Hansen, J. S.; Gao, Y.; Ronald, A. A.; Kieltyka, R.; Malmstadt, N.; Kros, A., "Preparation of size tunable giant vesicles from cross-linked dextran(ethylene glycol) hydrogels", Chem. Commun. 2014, 50, 1953-1955.
Movsesian, N.; Tittensor, M.; Dianat, G.; Gupta, M.; Malmstadt, N., "Giant lipid vesicle formation using vapor-deposited charged porous polymers", Langmuir 2018, 34, 9025-9035.
Mulla, Y.; Aufderhorst-Roberts, A.; Koenderink, G. H. "Shaping up synthetic cells", Phys. Biol. 2018, 15.
Needham, D.; Evans, E., "Structure and mechanical properties of giant lipid (DMPC) vesicle bilayers from 20 C below to 10 C above the liquid crystal-crystalline phase transition at 24 C", Biochemistry 1988, 27, 8261-8269.
Pazzi, J. Subramaniam, A.B, "Nanoscale curvature promotes high-yield spontaneous formation of cell-mimetic giant vesicles on nanocellulose paper", ACS Applied Materials & Interfaces 12 (50), 56549-56561 (2020).
Peruzzi, J.; Gutierrez, M. G.; Mansfield, K.; Malmstadt, N., "Dynamics of hydrogel-assisted giant unilamellar vesicle formation from unsaturated lipid systems", Langmuir 2016, 32, 12702-12709.
Peterlin, P.; Arrigler, V., "Electroformation in a flow chamber with solution exchange as a means of preparation of flaccid giant vesicles", Colloids Surfaces B Biointerfaces 2008, 64, 77-87.
Reeves, J. P.; Dowben, R. M., "Formation and properties of thin-walled phospholipid vesicles", J. Cell. Physiol. 1969, 73, 49-60.
Roodbeen, R.; Van Hest J.C.M. "Synthetic cells and organelles: compartmentalization strategies", BioEssays, 2009, 1299-1308.
Schmitt, C.; Lippert, A. H.; Bonakdar, N.; Sandoghdar, V.; Voll, L. M., "Compartmentalization and Transport in Synthetic Vesicles". Front. Bioeng. Biotechnol. 2016, 4, 1-12.
Steer, D.; Leung, S. S. W.; Meiselman, H.; Topgaard, D.; Leal, C., "Structure of lungmimetic multilamellar bodies with lipid compositions relevant in pneumonia", Langmuir 2018, 34, 7561-7574.
Tsai, F. C.; Stuhrmann, B.; Koenderink, G. H., "Encapsulation of active cytoskeletal protein networks in cell-sized liposomes", Langmuir 2011, 27, 10061-10071.
Veatch, S. L.; Keller, S. L., "Separation of liquid phases in giant vesicles of ternary mixtures of phospholipids and cholesterol", Biophys. J. 2003, 85, 3074-3083.
Walde, P., "Building artificial cells and protocell models: Experimental approaches with lipid vesicles", BioEssays. 2010, 296-303.
Walde, P.; Cosentino, K.; Engel, H.; Stano, P., "Giant Vesicles: Preparations and Applications", ChemBioChem. 2010, 848-865.
Weinberger, A.; Tsai, F. C.; Koenderink, G. H.; Schmidt, T. F.; Itri, R.; Meier, W.; Schmatko, T.; Schröder, A.; Marques, C., Gel-assisted formation of giant unilamellar vesicles, Biophys. J. 2013, 105, 154-164.
Xu, C.; Hu, S.; Chen, X., "Artificial cells: from basic science to applications", Mater Today 2016, 19, 516-532.
York-Duran, M. J.; Godoy-Gallardo, M.; Labay, C.; Urquhart, A. J.; Andresen, T. L.; Hosta-Rigau, L., "Recent advances in compartmentalized synthetic architectures as drug carriers, cell mimics and artificial organelles", Colloids Surfaces B Biointerfaces 2017, 152, 199-213.
Chakrabarty, A. et al., "Recent Advances in Nanocellulose Composites with Polymers: A Guide for Choosing Partners and How to Incorporate Them", Polymers, www/mdpi.com/journal/polymers, May 10, 2018, vol. 10, Issue 517, pp. 1-47.
Dominak, L.M. et al., "Polymer Encapsulation within Giant Lipid Vesicles", Langmuir, Department of Chemistry, Pennsylvania State University, . May 22, 2007, vol. 23, pp. 7148-7154.
GE, "Grade 42—Quantitative Filter", Typical data, gelifesciences.com/Whatman, 2019; [retrieved Jan. 9, 2020), 2 pages, Retrieved from the 6,8 Internet; first table.
Gupta, S. et al., "An improvised one-step sucrose cushion ultracentrifugation method for exosome isolation from culture supernatants of mesenchymal stem cells", Stem Cell Research & Therapy, India Institute of Medical Sciences, BMC, Jul. 4, 2018, vol. 9, Issue 180, https://doi.org/10.1186/s13287-018-0923-0, pp. 1-11.
Li, A. et al., "Cellulose Abetted Assembly and Temporally Decoupled Loading of Cargo into Vesicles Synthesized from Functionally Diverse Lamellar Phase Forming Amphiphiles", Biomacromolecules, pubs.acs.org/Biomac, Dept of Bioengineering, Univ of CA, Feb. 2018, vol. 19, pp. 849-859.
Mora, N.L. et al., "Evaluation of dextran (ethylene glycol) hydrogel films for giant unilamellar lipid vesicle production and their application for the encapsulation of polymersomes", HHS Public Access Author manuscript, Soft Matter, doi:10.1039/c7sm00551b, Aug. 23, 2017, vol. 13, No. 33, pp. 5580-5588, 21 total pages.
PCT/US19/61569, M1-PCT, International Search Report & Written Opinion (ISR/WO), Apr. 9, 2020, 17 pps.

* cited by examiner $CH_3(CH_2)_7CH{=}CH(CH_2)_7COOH$

MW = 282.46

$PBD_{46}PEO_{30}$ $M_n \sim 3900$

Pluronic L121, $PEO_5PPO_{67}PEO_5$ $M_n$ ~ 4400

First cycle

Fifth cycle

VESICLE-COATED FIBERS AND METHODS OF MAKING AND USING

CROSS REFERENCE TO RELATED APPLICATIONS

This application claims the benefit of U.S. provisional patent application No. 62/767,990 (filed Nov. 15, 2018) and of U.S. provisional patent application No. 62/834,279 (filed Apr. 15, 2019); the entire disclosures of both of which are hereby incorporated by reference herein for all purposes.

STATEMENT REGARDING FEDERAL SUPPORT

Certain of the work described herein was conducted with federal support under contracts NSF-DMR-1848573, NSF CBET-1512686 and NSF-HRD-1547848. The United States Government may have certain rights in the inventions described herein. Equipment used in some of the experiments described herein was provided through NSF MRI Award No. DMR-1625733 and NASA Grant NNX1SAQ01A.

FIELD

This disclosure is in the field of biological vesicles and vesicle-coated fibers.

BACKGROUND

Chemical compounds (e.g., commercially important compounds such as drugs, cosmetics, and fragrances) can be categorized, among other ways, based on their relative hydrophilicity or hydrophobicity. Hydrophilic substances generally posses some degree of polarity and are therefore soluble in polar solvents such as water, certain alcohols and aqueous solutions. Hydrophilic substances are generally nonpolar and are therefore soluble in nonpolar solvents such as oils, chloroform, isopropanol and methanol.

Dispersal of hydrophilic materials in aqueous solution occurs relatively simply, by dissolution and diffusion to equilibrium, and can be enhanced by fluid convection. However, controlling the rates of dispersal or dissolution (i.e., establishing a uniform release rate for a drug) can present challenges. In such cases, control of release rate can often be achieved by encapsulation (e.g., in a vesicle in which the hydrophilic solute is bounded by a lipid membrane), allowing release of the solute to be triggered at specific time points.

Hydrophobic materials, on the other hand, do not disperse spontaneously in aqueous solution. Rather, the use of hydrophobic or amphiphilic dispersal agents is required to promote dispersal of hydrophobic materials in aqueous solutions.

Various types of vesicles, containing a hydrophilic core (lumen) surrounded by a hydrophobic membrane (lamella); have found use for storing and/or dispensing both hydrophilic or hydrophobic substances, or both. Hydrophilic substances can be dispersed in the hydrophilic core of a vesicle; and hydrophobic substances can be placed in the membrane.

Giant unilamellar vesicles (GUVs) are closed phospholipid bilayer membranes (i.e., composed of a single bilayer) with diameters greater than one micrometer[1], thus mimicking the dimensions and compartmentalization properties of biological cellular membranes. GUVs are useful in vitro models for biophysical experiments[1-5], for biomimetic drug delivery, and for designing synthetic cells[6-12]. Lamellar stacks of phospholipids on solid surfaces such as glass or roughened Teflon spontaneously vesiculate over the course of 24-36 hours in aqueous solutions to form giant vesicles in a method known as gentle hydration[13-17]. Vesiculation can also be achieved by applying oscillating electric fields orthogonal to the lamellar phospholipid stacks in a low ionic strength environment, in a process known as electroformation[18]; and by hydrating lamellar phospholipid stacks on hydrogel surfaces (such as agar, dextran and polyvinyl alcohol) in a process known as gel-assisted hydration[19-24]. In microfluidic methods, lipids dispersed in a non-polar solvent form a double emulsion, an aqueous phase inside and an aqueous phase outside, that sandwiches a thin circular layer of the non-polar solvent using a microfluidic co-flow device. As the solvent evaporates, the lipids self-assemble to form a bilayer membrane with residual solvent left in the membrane. Dissolved solutes ("cargo") in the aqueous solution, such as small molecules, proteins, and polysaccharides can be encapsulated in the growing GUVs[27-31].

There are disadvantages associated with each of the foregoing procedures for assembling GUVs. Gentle hydration is slow (24-48 hours), must be conducted on surfaces of glass or Teflon, is restricted to the use of negatively-charged lipids, and is sensitive to movement or flow during the assembly process.

Electroformation requires the use of conductive electrodes (such as indium tin oxide-coated slides, stainless steel or platinum wires), requires a source of electrical power, and does not work efficiently with charged lipids.

For gel-assisted hydration, the dissolution rate is temperature-sensitive, which requires vesicle assembly to be conducted at low temperatures. In addition, because hydrogels are soluble in water, the time in which they can remain in contact with an aqueous solution is limited, thereby also limiting the duration of time in which vesicle assembly can be conducted. Although hydrogels can be crosslinked to reduce their solubility in aqueous solution, this increases their chemical complexity.

Although microfluidic methods provide precise control of vesicle size, and are amenable to use with many different types of lipids, they are difficult to scale up (for manufacturing purposes) and leave behind large amounts of solvent in the membranes, raising issues of potential toxicity.

Thus, existing methods for vesicle assembly suffer from the disadvantages of cost, time, toxicity, power requirements, and difficulty in scale-up. Accordingly, there is a need for new methods of vesicle assembly that are inexpensive, non-toxic, do not require a power source and are easily scalable.

SUMMARY

The present disclosure provides new methods for assembling vesicles on solid surfaces (e.g., fibers), wherein the vesicles comprise membranes of lamellar phase amphiphiles of various sizes. Also provided are new compositions of matter comprising a composite of dried amphiphilic molecules that form lamellar phases that coat the surfaces of cylindrical fibers and woven material composed of cylindrical fibers. The size of the fibers can range from nanometers in diameter to hundreds of micrometers in diameter. The fiber material can be a natural material such as, for example, cotton, silk, or wool; a synthetic material such as, for example, nylon, polyester or fiberglass, or a regenerated fiber such as rayon. Nanofibers, such as tracing paper, nanocellulose paper or regenerated cellulose membranes, can also be used. In addition to fibrous materials, vesicles can also be produced on metal meshes, such as, for example, stainless steel (e.g., steel wool) or copper.

The amphiphilic molecule can be any pure amphiphile, or mixture of amphiphiles, that forms a lamellar phase. A wide variety of chemically distinct molecules such as, for example, phospholipids, sphingolipids, fatty acids, fatty alcohols and amphiphilic block copolymers; are capable of forming lamellar phases. Amphiphiles with a hydrophilic/lipophilic balance (HLB) ratio of about 10 (where the HLB ratio=$20M_h/M$, and where $M_h$ is the molecular mass of the hydrophilic portion of the molecule, and M is the molecular mass of the whole molecule, giving a result on the scale of 0 to 20), or with a packing parameter ~1, assemble into vesicles when present above their critical aggregation concentration (CAC). Packing parameter is calculated as $v/a_o l_c$; in which v is the volume of the hydrophobic group, $l_c$ is the critical length of the hydrophobic group, and $a_o$ is the preferred area of the hydrophobic group. The CAC value is unique for each molecule, and can be measured by measuring changes in dynamic light scattering as a function of molecule concentration. Scattering increases dramatically when concentration that causes aggregation is reached. CAC values can also be measured by measuring the surface tension of the aqueous solution as a function of amphiphile concentration. Surface tension decreases until the CAC is reached, after which surface tension saturates. CAC values are available in the literature.

In the amphiphilic lamellar phase-coated fibers disclosed herein, the amphiphile-fiber composite material spontaneously produces vesicles upon contact with an aqueous solution. Depending on the ratio of amphiphile mass to substrate surface area, the vesicles produced can be unilamellar or multilamellar.

The vesicles can remain attached to the fibers or can be released from the fibers. Under conditions in which there are no external shear forces or fluid flow across the coated fiber, many of the vesicles remain attached to the fiber. When flow occurs due to external forces, such as wicking of the fluid in the porous fabric, movement of the fabric in the solution, or the actions of a pipette on the fluid, vesicles that were attached to the fibers are released into solution and travel with the flowing fluid.

Also provided are new methods for forming vesicles that are composed of membranes of lamellar phase amphiphiles of various sizes. The methods comprise coating the surfaces of fibers (e.g., cylindrical fibers) or nanofibers with amphiphilic molecules, drying the molecules onto the fiber and incubating the dried fiber in an aqueous "growth buffer." In certain embodiments, the fibers are coated with other compounds (either water-soluble or water-insoluble) prior to application of one or more amphiphilic molecules. In contrast to previous methods, in which compounds are applied to fabrics, the present disclosure provides methods in which vesicles containing compounds are applied to fabrics (see below). In this way, both hydrophilic compounds (e.g., water-soluble molecules) and hydrophobic compounds (e.g., water-insoluble molecules) can be applied to fabrics in the form of compound-containing vesicles, in which hydrophilic compounds are located in the vesicle lumen and hydrophobic compounds are located in the vesicle membrane.

Coating of the fiber with an amphiphile is achieved by dispersing the amphiphile in a solvent (e.g., a volatile solvent, e.g., chloroform, toluene, benzene, ethanol, isopropanol or water); then drying the solvent (or allowing the solvent to dry). Additional compounds (both water-soluble and water-insoluble) can also be co-dispersed in the solvent with the amphiphile and will also coat the fiber along with the lipids. The lamellarity of the vesicles obtained from this process can be controlled by the mass of amphiphile deposited on the fiber, with higher mass being correlated with formation of multiple (e.g., nested) membranes.

Methods for release of vesicles from a vesicle-coated substrate are also provided. For vesicle-coated substrates made by the methods disclosed herein, simple movement in or through an aqueous solution, or passage of an aqueous solution across the vesicle-coated substrate, or wicking of an aqueous solution through the substrate will cause release of vesicles from the substrate. Basically any process that causes flow (e.g., thermal gradient, surface tension gradient, pressure gradient, shear stress gradient (due to movement, for example) or bacterial motion adjacent to the substrate) can release vesicles from the substrate. Optionally, released vesicles can be harvested from solution and used for various application as described elsewhere herein.

The present disclosure also provides therapeutic and cosmetic compositions utilizing vesicle-coated-fibers as disclosed herein. The present disclosure also provides therapeutic and cosmetic methods utilizing the therapeutic and cosmetic compositions disclosed herein.

Accordingly, in certain embodiments, provided herein is a method for making a vesicle-coated substrate (e.g., fiber), the method comprising (a) dispersing an amphiphilic molecule in a volatile solvent; (b) contacting the dispersed amphiphilic molecule of (a) with a fiber; (c) removing the solvent; and (d) incubating the amphiphile-coated fiber in a first aqueous solution.

Removal of solvent, in step (c) can be by evaporation, either unassisted or using a vacuum chamber.

The amphiphilic molecule can be a phospholipid, a sphingolipid, a fatty acid, a ceramide, a fatty alcohol, a diblock polymer or a triblock polymer.

In certain embodiments, the solvent can be chloroform, methanol, ethanol, isopropanol, or water.

In certain embodiments, the substrate has at least one element having a principal radius of curvature that is not zero. The non-zero radius of curvature can be either positive or negative In certain embodiments, the substrate is a fiber. In additional embodiments, the fiber is a naturally-occurring fiber such as, for example cellulose, silk or wool. In embodiments in which the fiber is cellulose, the cellulose can be cotton, hemp, jute, papyrus, paper or wood pulp.

In certain embodiments, the fiber is a semi-synthetic fiber such as, for example, rayon.

In certain embodiments, the fiber is a synthetic fiber such as, for example, nylon or polyester.

In certain embodiments, the fiber is a synthetic inorganic fiber such as, for example, fiberglass.

In certain embodiments, the fiber is a nanofiber such as, for example, tracing paper, nanocellulose paper, or regenerated cellulose membrane. In further embodiments, nanocellulose paper is made by solution casting of nanocellulose pulp. Nanohybrid papers, containing different concentrations of nanocellulose (i.e., lower than are present in pure nanocellulose, but more than are present in raw cellulose) can also be used as substrates.

In further embodiments, the fiber is a metal mesh, such as stainless steel (e.g., steel wool) or copper.

In certain embodiments, methods for vesicle assembly further comprise introducing a compound into the first aqueous solution (e.g., water or buffer). Upon contact of the amphiphile-coated substrate with the compound-containing first aqueous solution, the compound is sequestered in the aqueous lumen of the vesicles so formed, thereby generating vesicles containing the compound as cargo.

In certain additional embodiments, a second molecule is dispersed in the volatile solvent, along with the amphiphile. Upon formation of vesicles, the second molecule is sequestered in the hydrophobic core of the amphiphilic membrane, thereby generating vesicles containing the second molecule as cargo.

In certain additional embodiments, the compound is deposited onto the substrate (e.g., fibers or nanofibers) before or after coating the fibers with amphiphiles. Upon contact of the amphiphile-coated substrate with an aqueous solution, the compound dissolves into the solution and is entrapped in the lumens of the vesicles so formed, thereby generating vesicles containing the compound as cargo.

Also provided are methods for producing a population of vesicles in a high ionic strength solution in which vesicle formation is initially conducted at low ionic strength, and then the ionic strength of the growth buffer is increased. In certain embodiments a low ionic strength solution contains less than 50 mM, less than 40 mM, less than 30 mM, less than 25 mM, less than 20 mM, less than 15 mM, less than 10 mM or less than 5 mM monovalent salt or its equivalent. In certain embodiments, a high ionic strength solution contains greater than 5 mM, greater than 10 mM, greater than 15 mM, greater than 20 mM, greater than 25 mM, greater than 30 mM, greater than 40 mM, greater than 50 mM, greater than 60 mM, greater than 70 mM, greater than 75 mM or greater than 100 mM monovalent salt or its equivalent. The monovalent salt can be a cation, an anion or both.

Additional methods for producing vesicles in a high-salt environment comprise coating the substrate, prior to vesicle formation, with a polymer. Exemplary polymers include hyaluronic acid, carboxymethylcellulose, Ficoll, dextran, nucleic acids (e.g., DNA, RNA), polypeptides and polysaccharides.

Also provided are methods for forming vesicles on a substrate, wherein the vesicles comprise a hydrophilic compound in the vesicle lumen, the method comprising (a) depositing a solution of the hydrophilic compound on the substrate; (b) allowing the solution to dry onto the substrate; (c) applying a lipid to the substrate; and (d) placing the lipid-coated substrate in an aqueous solution. In certain embodiments, the solution of the hydrophilic compound is an aqueous solution. In additional embodiments, the substrate is a cellulose nanopaper. In other embodiments, the substrate is tracing paper. In additional embodiments, the lipid is DOPC.

Also provided are vesicles made by a method comprising (a) dispersing an amphiphilic molecule in a volatile solvent; (b) contacting the dispersed amphiphilic molecule of (a) with a substrate (e.g., a fiber); (c) removing the solvent; and (d) incubating the amphiphile-coated substrate in a first aqueous solution. The vesicles can be unilamellar or multilamellar (e.g., bilamellar, trilamellar or oligolamellar).

The amphiphilic molecule can be a phospholipid, a sphingolipid, a fatty acid, a ceramide, a fatty alcohol, a diblock polymer or a triblock polymer.

In certain embodiments, the solvent can be chloroform, methanol. ethanol, isopropanol, or water.

In additional embodiments, the fiber is a naturally-occurring fiber such as, for example cellulose, silk or wool. In embodiments in which the fiber is cellulose, the cellulose can be cotton, hemp, jute, papyrus, paper or wood pulp.

In certain embodiments, the fiber is a synthetic fiber such as, for example, nylon, polyester or rayon.

In certain embodiments, the fiber is a nanofiber such as, for example, tracing paper, nanocellulose paper, or regenerated cellulose membrane.

In further embodiments, the fiber is a metal mesh, such as stainless steel (e.g., steel wool) or copper.

In certain embodiments, vesicles also comprise one or more compound(s) within the lumen of the vesicles. Such compounds can be, for example, a therapeutic molecule (e.g., a drug, anesthetic, antibiotic, analgesic) or one or more cosmetic molecules (e.g., anti-aging agents such as retinol, antiperspirants, fragrances).

In certain additional embodiments, vesicles also comprise one or more compound(s) within the membrane of the vesicles. Such compounds can be, for example, a therapeutic molecule (e.g., a drug, anesthetic, antibiotic, analgesic) or one or more cosmetic molecules (e.g., anti-aging agents such as retinol, antiperspirants, fragrances). Vesicles can also comprise structures such as nanoparticles, colloidal particles and viruses.

Also provided are methods of releasing vesicles from a vesicle-coated substrate, comprising fluid flow across or through the substrate.

Also provided are methods for making an amphiphile-coated substrate, the methods comprising: (a) dispersing an amphiphilic molecule in a volatile solvent; (b) contacting the dispersed amphiphilic molecule of (a) with the substrate; and (c) removing the solvent. Amphiphile-coated substrates made by the foregoing method are also provided.

Also provided are therapeutic compositions comprising vesicle-coated fibers as disclosed herein, wherein the vesicle-coated fibers further comprise one or more therapeutic molecules. The therapeutic molecule(s) can reside in the lumen of the vesicle and/or in the membrane of the vesicle and can be, for example, a drug, an anesthetic, an antibiotic, or an analgesic.

Also provided are cosmetic compositions comprising vesicle-coated fibers as disclosed herein, wherein the vesicle-coated fibers further comprise one or more cosmetic molecules. The cosmetic molecule(s) can reside in the lumen of the vesicle and/or in the membrane of the vesicle and can be, for example, an anti-aging agent such as retinol, an antiperspirant, or a fragrance.

Also provided are therapeutic methods utilizing the therapeutic compositions disclosed herein.

Also provided are cosmetic methods utilizing the cosmetic compositions disclosed herein.

In certain embodiments, methods for applying a therapeutic composition to a subject are provided, the methods comprising contacting the subject with a therapeutic composition as disclosed herein.

In certain embodiments, methods for applying a cosmetic composition to a subject are provided, the methods comprising contacting the subject with a cosmetic composition as disclosed herein.

Also provided are vesicle-coated substrates, as described herein, for use in making a medical device (e.g., a bandage, stent, suppository, or pessary).

Also provided are vesicle-coated substrates, as described herein, for use in making a cosmetic device (e.g., a bandage or an antiperspirant patch).

Methods for controlling vesiculation, after an amphiphile has been applied to, or deposited on, a substrate, are also provided. In certain embodiments, vesiculation is controlled by the osmolarity of the growth buffer. Accordingly, amphiphile-coated substrates are prepared by (a) dispersing an amphiphilic molecule in a volatile solvent; (b) contacting the dispersed amphiphilic molecule of (a) with the substrate; (c) removing the solvent; and (d) incubating the amphiphile-coated substrate in a first aqueous solution containing a dissolved osmolyte, wherein the osmolarity of the first solution prevents vesiculation. Vesiculation can them be induced by diluting the first solution such that the osmolarity of the first solution permits vesiculation; or by transferring the amphiphile-coated substrate to a solution having an osmolarity that permits vesiculation.

In certain embodiments, the osmolyte is Ficoll 400. Concentrations of Ficoll 400 that provide an osmotic pressure of greater than 1 kPa (e.g., 2 mM or greater) prevent vesiculation. Dilution of the solution such that the Ficoll concentration is reduced to 0.7 mM or less; or transferring the amphiphile-coated substrate to a solution having a Ficoll concentration of 0.7 mM or less allows vesiculation to occur.

Compositions comprising an amphiphile-coated substrate in a solution having an osmolarity that prevents vesiculation are also provided. Vesiculation can be induced in these compositions by diluting the solution to a lower osmolarity that permits vesiculation; or by transferring the amphiphile-coated substrate to a different solution having an osmolarity that permits vesiculation.

In additional embodiments, vesiculation is controlled by the temperature of the growth buffer. Accordingly, amphiphile-coated substrates are prepared by (a) dispersing an amphiphilic molecule in a volatile solvent; (b) contacting the dispersed amphiphilic molecule of (a) with the substrate; (c) removing the solvent; and (d) incubating the amphiphile-coated substrate in a first aqueous solution having a temperature that is less than the transition temperature of the amphiphile. Vesiculation can then be induce by increasing the temperature of the first solution to a temperature greater than the transition temperature of the amphiphile; or by transferring the amphiphile-coated fiber to an environment (e.g., a solution) having a temperature that is greater than the transition temperature of the amphiphile.

In certain embodiments, the amphiphile is 1,2-dipentadecanoyl-sn-glycero-3-phosphocholine and the temperature that is less than the transition temperature of the amphiphile, which prevents vesiculation, is a temperature of 35° C. or lower. Increasing the temperature of the solution to a temperature above 35° C., or transferring the amphiphile-coated substrate to an environment having a temperature that is greater than 35° C., induces vesiculation.

Compositions comprising an amphiphile-coated substrate in a solution having a temperature that prevents vesiculation (i.e., a temperature below the transition temperature of the amphiphile) are also provided. Vesiculation can be induced in these compositions by warming the solution to a temperature that is above the transition temperature of the amphiphile, or by transferring the amphiphile-coated fiber to an environment (e.g., a solution) having a temperature that is greater than the transition temperature of the amphiphile.

BRIEF DESCRIPTION OF THE DRAWINGS

FIG. 10*a* shows silk; FIG. 10*b* shows wool; FIG. 10*c* shows rayon;

FIG. 10*d* shows polyester; FIG. 10*e* shows nylon; FIG. 10*f* shows fiberglass. The scale bar at the bottom right of each photograph represents 100 μM.

FIG. 11*a* shows silk; FIG. 11*b* shows wool; FIG. 11*c* shows rayon; FIG. 11*d* shows polyester; Figure lie shows nylon; FIG. 11*f* shows fiberglass. GUVS are seen as bright circles with dark interiors. Although not fluorescently labeled, the fibers are visible due to the fluorescent lipid coating. The scale bar at the bottom right of each photograph represents 25 μM.

FIG. 12*a* shows nylon; FIG. 12*b* shows polyester; FIG. 12*c* shows fiberglass. White arrows show multilamellar (non-GUV) vesicles formed in the gaps between the fibers in regions corresponding to lipid deposits. The scale bar at the bottom right of each photograph represents 25 μM.

FIG. 13*a* shows GUVs formed on silk; FIG. 13*b* shows GUVs formed on wool; FIG. 13*c* shows GUVs formed on rayon; FIG. 13*d* shows GUVs formed on polyester; FIG. 13*e* shows GUVs formed on nylon; FIG. 13*f* shows GUVs formed on fiberglass. The scale bar at the bottom right of each photograph represents 25 μM.

FIG. 16*a* shows diameters of GUVs harvested from rayon. FIG. 16*b* shows diameters of GUVs harvested from cotton. FIG. 16*c* shows diameters of GUVs harvested from nylon. FIG. 16*d* shows diameters of GUVs harvested from polyester. FIG. 16*e* shows diameters of GUVs harvested from fiberglass. FIG.

16*f* shows diameters of GUVs harvested from wool. Bin widths are 1 μm. Sample size (n) is listed in the upper right corner of each histogram.

Figure 17:
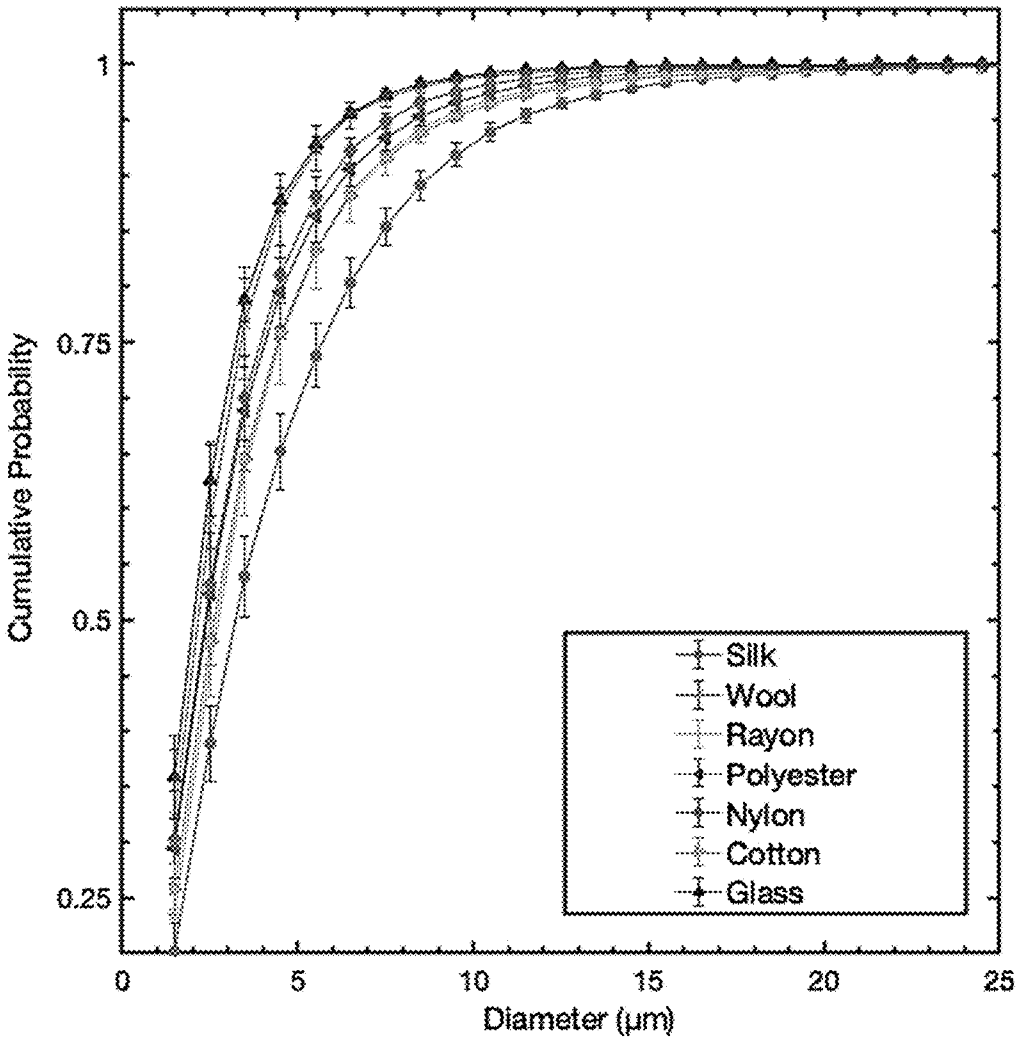

FIG. 17 shows cumulative distribution functions of populations of GUVs from silk, wool, rayon, polyester, nylon, cotton and fiberglass (glass). The points are the average cumulative probability from three experiments. The error bars are the standard deviation from the mean. The continuous lines are guides to the eye.

Figure 18:
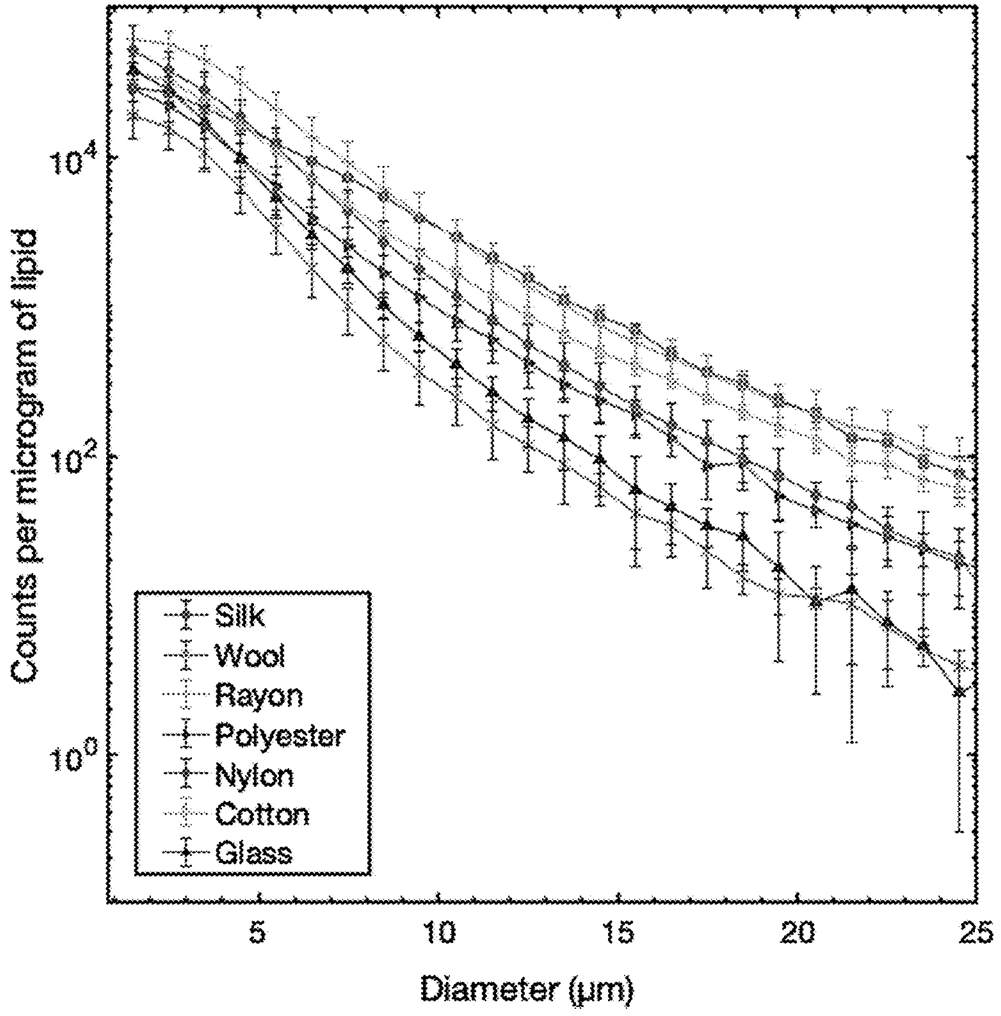

FIG. 18 shows vesicle counts, per microgram of lipid, for sizes of GUVs formed on different fabrics, as indicated in the bottom left corner of the graph. Each data point is an average value from three experiments. The error bars are the standard deviation from the mean. The continuous lines are guides to the eye.

Figure 19:
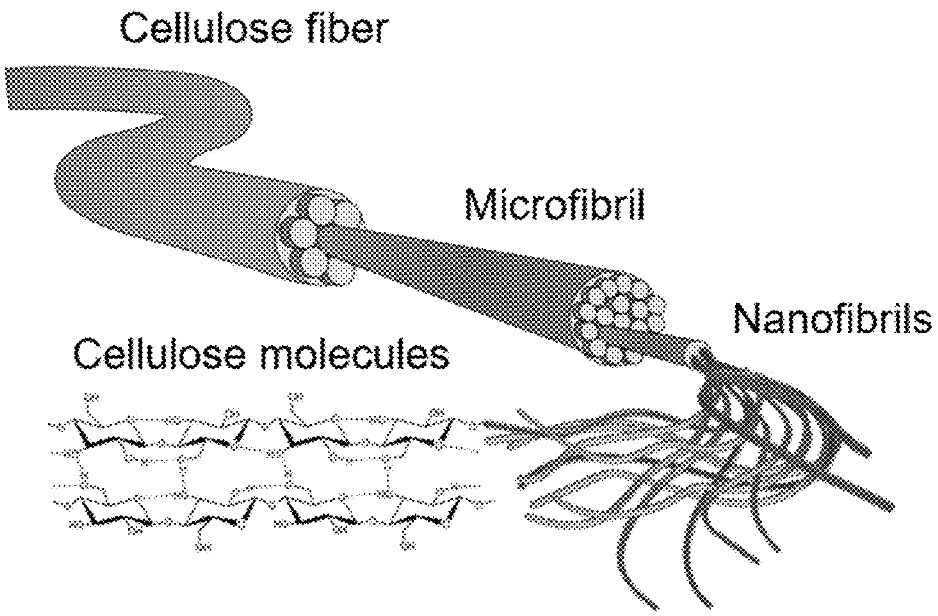

FIG. 19 provides a schematic diagram of the hierarchical structure of cellulose fibers, which are made up of microfibrils, which are in turn made up of nanofibrils comprising repeating cellulose molecules.

FIGS. 20A-20I show scanning electron micrographs of cellulose filter paper, nanocellulose paper and tracing paper.

Figure 20:
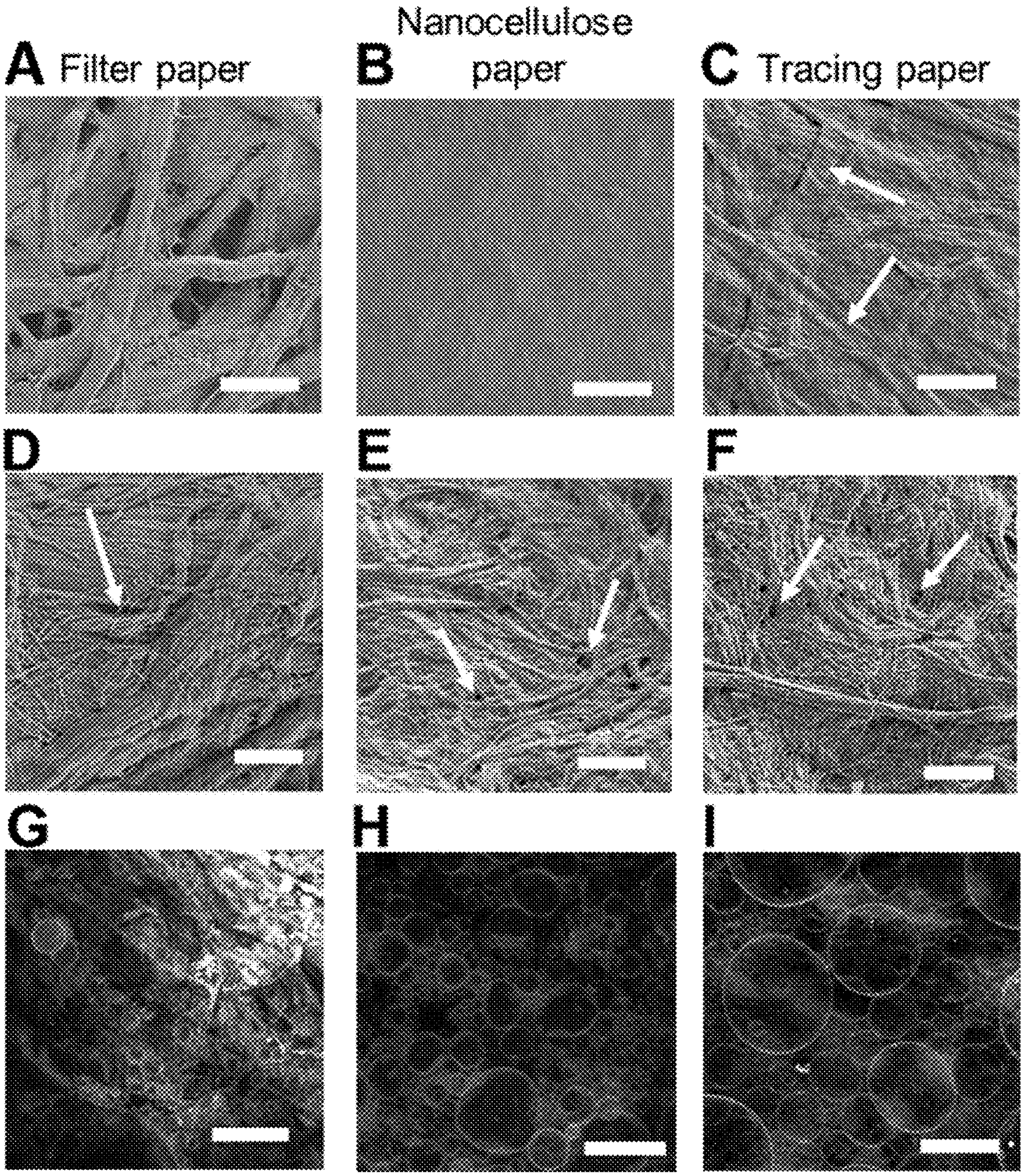

FIG. 20A shows a scanning electron micrograph at low power (field of view 300 μm×300 μm, captured pixel size 0.67 μm) of cellulose filter paper (Whatman G42).

FIG. 20B shows a scanning electron micrograph at low power (field of view 300 μm×300 μm, captured pixel size 0.67 μm) of nanocellulose paper, prepared as described in example 20.

FIG. 20C shows a scanning electron micrograph at low power (field of view 300 μm×300 μm, captured pixel size 0.67 μm) of commercially-obtained tracing paper. Arrows indicate surface cellulose fibers.

FIG. 20D shows a scanning electron micrograph at high power (field of view 10 μm×10 μm, captured pixel size 21 nm) of cellulose filter paper (Whatman G42). Arrows indicate pores between nanocellulose fibrils.

FIG. 20E shows a scanning electron micrograph at high power (field of view 10 μm×10 μm, captured pixel size 21 nm) of nanocellulose paper, prepared as described in Example 20. Arrows indicate pores between nanocellulose fibrils.

FIG. 20F shows a scanning electron micrograph at high power (field of view 10 μm×10 μm, captured pixel size 21 nm) of commercially-obtained tracing paper. Arrows indicate pores between nanocellulose fibrils.

FIG. 20G shows a confocal image at low power (field of view 300 μm×300 μm, captured pixel size 0.67 μm) of vesicles on cellulose filter paper (Whatman G42).

FIG. 20H shows a confocal image at low power (field of view 300 μm×300 μm, captured pixel size 0.67 μm) of vesicles on nanocellulose paper, prepared as described in Example 20.

FIG. 20I shows a confocal image at low power (field of view 300 μm×300 μm, captured pixel size 0.67 μm) of vesicles on commercially-obtained tracing paper.

FIGS. 21A-21F show examples of vesicles formed on tracing paper.

FIG. 21A shows a confocal image of vesicles assembled from the negatively-charged lipid DOPG on tracing paper. Scale bar is 50 μm.

FIG. 21B shows a confocal image of vesicles assembled from a 50:50 mol percent mixture of the negatively-charged lipids DOPS and DOPC on tracing paper. Scale bar is 50 μm.

FIG. 21C shows a confocal image of vesicles assembled from a mixture of DOPC, DPPC and cholesterol (36:36:28 mol percent, respectively) on tracing paper at 65° C. then cooled to room temperature. Scale bar is 50 μm.

FIG. 21D shows a confocal image of vesicles assembled from an extract of polar soy lipids on tracing paper. Scale bar is 50 μm.

FIG. 21E shows a confocal image of vesicles assembled from an extract of total *E. coli* lipids on tracing paper. Scale bar is 50 μm.

FIG. 21F shows a confocal image of vesicles assembled from an extract of total porcine brain lipids on tracing paper. Scale bar is 50 μm.

Figure 22:
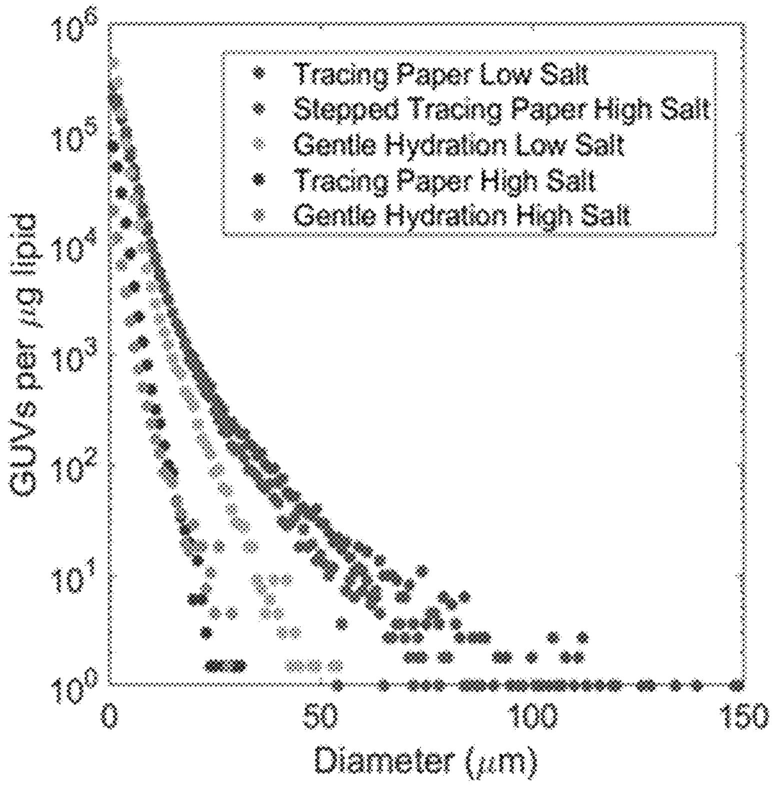

FIG. 22 shows a histogram of GUV diameters (bin width=1 μm) for vesicles formed by PAPYRUS on tracing paper under low salt conditions (uppermost set of points); formed by PAPYRUS on tracing paper under stepped low salt→high salt conditions (next lower set of points); formed by gentle hydration under low salt conditions (next lower set of points); formed on tracing paper under high salt conditions (next lower set of points); and formed by gentle hydration under high salt conditions (lowermost set of points). Data points are the average counts per bin normalized to the mass of lipid deposited on the substrate and were obtained from five independent experiments. Note the logarithmic scale on the y-axis.

Figure 23:
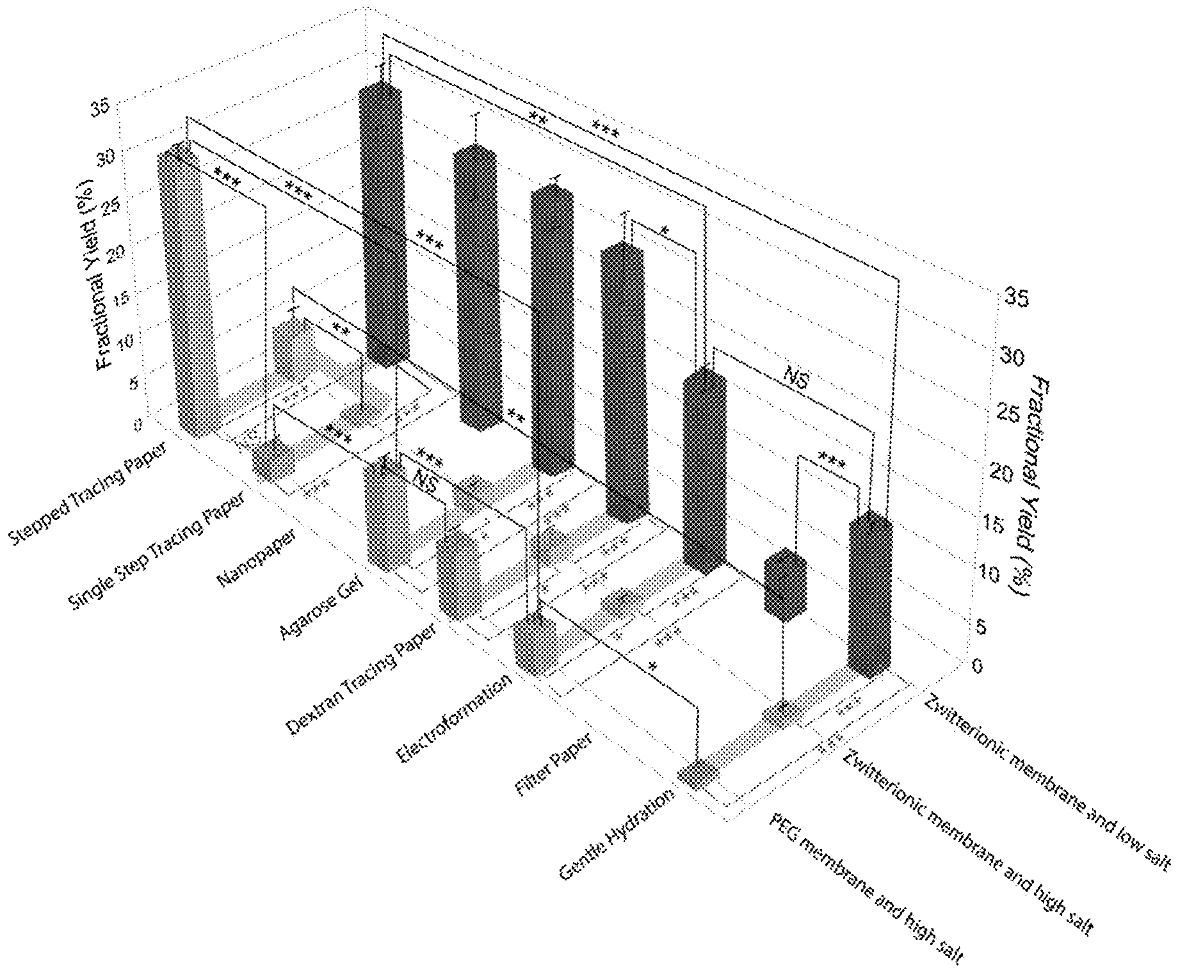

FIG. 23 shows a three-dimensional bar plot of the mean fractional yields of GUVs obtained using different techniques under three buffer conditions (low salt, high salt and high salt/PEG). The rearmost row of bars shows the fractional yields of zwitterionic membranes (i.e., DOPC-containing membranes) obtained in low salt conditions, the middle row of bars shows the fractional yields of zwitterionic membranes obtained under high salt conditions, and the front-most row of bars shows the fractional yields of PEG-modified membranes obtained under high salt conditions. Each bar represents an average value obtained from 5 independent experiments, in which the fractional yield in each experiment was calculated from ~100,000 GUVs. The error bars denote the standard deviation from the mean. * indicates $p<0.5$,  indicates $p<0.01$, * indicates $p<0.001$, and NS indicates not significant. Coefficients of variation ranged from 5% to 10%, highlighting the importance of multiple repeats and statistical testing to determine the significance of measured differences.

Figure 24:
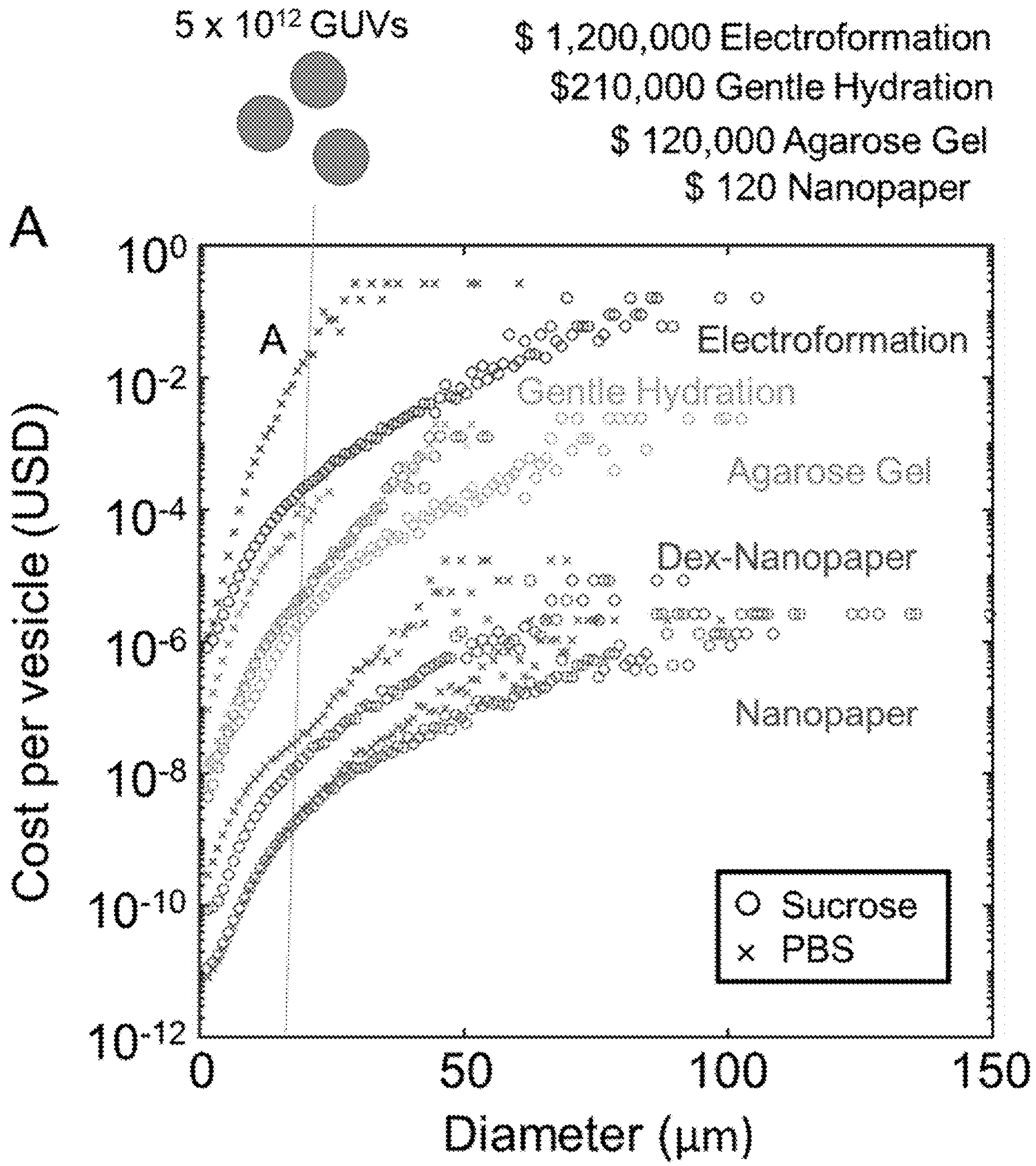

FIG. 24 shows a plot of substrate cost per vesicle, with respect to vesicle size, for electroformation (top two sets of data points), gentle hydration (next two lower sets of points), agarose gel-assisted hydration (next two lower sets of points), PAPYRUS on dextran-coated tracing paper (next two lower sets of points) and PAPYRUS on tracing paper (lowest two sets of points). Vesicle formation was conducted under low salt conditions (sucrose, -o-) and high-salt conditions (PBS, -x-). Bin widths are 1 μm.

Figure 25:
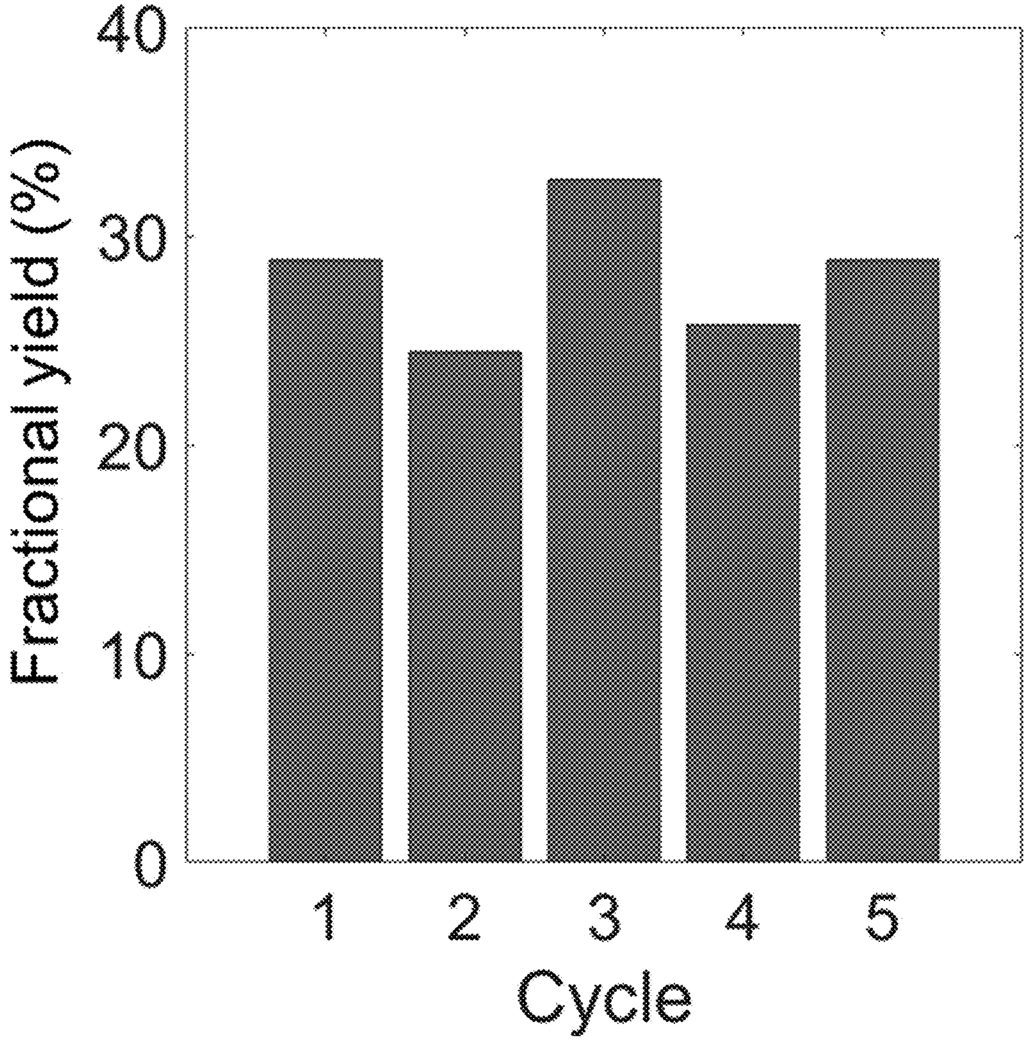

FIG. 25 shows fractional yield of vesicles at each of five cycles of vesicle formation by PAPYRUS on commercial tracing paper.

Figure 26:
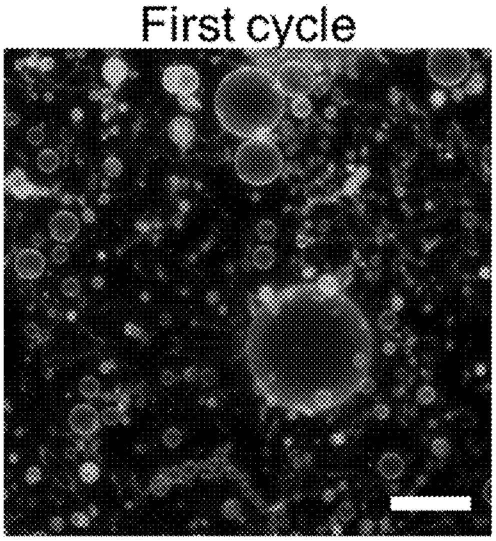
Figure 26:
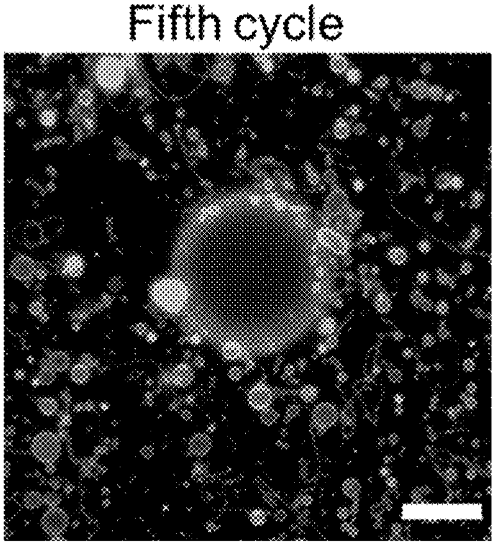

FIG. 26 shows confocal images of vesicles formed on virgin tracing paper (top, "First cycle") and after a fifth cycle of vesicle formation on the same paper (bottom, "Fifth cycle").

Figure 27:
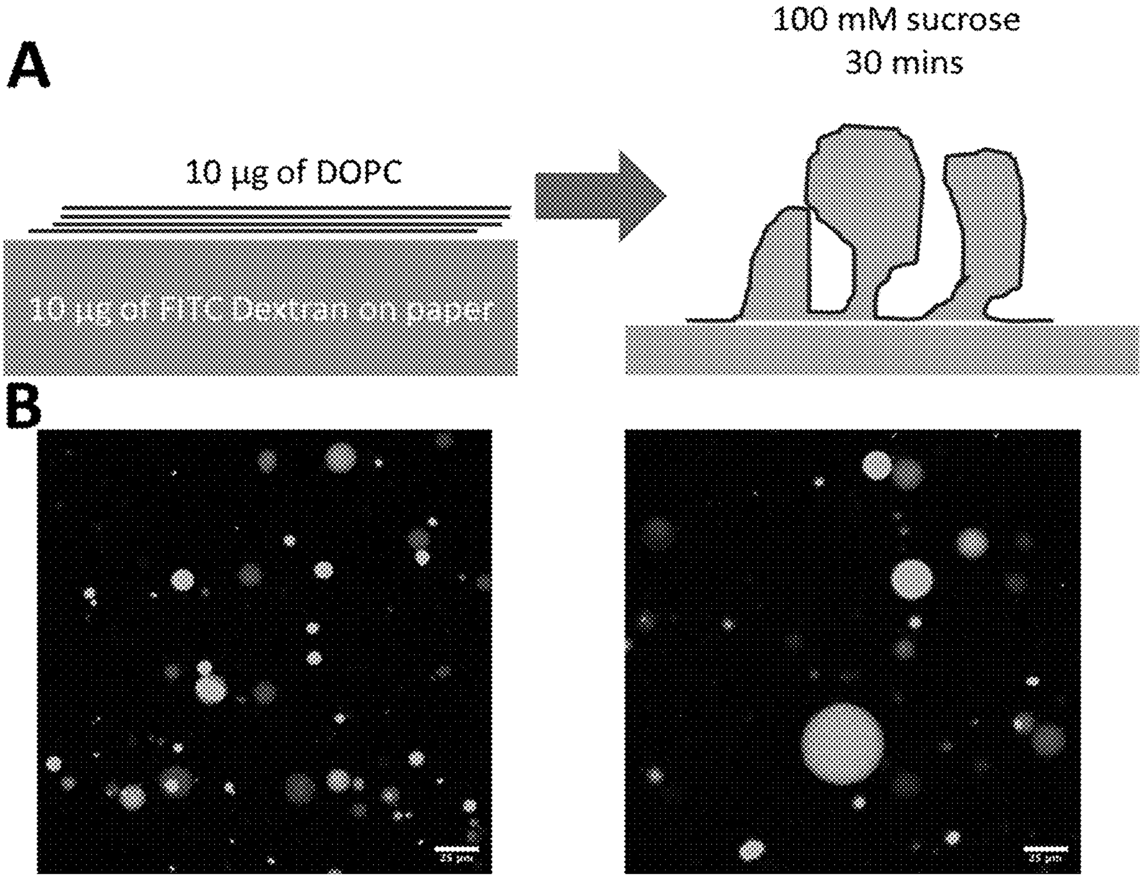

FIGS. 27A & B describe a method for loading hydrophilic cargo into vesicles. FIG. 27A is a schematic diagram of the process of loading a solution containing a hydrophilic compound (dextran being used as an example) into vesicles by (1) depositing the solution onto the surface of a substrate (in this example, tracing paper); (2) allowing the solution to dry onto the substrate, (3) applying a lipid to the substrate (in this example, DOPC), and (4) placing the lipid-coated substrate in an aqueous solution. The hydrophilic compound is dissolved from the substrate into the aqueous solution and is encapsulated in the lumen of the vesicles that are formed. FIG. 27B shows confocal images of vesicles formed by this procedure. The fluorescent interior of the vesicles indicate that the dextran-FITC has been incorporated into the vesicles.

Figure 28:
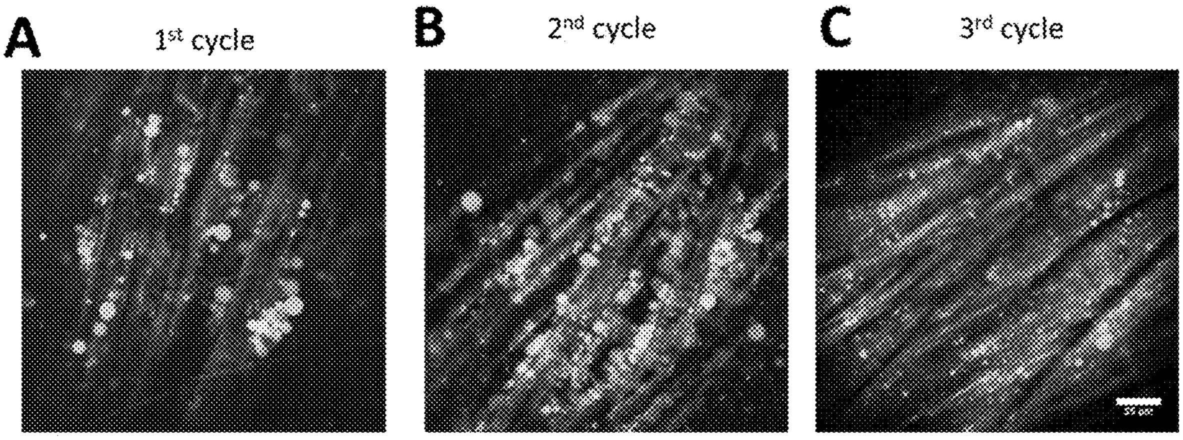

FIGS. 28A-C show confocal images of FITC-dextran-containing vesicles formed on silk fiber by deposition of the FITC-dextran on the fiber prior to contact of the fiber with lipid. FIG. 28A shows an image after the first cycle of vesicle formation. FIG. 28B shows an image after the second cycle of vesicle formation. FIG. 28C shows an image after the third cycle of vesicle formation. Scale bar is 25 μm.

Figure 29:
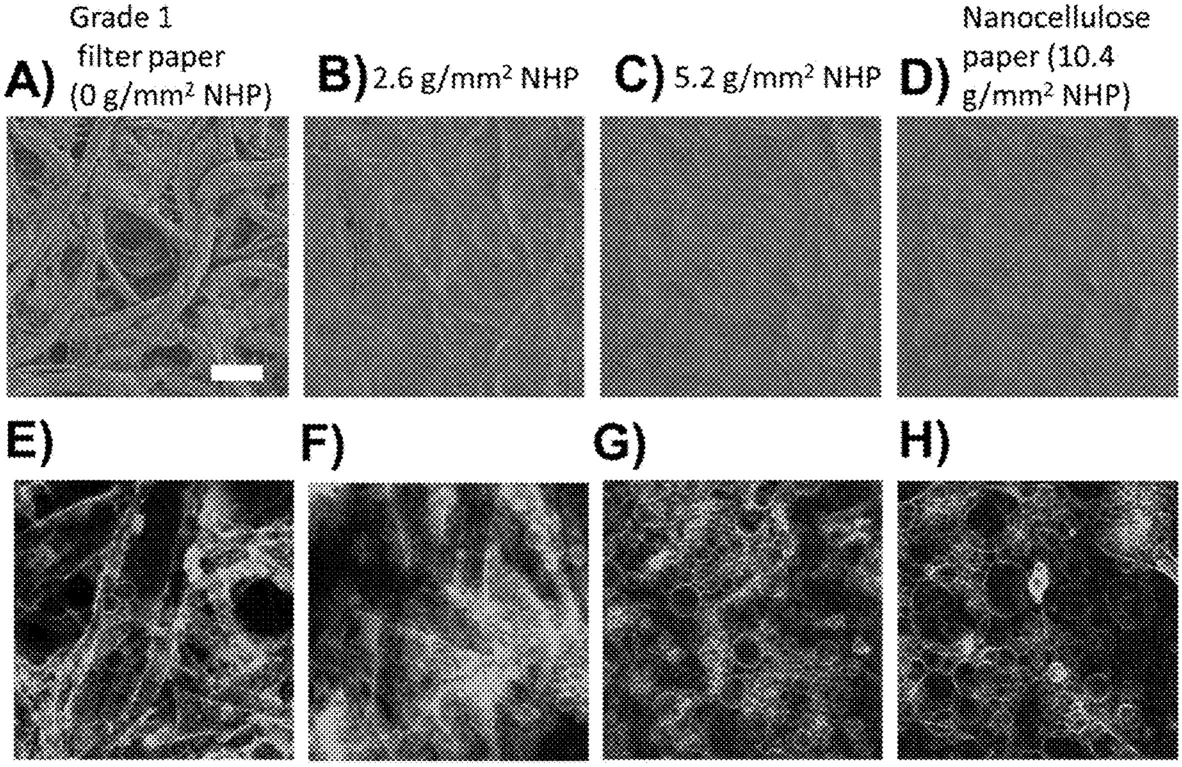

FIGS. 29A-H show analysis of vesicle formation on hybrid nanopapers. FIGS. 29A-29D show low-power scanning EM images with a field of view of 300 μm×300 μm and a captured pixel size of 0.67 μm. FIG. 29A shows a SEM image of Grade 1 filter paper (containing 0 $g/mm^2$ nanocellulose). FIG. 29B shows a SEM image of a nanohybrid paper containing 2.6 $g/mm^2$ nanocellulose. FIG. 29C shows a SEM image of a nanohybrid paper containing 5.2 $g/mm^2$ nanocellulose. FIG. 29D shows a SEM image of a nanocellulose paper containing 10.4 $g/mm^2$ nanocellulose. Scale bar is 50 μm. FIGS. 29E-29H show fluorescence confocal images of GUVs growing on the surfaces of the four substrates after two hours of vesicle growth. FIG. 29E shows vesicles grown on filter paper (Whatman G1). FIG. 29F shows vesicles grown on nanohybrid paper containing 2.6 $g/mm^2$ nanocellulose. FIG. 29G shows vesicles grown on nanohybrid paper containing 5.2 $g/mm^2$ nanocellulose. FIG. 29H shows vesicles grown on nanocellulose paper (containing 10.4 $g/mm^2$ nanocellulose).

Figure 30:
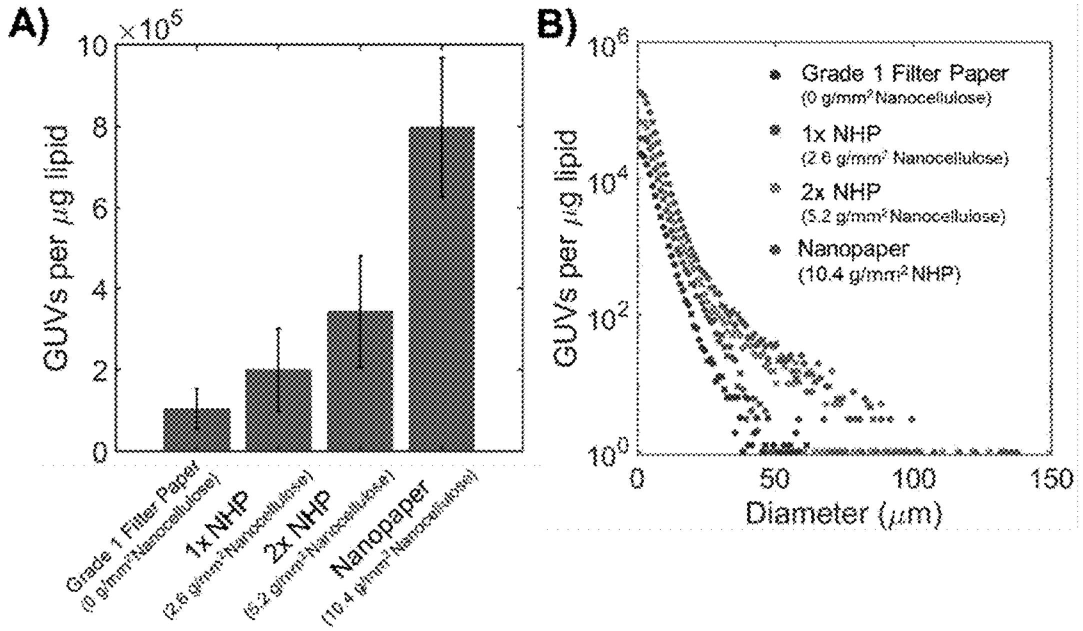

FIGS. 30A & 30B show yields and sizes of vesicles obtained on various substrates. FIG. 30A shows total mean normalized vesicle counts (GUVs per microgram lipid) of DOPC-bounded vesicles obtained on, from left to right, filter paper, nanohybrid paper containing 2.6 $g/mm^2$ nanocellulose, nanohybrid paper containing 5.2 $g/mm^2$ nanocellulose, and nanopaper (containing 10.4 $g/mm^2$ nanocellulose). FIG. 30B shows a histogram of GUV diameters (bin width=1 μm) normalized with respect to microgram lipid deposited on the substrate. Nanopaper (top-most set of data points) provided both the highest number of vesicles and the largest vesicle sizes (up to 150 μm in diameter), followed by 5.2 $g/mm^2$ NHP (next lower set of points), 2.6 $g/mm^2$ NHP (next lower set of points) and filter paper (lowest set of points). Note the logarithmic scale of the y-axis.

FIGS. 31A-31D show confocal images of GUVs grown under high salt conditions (1×PBS) on tracing paper coated with various polymers. FIG. 31A shows GUVs growing on tracing paper that had been coated with Ficoll. FIG. 31B shows GUVs growing on tracing paper that had been coated with hyaluronic acid (HA). FIG. 31C shows GUVs growing on tracing paper that had been coated with carboxymethylcellulose (CMC). FIG. 31D shows GUVs growing on tracing paper that had been coated with dextran.

DETAILED DESCRIPTION

For the purposes of the present disclosure, the terms "amphiphile," "amphiphilic molecule" and "amphipathic molecule" all refer to a molecule that contains one or more hydrophobic regions as well as one or more hydrophilic regions, such that a population of such molecules is capable of forming lamellar structures in aqueous solution.

The term "vesicle" or "liposome" refers to a structure comprising an aqueous center bounded by one or more membranes (or lamellae). A vesicle can be bounded by a single membrane (a unilamellar vesicle), by two (concentric) membranes (a bilamellar vesicle), by three membranes (a trilamellar vesicle) or more. Vesicles can be spherical or elongated (i.e., having the shape of a solid oval) in shape. Polymeric structures comprising multiple spherical vesicles arranged in a linear polymer can also be formed using the methods described herein.

The terms "substrate" and "fiber" refer interchangeably to fibrous solids such as, e.g., cellulose, synthetic fibers, and metal meshes. In the methods described herein, amphiphilic molecules are deposited on a substrate as part of the process for forming vesicles.

The terms "nanocellulose," "nanopaper" and "nanostructured cellulose" refer to a substrate made from cellulose nanofibrils, for example, by solution casting or filtration of nanocellulose pulp.

The present disclosure provides, inter alia, new methods for rapid production of vesicles using fabrics (such as silk, cotton, rayon, polyester, nylon or steel wool, for example) and sheets (such as nanopaper, cellulose or dialysis membranes, for example) that are capable of forming vesicles using both positively- and negatively-charged lipids, do not require power and have minimal toxicity. The process can be summarized as follows: (1) a fabric or sheet is coated with a suitable amphiphile such as a fatty acid, a phospholipid, or an amphiphilic polymer (e.g. a diblock copolymer or a triblock copolymer) and (2) the dry, amphiphile-coated fabric or sheet is placed in contact with an aqueous solution to induce formation of vesicles. Additional amphiphiles include catanionic surfactants, bolaform amphiphiles and Archael lipids.

In additional methods, release and harvesting of vesicles from vesicle-coated substrates is achieved by fluid (e.g., an aqueous solution) flow across or through the substrate.

The disclosed methods provide the following advantages over existing methods for vesicle formation: (1) no specially-prepared substrates are required, since fabrics and paper sheets are readily available; (2) it is rapid and efficient: vesicles can be obtained within one hour and are free of contamination from substrate and solvents; and (3) the process is easily scalable since it does not require the use of either power or special equipment.

Since the methods do not require the use of power, substrates (such as, for example, fabrics and sheets as described above) can be precoated with amphiphile at a factory or other manufacturing site, then shipped dry to the point of use, at which, for example, vesicles can be harvested (by exposing the amphiphile-coated substrate to water or an aqueous solution) or the vesicle-coated substrates can be used for, e.g., cosmetic or therapeutic applications. The methods of vesicle formation are compatible with current manufacturing practices and are easily amenable to scale-up and quality control. For example, amphiphiles can be printed onto paper, akin to printing of ink, by adapting sheet making and paper coating machinery to deposit amphiphiles continuously over large areas of paper and fabric. At the site of use, another embodiment would involve providing the amphiphiles in the form of a powder that can be dissolved in a suitable solvent at the site of use prior to deposition on the substrate. Another embodiment at the site of use would involve providing the amphiphile pre-dissolved in a suitable solvent with a suitable dispersal device such as an aerosol can, an atomizer, or pipette; allowing the amphiphile to be deposited onto the substrate prior to vesicle growth.

Vesicles

Vesicles, or liposomes, as disclosed herein, contain a hydrophilic lumen and a hydrophobic membrane surrounding the lumen. Biological membranes are often made up of a repeating arrangement of amphiphilic (or amphipathic) molecules; i.e., molecules that comprise both hydrophilic and hydrophobic portions, often disposed at opposite ends of the molecule (for example, phospholipids). In aqueous solutions, amphipathic molecules arrange themselves into a bilayer such that their hydrophobic portions face each other (forming a hydrophobic core of the membrane) and their hydrophilic portions face outward toward the solvent and inward toward an aqueous lumen. The hydrophobic core of the bilayer is able to exclude charged molecules (e.g., ions) and hydrated macromolecules, while allowing passage of water and small hydrophobic molecules.

The vesicles disclosed herein are useful, inter alia, because hydrophobic molecules (e.g., drugs) can be solubilized or dispersed in the hydrophobic core of the membrane. Vesicles can then be dispersed in bulk solution, thereby increasing the availability of a hydrophobic drug dispersed in the membrane of a vesicle, compared to the availability of the same hydrophobic drug administered in non-vesicular form. In addition, vesicles can fuse with the plasma membrane of a cell (e.g., a mammalian cell, a plant cell, a bacterial cell or a fungal cell), thereby delivering cargo (either a hydrophilic molecule contained in the lumen or a hydrophobic molecule contained in the membrane) to the cell. Fungal cells, certain bacterial cells, and plant cells possess cell walls exterior to their plasma membrane; methods for breaching cells walls, thereby providing access to the plasma membrane, are known in the art. Furthermore, a receptor can be incorporated into the membrane of the vesicle to target the vesicle to a specific location (e.g., body tissue, cell type). Receptors for membrane proteins are known in the art; to provide just one example, the receptor for vascular endothelial growth factor (VEGF) is overexpressed on the surface of certain cancer cells; accordingly, VEGF or anti-VEGF receptor antibodies can be incorporated into the membrane of a vesicle to target the vesicle to a cell containing VEGF receptors in its cell membrane. Positively-charged molecules can be incorporated into the polar portion of the membrane, which will also aid in fusion of the vesicle with the negatively-charged membrane of mammalian cells.

In addition to being capable of solubilizing hydrophobic molecules in the membrane, vesicles can also encapsulate and solubilize hydrophilic molecules within their lumen. In these embodiments, encapsulated hydrophilic material is protected from the environment (e.g., blood, tissue fluid, saliva, stomach acid, etc.) until it is released from the vesicle. Disruption of the vesicle to release its luminal contents can be achieved by applying physical and chemical gradients to the vesicles, such as a gradient in osmotic pressure, a gradient in pH, and/or a gradient in temperature, any of which will cause the vesicles to burst and release their contents.

Optimal conditions for growth will vary with the type of amphiphile used to assemble the vesicle, and can include initial surface concentration of the amphiphile, pH and ionic strength of the growth buffer, and the time and temperature of incubation in growth buffer. Depending on assembly conditions, vesicles exhibit amphiphile-specific variation in size, lamellarity and structure.

Amphiphilic Molecules

Amphiphilic molecules (also known as amphipathic molecules) are compounds that contain one or more hydrophobic region(s) and one or more hydrophilic region(s) within their molecular structure. Exemplary amphiphilic molecules include phospholipids, fatty acids, sphingolipids, ceramides, fatty alcohols, quaternary ammonium surfactants, and amphiphilic polymers such as, for example, amphiphilic block copolymers (e.g., amphiphilic diblock copolymers, amphiphilic triblock copolymers). Additional exemplary amphiphilic molecules include oleic acid, phosphatidylcholine, phosphatidylglycerol, phosphatidylserine, phospatidic acid, phosphatidylethanolamine, DOPG, DOPS, DOPC, DPPC, DOPA, DOTAP, POPC, POPG, SOPC, and SOPG, for example. Biological extracts that contain amphiphilic molecules include lecithin (e.g., soybean lecithin, egg lecithin), polar extracts of any animal product containing cells or cellular organelles, such as *E. coli* total extract, *E. coli* Polar Extract, Heart Polar Extract, Liver Polar Extract, Soybean polar Extract, Egg, brain total extract and yeast polar extract. Further exemplary amphiphiles include catanionic surfactants, bolaform amphiphiles and Archael lipids.

Additional exemplary amphiphiles include DOPC:TopFluor-Cholesterol, DOPC:Rhodamine-DPPE, ESM:DOPC:Chol:TopFluor-Cholesterol:Rhodamine-DPPE, DPPC:TopFluor PC, DOPS:DOPC:TopFluor-Cholesterol, POPG:TopFluor-Cholesterol, DOTAP:TopFluor-Cholesterol, didodecyldimethylammonium bromide (DDAB), myristoleic acid, Dodecyltrimethylammonium bromide (DTAB), and Didodecyldimethylammonium bromide (DDAB).

Substrates

Using the methods disclosed herein, vesicles (e.g., liposomes, GUVs) can be deposited on a substrate and the vesicle-coated substrates can be used as disclosed elsewhere herein. Substrates for use in the disclosed methods include, but are not limited to fibers (e.g., curved fibers, cylindrical fibers, flattened cylindrical fibers, wavy cylindrical fibers or linear poly-spherical fibers) and metal mesh (e.g., stainless steel, copper or steel wool). Fibers include naturally-occurring fibers, such as cellulose, silk and wool. Cellulose fibers include papyrus, paper, wood pulp, cotton, hemp and jute. Fibers also include synthetic fibers, such as, for example, nylon and polyester and semi-synthetic fibers such as, for example, rayon. Fibers also include inorganic synthetic fibers such as, for example, fiberglass. Fibers also include nanofibers, such as tracing paper, nanocellulose paper (i.e., nanostructured cellulose paper), or regenerated cellulose membrane (e.g., dialysis membrane).

Fibers can also include three dimensional tissue culture scaffolds, and bandages such as polycaprolactone (PCL) nanofibers and collagen nanofibers. Collagen can be derived from rat's tail and decellularized bovine myocardium. Nanocellulose can be derived from, e.g., plant biomass, bacteria, algae and tunicates. Fibers can be randomly enmeshed (e.g., paper), woven (e.g., fabrics such as cotton), non-woven (e.g., felt) or aligned in certain directions. For the purposes of this disclosure, the terms "fiber" and "fabric" are used interchangeably.

Cellulose is an abundant biopolymer that is both hygroscopic and hydrophilic, yet it is essentially insoluble in water and most organic solvents, even at elevated temperatures. As disclosed herein, hydrating dried lipid films on cellulose provides a facile route to preparing vesicles (e.g., giant liposomes) that are predominantly unilamellar; i.e., giant unilamellar vesicles (GUVs). Without wishing to be bound by theory, it is likely that curvature of cellulose fibers, along with the swelling of cellulose fibers upon exposure to water provides a driving force for separating the lamellae, present in hydrated multilayer lipid stacks, into unilamellar vesicles. The use of cellulose as a substrate for the production of vesicles, such as liposomes, is a significant departure from current methods (utilizing, e.g., Teflon, electric fields, etc.), and greatly simplifies procedures for fabricating biological vesicles.

As described herein, the curvature of the elements (e.g., fibers, fibrils) within a substrate is positively correlated with the yield of vesicles obtained on that substrate using the methods described herein. Flat substrates such as glass, which has a radius of curvature=0, provide a low yield of vesicles. For an outwardly curved linear fiber or fibril, which provides a higher vesicle yield, one principal radius of curvature is >0. Fibers can also be curved inward (i.e., concave or collapsed fibers), in which case the radius of curvature is <0. In addition, a fiber containing a collection of spheres (e.g., a string of spheres), which would have two principal non-zero radii of curvature, will also provide high yields of vesicles.

In certain embodiments, fibers or fibrils have dimensions (e.g., length, diameter) in the nanometer range; e.g., nanofibers or nanoscale fibers.

In certain embodiments, nanocellulose paper is used as a substrate. Plant-derived cellulose fibers have a hierarchical structure. Smook, G. Handbook for Pulp and Paper Technologists. (TAPPI Press, 2016). Cellulose fibers are tens of micrometers in diameter and are composed of microfibrils which themselves contain bundles of hydrogen-bonded nanofibrils having a diameter of approximately 5-60 nm. FIG. 19, see also Klemm et al. (2011) *Angew. Chemie-Int. Ed.* 50:5438-5466. Chemical hydrolysis and high-pressure mechanical homogenization defibrillates plant-derived cellulose fiber pulp into nanocellulose pulp. Klemm et al., supra. Nanocellulose pulp can be converted to nanocellulose paper by, e.g., solution casting or filtration. Nanocellulose can also be obtained from cellulose-producing bacteria, albeit in smaller quantities and at higher costs. Klemm et al., supra.

Cellulose nanofibrils can obtained from cellulose fibers through mechanical homogenization using shear, pressure, and/or chemical treatments. See, for example, Li Y-Y et al. (2018). Review of Recent Development on Preparation, Properties, and Applications of Cellulose-Based Functional Materials. *Int J Polym Sci.;* 2018:1-18. doi:10.1155/2018/8973643. The water is allowed to evaporate at room temperature, leaving behind a thin sheet of nanopaper. The nanopaper is rinsed and cleaned thoroughly with chloroform and then water. Alternately commercial tracing paper, which is also mechanically and chemically refined to obtain a dense fibrillar surface, can be used.

Additional exemplary substrates include three-dimensional tissue culture scaffolds, bandages such as polycaprolactone (PCL) nanofibers, collagen nanofibers, and extracellular matrix fibers (i.e., decellularized extracellular matrix).

Vesicle Formation

Vesicles are formed by applying a dispersion of an amphiphilic molecule to a substrate (e.g., a fiber such as cellulose) and allowing the dispersed amphiphile to dry onto the substrate; e.g., by evaporation of the solvent in which the amphiphile is dispersed, followed by contact of the dried, amphiphile-coated substrate with an aqueous solution (i.e., a "growth buffer"). After deposition of amphiphile onto a substrate and evaporation of the solvent, the amphiphile forms deposits on the surface of the substrate. Contact of the amphiphile-coated substrate with water (or with an aqueous solution) causes the amphiphile deposit to rearrange into stacks that form vesicles.

Any solvent in which a particular amphiphile can be dispersed can be used. It is straightforward to determine whether a particular solvent is capable of dispersing a particular amphiphile. Suitable solvents in which an amphiphile can be dispersed include both polar and nonpolar solvents. For example, a suitable solvent can be an alkane such as, e.g., pentane, hexane or octane; an aromatic solvent such as, e.g., chloroform, toluene, benzene, carbon tetrachloride, acetone, methylene chloride, xylene or squalene; an alcohol, such as, e.g., methanol, ethanol, isopropanol and higher alcohols; acetone, or water.

Vesicles made by the methods disclosed herein can be unilamellar or can comprise multiple (e.g., concentric) membranes. The degree of lamellarity (i.e., unilamellar, multilamellar) of vesicles made by the methods described herein (or the formation of other structures such as multivesicular structures and amphiphile droplets) is correlated with the thickness of the layer of amphiphile that is deposited on the substrate. In general, unilamellar vesicles are produced from amphiphile layer thicknesses of 1-50 bilayer stacks; corresponding to 10-100 micrograms amphiphile applied to a circular disc of substrate 9.5 mm in diameter. Formation of multilamellar vesicles requires on the order of 100 or more bilayer stacks of amphiphile on the substrate; corresponding to a mass of amphiphile of 100 micrograms or greater applied to a 9.5 mm diameter disc of substrate. These guidelines can be extrapolated, by converting the above guidelines into amphiphile mass/substrate surface area values, to provide guidelines for formation of uni- and multi-lamellar vesicles on non-circular substrates.

Growth Buffers

Formation of vesicles on lipid- or amphiphile-coated substrates occurs when the dried, coated substrate is placed in an aqueous "growth buffer." Choice of growth buffer depends on factors such as, e.g., vesicle size, vesicle cargo, and the nature of the lipid or amphiphilic molecule used to assemble the membrane of the vesicle. Growth buffers can range from water (e.g., distilled water, ultrapure water) to sugar solutions (e.g., sucrose) to ionic buffers such as, for example, Tris-buffered saline (TBS), 4-(2-hydroxyethyl) piperazine-1-ethanesulfonic acid (HEPES) or phosphate-buffered saline (PBS). Biological fluids such as, for example, blood, plasma, serum, tears, urine and saliva can also be used as growth buffers.

Vesicle Loading

When dispersed in growth buffer, macromolecules such as proteins and polysaccharides (i.e., cargo) are spontaneously incorporated from solution into the lumen of the vesicle. For certain amphiphiles, elevated temperatures (i.e., temperatures above room temperature) may be required for vesicle assembly. In these cases, vesicle formation can be temporally uncoupled from loading of cargo by coating substrate with amphiphile at elevated temperature (e.g., 80° C.) in the absence of cargo, cooling the amphiphile-coated substrate to room temperature or below, and contacting amphiphile-coated substrate with an aqueous solution of the cargo molecule(s).

Loading of cargo from solution into vesicles is has a diffusion-driven component; dependent on the concentration of the cargo molecule, the diffusion coefficient of the cargo molecule and the size of the vesicles. In certain embodiments, the concentration of cargo in the loading solution is on the order 1 μM. In additional embodiments, the concentration of cargo molecule can be between 0.5 and 2 μM, or between 0.1 and 5 μM, or between 1 and 10 μM. For a cargo molecule with a diffusion coefficient of $10^{-11}$ $m^2$ $s^{-1}$, the characteristic time for diffusion of the molecule into vesicles is about 10 s. In certain embodiments, loading times of 10 sec, 30 sec, 1 min, 5 min, 10 min, 20 min 30 min and 1 hr can be used.

For loading of hydrophobic molecules, the molecules can be added directly to a dispersion of amphiphile in solvent prior to coating the substrates. Alternately hydrophobic cargo can be deposited on the substrate either before or after depositing the amphiphile. After preparing the coated substrate, hydrophobic cargo will partition into the hydrophobic region of the bilayer membranes immediately upon hydration.

To provide just one example, the hydrophobic dye Nile Red is sparingly soluble in water, but is highly soluble in chloroform. Accordingly, Nile Red can be mixed with an amphiphile (e.g., a lipid) prior to deposition of the amphiphile on a substrate. Upon vesicle formation (e.g., after contacting a Nile Red/lipid-coated fiber with water), the Nile Red, trapped in the membrane of the vesicles, adheres to the fiber but is insoluble in the growth buffer. Accordingly, the fibers fluoresce brightly in a non-fluorescent background of growth buffer. Optionally, vesicles can then be detached from the fiber, carrying the Nile Red (still trapped in the vesicle membranes) from the fibers into the aqueous phase.

Hydrophilic cargo can also be deposited on the substrate for simultaneous dissolution and loading into the vesicles. For example, the polysaccharide dextran is highly soluble in water. An aqueous solution of a hydrophilic molecule (e.g., a polysaccharide such as dextran) can be deposited on a substrate and allowed to dry. An amphiphile can then be deposited onto the substrate containing the dried hydrophilic molecule. Upon vesicle formation, the hydrophilic molecule (e.g., dextran) is dissolved in the solution (i.e., the growth buffer) and is encapsulated into the lumens of the vesicles. See FIG. 27.

Controlled Vesicle Formation and Release

When amphiphile is deposited onto a substrate using the methods and compositions disclosed herein, it forms lamellar stacks of amphiphile. Upon contact with water or aqueous solutions, these stacks spontaneously vesiculate. For certain applications, it is desirable to prevent or delay vesiculation, while maintaining the substrate in an aqueous environment; then trigger vesiculation at a later time.

Accordingly, methods to delay and then trigger vesiculation from an amphiphile-coated substrate in aqueous solution are provided. The methods are based on the fact that solutions with high osmotic pressure prevent vesiculation. Accordingly, an amphiphile-coated substrate is hydrated in aqueous solutions containing a dissolved substance (osmolyte) that exerts an osmotic pressure greater than 1 kPa, which prevents vesiculation. Such a condition can be achieved by using a solution of, for example, 2 mM Ficoll 400. Vesicle formation can then be triggered by diluting the osmolyte to a concentration that allows vesiculation; e.g., that results in an osmotic pressure below 1 kPa (which corresponds to a concentration of 0.7 mM Ficoll 400 or less), which causes vesicles to form.

Figure 9:
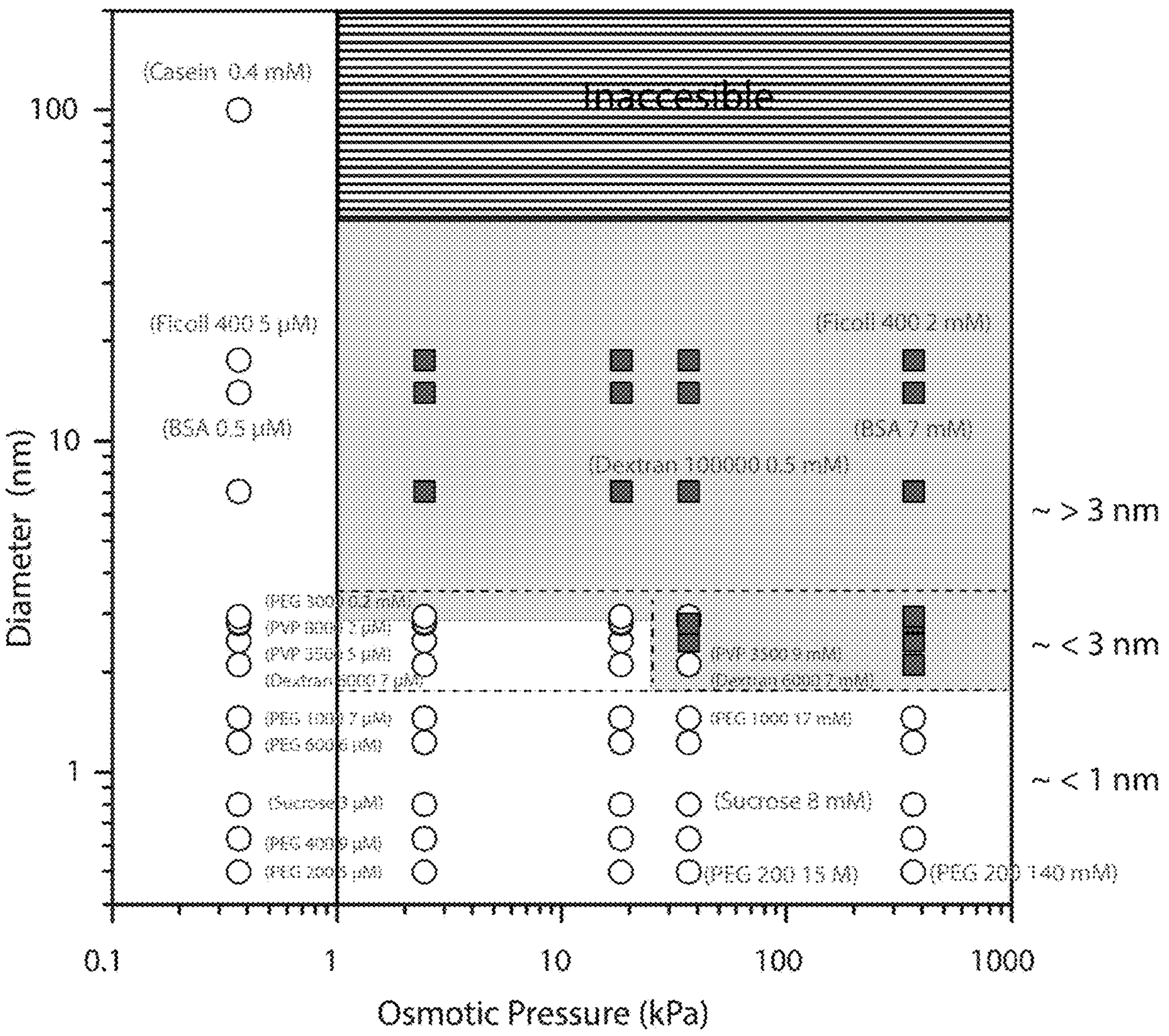
FIG. 9 shows experimentally determined thresholds for inhibition and promotion of vesiculation by various osmolytes. The shaded region of the graph includes condition under which vesiculation is inhibited.

Additional osmolytes that can be used in these methods include, but are not limited to casein, bovine serum albumin (BSA), dextrans (e.g., Dextran 100,000, Dextran 6,000), polyvinylpyrrolidones (e.g., PVP 3500, PVP 800, PVP 350), and polyethylene glycols (e.g., PEG 3000, PEG 600, PEG 400). Conditions for inhibition and induction of vesicle formation will differ for different osmolytes, and are shown in FIG. 9.

Applications of this method include shipping amphiphile-coated substrates in wet (osmolyte-containing) pouches in an activated state (for example to preserve the function of sensitive protein or drugs) and then placing the coated substrate into a solution lacking osmolyte to trigger vesiculation.

Vesiculation can also be controlled by temperature. In these methods, amphiphile-coated substrates are hydrated in aqueous solutions below the transition temperature of the amphiphile. When below the transition temperature, the amphiphile does not vesiculate on the substrates. Such a condition can be achieved for example by using as an amphiphile 1,2-dipentadecanoyl-sn-glycero-3-phosphocholine which has a transition temperature of 35° C. Upon increasing the temperature above 35° C., for example by placing the amphiphile-coated substrate in contact with the human body, which has a temperature of 37° C., vesicles are formed. Amphiphile-coated substrates can thus be shipped in an activated state and then vesiculation triggered when suitable temperature conditions are achieved.

Additional amphiphiles are described elsewhere herein, and the transition temperatures of amphiphiles are known in the art.

Manufacturing

The methods disclosed herein for vesicle assembly onto fibers are compatible with the production of large numbers of vesicles in a centralized manufacturing facility. Fabrics and papers are routinely processed using large machines, e.g., for drying, printing, washing, etc. Accordingly, batch processing methods and assembly line procedures for obtaining vesicles are feasible using the methods disclosed herein. Such large-scale methods are impractical and/or prohibitively expensive using current procedures for manufacturing vesicles. The fact that fabrics are reusable (see Example 6) is also consistent with large-scale manufacturing of vesicles using the methods described herein.

Therapeutic Compositions and Therapeutic Applications

In certain embodiments, vesicle-coated fibers (e.g., silk, cotton) provide therapeutic compositions for use as bandages containing, e.g., analgesic, anesthetic, antibiotic (e.g., antimicrobial, antifungal) and/or antiviral compounds. Both hydrophilic and/or hydrophobic compounds can be contained in such compositions. Hydrophilic compounds are encapsulated in the lumens of vesicles, where they remain protected from the environment, and from drug-deactivating molecules that can be released by certain infectious microorganisms, until release is triggered.

Release can be triggered, for example, by wetting the bandage with water or an aqueous solution such as saline or PBS, or by contact with bodily fluids in the wound. Release can also be triggered by changes in the temperature of the wound compared to the surrounding tissue, (e.g., due to inflammation and/or infection), and/or changes in pH in the wound compared to the surrounding tissues.

Depending on vesicle size, degree of lamellarity of the vesicle, lipid (or amphiphile) composition of vesicle, shape of the vesicle, diffusion coefficient of the compound, partition coefficient of the compound, temperature, and the presence or absence of flow, the release rate of the compound(s) into a wound can be controlled. Various types of targeting molecules (e.g., lectins, antibodies, nanobodies, FAB fragments, protein receptors or ligands, Annexin V) can be incorporated into vesicle membranes to direct the vesicle to a particular cell or tissue in a subject.

The chemotherapeutic agents doxorubicin and taxol are examples of hydrophobic drugs that can be transported and delivered by vesicles as described herein. These compounds have molecular characteristics similar to those of Nile Red, such as fused planar cyclic rings, and thus possess similar loading characteristics. Release of these drugs occurs when the vesicle membranes fuse with the plasma membrane of target cells, or when the vesicles are taken up (e.g., endocytosed) by the target cells.

Additional exemplary therapeutic cargo molecules include viruses (which can be used a vectors for gene delivery), bacteriophages (which can be used as anti-bacterial agents for, e.g., treatment of infections by antibiotic-resistant bacteria) and silver nanoparticles (which can also be used as anti-bacterial agents).

Additional therapeutic compositions include stents (e.g., for delivery of an anticoagulant compound), suppositories, pessaries (e.g., for delivery of a contraceptive compound) and sublingual applicators.

Cosmetic Compositions and Cosmetic Applications

As noted, vesicles can be used as carriers of both hydrophilic substances (in their lumen) and/or hydrophobic substances (in their membrane). In certain embodiments, the vesicle-coated fabrics disclosed herein are used as applicators (e.g., skin patches, face masks) for cosmetic agents. Human skin has a hydrophobic barrier, and liposomal formulations have been shown to increase transport of hydrating molecules and other adjuvants into deeper skin layers.

Accordingly, in one embodiment for providing anti-aging cosmetics, the disclosure provides vesicle-coated silk sheets wherein the vesicles contain an anti-aging agent such as, for example, retinol. Retinol, being a hydrophobic compound, is incorporated into vesicle membranes by, for example, co-dispersing retinol with an amphiphile in a solvent, applying the liquid to a substrate such as cotton or silk, and drying. Thus, retinol-coated silk face masks for skin treatment are provided. Application of the mask (e.g., to the face) followed by moistening and/or gentle agitation of the mask will release the retinol onto the skin of the subject.

In additional embodiments for dermal rejuvenation, vesicle-coated fibers, in which the vesicles contain ceramides in their membranes, are used. Many skin lipids are composed of high-melting temperature ceramides that are solid at room temperature and therefore difficult to transport into skin. Dispersing such ceramides in the vesicle membrane will facilitate incorporation of the ceramide(s) into the skin.

Substrates can be coated with amphiphiles by dissolving amphiphile in a suitable solvent or mixtures of solvents (for example, methanol, grain alcohol, acetone, water and/or mixtures thereof), then applying the amphiphile to a fabric or other substrate by using, for example, an aerosolizer, nebulizer, or spray bottle.

Accordingly, additional compositions include vesicle-coated fabrics (e.g., performance fabrics for use in sports and exercise) containing antiperspirants and/or fragrances. In these embodiments, a cosmetic molecule (e.g., an antiperspirant and/or a fragrance) is loaded into vesicles, as described herein, and the loaded vesicles are formulated as a spray or aerosol which can then be applied to a fabric (e.g., an article of clothing made from any naturally-occurring or synthetic fabric as disclosed herein). Thus, in these embodiments, the article of clothing serves as the substrate and antiperspirant-containing and/or fragrance-containing vesicles are formed on the article of clothing. Upon wetting of the fabric, either by perspiration or dousing with water or an aqueous solution, the cargo molecules (e.g., antiperspirant, fragrance) are released from the clothing.

Other compounds such as, for example, sunscreens, insect repellants, antibacterial compounds (to control bacterial odors), humectants (for skin hydration), nicotine and performance-enhancing drugs can also be incorporated into clothing in similar fashion.

In additional embodiments, a spray or aerosol in which the vesicles contain a fragrance and/or an antiperspirant can be sprayed onto the skin of a subject wherein, upon perspiration, vesicles are released and deliver the fragrance and/or antiperspirant.

Additional Applications

Cellulose and nanocellulose can be used in a variety of biomedical and pharmaceutical areas such as, for example, drug delivery, tissue engineering, wound healing, contact lenses, artificial blood vessels, hemodialysis and manufacture of protein-based pharmaceuticals; due to their nontoxicity, biodegradability, structural strength and thermal stability. The ability to deposit vesicles onto these cellulosic and nanocellulosic materials will further expand their utility in these areas. For example, cellulosic bandages can be loaded with vesicles containing analgesic, anesthetic and/or antibiotic compounds. Stents or other intravascular inserts can be coated with vesicles containing anticoagulants, statins or other cholesterol-lowering agents and/or blood pressure medication. The flow of blood causes a fluid shear stress that can transport the vesicles from the stents to clots or other restrictions. Materials used in tissue engineering can be coated with vesicles containing, e.g., growth factors, growth inhibitors, and/or ATP. In addition, because vesicles are similar sizes to cells, vesicles can serve as a mimic to cells to provide contact stimulus or scaffolds.

Vesicles as disclosed herein are self-assembled macromolecular structures useful for encapsulating and controlling the release of cargo, synthesizing proteins (e.g., by cell-free synthesis) and inorganic minerals (e.g., by biomineralization), constructing artificial cells (e.g., red blood cells, building nanoconduits, nanowires, and nanoparticles through bioinspired templating strategies, and elucidating the origins of life through the construction of minimal protocells. Vesicles (e.g., giant liposomes) are also widely used model systems for biochemical and biophysical studies of membrane processes.

EXAMPLES

Example 1: Growth of Vesicles on Cellulose Using Phospholipids

A number of different phospholipid amphiphiles, as shown in Table 1, were used to assemble vesicles on cellulose paper. To this end, 10 μl of a 1 mg/mL solution of the amphiphile in chloroform were deposited on a piece of paper 9.5 mm in diameter. The solvent was allowed to evaporate and then the paper was desiccated under vacuum for 1 hour, to remove traces of residual solvent. The lipid-coated paper was then placed into an aqueous "growth buffer" at room temperature. The choice of growth buffer was determined by the purpose of the experiment. For example, to obtain vesicles of higher density than the surrounding solution, the vesicles were grown in a solution of 100 mM sucrose. Other buffers that can be used include commonly used ionic buffers such as TBS (Tris buffered saline), HEPES 4-(2-Hydroxyethyl)piperazine-1-ethanesulfonic acid, or PBS (phosphate buffered saline). Vesicles were detached from the fiber by applying fluid shear flow, e.g., by using a pipette to aspirate perpendicular to the surface of the paper. The vesicles can be released in the same buffer in which they are grown; or can be released in a different buffer. For example, to produce vesicles with a higher density than the surrounding solution, the vesicles were released in a solution of 100 mM glucose or Ficoll.

For vesicles prepared from the saturated lipid 1,2-dipalmitoyl-sn-glycero-3-phosphocholine (DPPC) and the lipid mixture ESM:DOPC:Chol:TopFluor-Cholesterol:Rhodamine-DPPE, the temperature of the growth buffer was 65° C., and growth was conducted for 90 minutes.

TABLE 1

Lipid mixtures used for vesicle assembly

| Lipids | Ratio | Phase identity* | $T_t$# |
|---|---|---|---|
| DOPC:TopFluor-Cholesterol | 99:1 | $L_d$ | −20 |
| DOPC:Rhodamine-DPPE | 99.5:0.5 | $L_d$ | −20 |
| ESM:DOPC:Chol:TopFluor-Cholesterol:Rhodamine-DPPE | 54.8:20:25:0.1:0.1 | $L_o/L_d$ | ~55 |
| DPPC:TopFluor PC | 99:1 | $S_o$ | ~45 |
| DOPS: DOPC:TopFluor-Cholesterol | 50:49:1 | $L_d$ | −11 |
| POPG:TopFluor-Cholesterol | 99:1 | $L_d$ | −2 |
| DOTAP:TopFluor-Cholesterol | 99:1 | $L_d$ | <5 |

*at 23° C.;
#Transition temperature in ° C.

Example 2: Growth of Oleic Acid Vesicles on Cellulose

Figure 1:
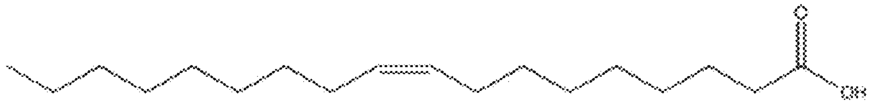
FIG. 1 shows the structure of the lipid oleic acid.
Figure 1:
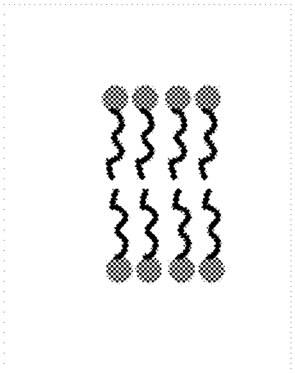

Oleic acid has the structure $CH_3(CH_2)_7CH{=}CH{-}(CH_2)_7{-}COOH$ and a molecular weight of 282.46. FIG. 1. Oleic acid is a relatively simple amphiphile, consisting of a single hydrophobic alkyl chain of 18 carbon atoms (with an unsaturated bond at C9) and a hydrophilic carboxylic acid head group. Amphiphiles with single alkyl chains typically form micelles, (which are compact lipid aggregates, about 80-100 nm in diameter, that do not have an aqueous lumen enclosed by the lipids) since their molecular geometries lead to packing parameters that are less than one (which does not favor the formation of lamellar phases and vesicles). Therefore, micelles cannot enclose hydrophilic cargo. By contrast, vesicles enclose an aqueous hydrophilic lumen, and their diameters can range in size from hundreds of nanometers to hundreds of micrometers. Accordingly, it was of interest to determine if a single alky chain amphiphile, such as oleic acid, could be induced to form vesicles.

As a substrate, a piece of Whatman Grade 42 filter paper was cut into a rough circle approximately 15 mm in diameter. Oleic acid was dispersed in chloroform to nominal surface concentrations of 0.3, 3.0 and 6.0 nmol/mm$^2$ (assuming a diameter of 12 mm), along with 0.5 mol % Nile Red to serve as a fluorescent indicator for membranes. Ten μl of each oleic acid solution was deposited into the center of a filter paper circle, and the paper was placed in a vacuum chamber for 60 min. The dried paper was then affixed to a chamber, which was inserted into a well containing 1 ml of growth buffer (0.2M Bicine/0.25M sucrose/1 mM sodium oleate, pH 8.5) such that the amphiphile-coated region of the paper was completely submerged in the growth buffer. Oleic acid-coated paper was incubated in growth buffer for 90 min., then the chamber was removed from growth buffer, placed into an empty well, and 0.6 ml of extraction buffer (0.2M Bicine/0.25M glucose/1 mM sodium oleate, pH 8.5) was poured through the paper. All procedures were performed at room temperature.

Analysis of the cellulose paper after coating with oleic acid at nominal surface concentrations of 0.3, 3.0 and 6.0 nmol/mm$^2$ and incubation in growth buffer for 90 min was conducted by confocal laser scanning microscopy of the coated paper after excitation of Nile Red fluorescence with a 561 nm diode laser Cellulose paper that had been coated with 0.3 nmol/mm$^2$ oleic acid did not appear to have vesicles growing on the paper. However, after coating with oleic acid at a nominal surface concentration of 3.0 nmol/mm$^2$, numerous fatty acid vesicles were observed growing on the paper. In addition to vesicles, fatty acid droplets and multivesicular structures were also observed. Coating the paper with a nominal surface concentration of 6.0 nmol oleic acid/mm$^2$ resulted in formation of a large number of highly fluorescent fatty acid droplets and multi-vesicular structures.

Samples were extracted from the paper by pipetting a buffered glucose solution across the paper, to cause fluid shear, and the samples were observed by confocal microscopy. Samples extracted from paper that had been coated with a nominal surface concentration of 3.0 nmol oleic acid/mm$^2$ contained many spherical vesicles having thin, uniformly-fluorescent membranes, which distinguished the vesicles from droplets, aggregates and other structures. Samples extracted from paper that had been coated with a nominal surface concentration of 6.0 nmol oleic acid/mm$^2$ and higher were dominated by fatty acid droplets. These results indicate that the fatty acid surface concentration is important for obtaining relatively homogeneous populations of fatty acid vesicles from cellulose fibers. Nominal surface concentrations of 1-3 nmol/mm$^2$ produced optimal results, yielding large numbers of homogeneous vesicles.

Further characterization of the population of vesicles obtained from cellulose paper coated with a nominal surface concentration of 3 nmol/mm$^2$ oleic acid indicated that, among vesicles with a diameter greater than 5 μm (the lower limit at which vesicles could be distinguished from other structures), 70% had a diameter between 5-10 μm, and approximately 20% had a diameter between 10-15 μm. In addition, multilamellar (bi- and trilamellar) vesicles with concentric membranes were observed. Analysis of vesicle fluorescence intensities indicated that vesicle samples were made up of approximately 66% unilamellar vesicles, 24% bilamellar vesicles, and 9% trilamellar vesicles; with a very small percentage of the sample containing vesicles with more than three concentric membranes.

Example 3: Growth of Vesicles on Cellulose Using Diblock Copolymers

The diblock copolymers poly(butadiene-b-ethylene oxide) ($PBD_mPEO_n$) are a family of synthetic long-chain polymeric amphiphiles with a hydrophobic polybutadiene block covalently bonded to a hydrophilic poly(ethylene oxide) block. With suitable values of m and n, the packing parameter of $PBD_mPEO_n$ can be adjusted to favor formation of vesicles, known as polymersomes. Diblock polymers, due to their large molecular numbers ($M_n$s), form bilayer membranes with larger thickness than bilayer membranes formed from phospholipids. The high degree of chain entanglement of PBD blocks results in formation of mechanically robust membranes, with permeabilities that are lower that the permeabilities of membranes formed from phospholipids.

Figure 2:
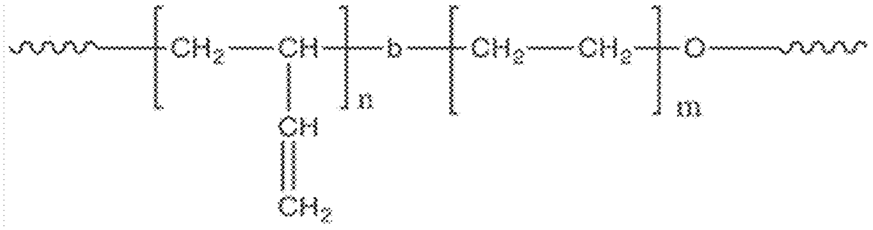
FIG. 2 shows the structure of the diblock copolymer $PBD_{46}PEO_{30}$.
Figure 2:
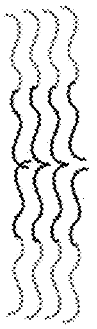

$PBD_{46}PEO_{30}$ ($M_n$~3900, FIG. 2) was dissolved in chloroform, along with 0.5 mol % Nile Red at nominal surface concentrations of 0.02, 0.2 and 2.0 nmol/mm$^2$. Vesicle growth and extraction were conducted as described in Example 2, except that growth buffer was 0.25M sucrose and growth was conducted at 80° C.

Analysis of the cellulose paper after coating with $PBD_{46}PEO_{30}$ at nominal surface concentrations of 0.02, 0.2 and 2.0 nmol/mm$^2$, and incubation in growth buffer for 90 min at 80° C., was conducted by confocal laser scanning microscopy of the coated paper after excitation of Nile Red fluorescence with a 561 nm diode laser. Cellulose paper that had been coated with 0.02 nmol/mm$^2$ $PBD_{46}PEO_{30}$ contained only unvesiculated polymer attached to the fibers, but no polymersomes. Paper coated with $PBD_{46}PEO_{30}$ at a nominal surface concentration of 0.2 nmol/mm$^2$ contained numerous vesicles (polymersomes) with minimal residual polymer adhering to the cellulose fibers. Paper coated with $PBD_{46}PEO_{30}$ at a nominal surface concentration of 2.0 nmol/mm$^2$ contained, along with polymersomes, large aggregates of the polymer coating the fibers. A nominal surface concentration between 0.1-0.6 nmol/mm$^2$ was found to be optimal for forming polymersomes with $PBD_{46}PEO_{30}$.

Polymersomes were extracted from $PBD_{46}PEO_{30}$-coated cellulose using the same extraction method described in Example 2 and observed by confocal microscopy. The size distribution of polymersomes extracted from $PBD_{46}PEO_{30}$-coated cellulose remained narrow (median 9 μm diameter) over a range of $PBD_{46}PEO_{30}$ concentrations from 0.1-2.0 nmol/mm$^2$. Analysis of mean fluorescence intensity of the membranes of polymersomes that had been extracted from cellulose coated with a nominal surface concentration of 0.2 nmol/mm$^2$ $PBD_{46}PEO_{30}$ indicated that approximately 96% of the polymersomes were unilamellar and approximately 4% were bilamellar. Fluorescence leakage assays, using the pore-forming protein α-hemolysin were consistent with a population containing a majority of unilamellar polymersomes. Polymersomes prepared using nominal surface concentrations of $PBD_{46}PEO_{30}$ between 0.1 and 0.6 nmol/mm$^2$ produced similar results.

$PBD_{46}PEO_{30}$ polymersomes can also be produced at lower temperatures, but growth is slower. Incubation of $PBD_{46}PEO_{30}$-coated cellulose paper in 0.25 M sucrose growth buffer for 12 hours at room temperature produced results comparable those obtained from a 90 minute incubation at 80° C.

Example 4: Temporally Decoupled Loading of Polymersomes with Proteins

The requirement for high temperature for rapid growth of $PBD_{46}PEO_{30}$ polymersomes would appear to preclude the use of $PBD_{46}PEO_{30}$ polymersomes for encapsulating temperature-labile cargo molecules such as proteins and other biological molecules. In this example, a method in which high-temperature growth of $PBD_{46}PEO_{30}$ polymersomes is temporally uncoupled from encapsulation of cargo by $PBD_{46}PEO_{30}$ polymersomes is described. Briefly, polymersomes were rapidly grown at high temperature, leading to deposition, onto the cellulose, of polymersomes having unsealed membranes. Cooling allowed the membranes to remain unsealed, as long as the polymersomes remained attached to the cellulose. The unsealed membrane allows membrane-impermeable molecules and charged molecules to diffuse into the lumen of the polymersome along a concentration gradient. Extraction of the polymersomes from the cellulose into bulk solvent seals the membranes, trapping the cargo molecule in the lumen.

$PBD_{46}PEO_{30}$ polymersomes were grown and labeled with Nile Red (in a microtiter well) as described in Example 2 except that vesicle growth was conducted in 0.25M sucrose for 60 min at 80° C. using Whatman Grade 42 filter paper coated with a nominal surface concentration of 0.2 nmol/mm$^2$ $PBD_{46}PEO_{30}$. The samples were then cooled to room temperature and 20×PBS was added to bring the ionic strength to physiological conditions (1×PBS). The coated cellulose was then removed from the well, and 40 μl of fluorescein isothiocyanate (FITC)-conjugated bovine serum albumin (BSA) (2.5 mg/ml in PBS) was added to the well and mixed to obtain a final concentration of 1.5 μM FITC-BSA. The diffusion constant, D, of BSA is approximately $6\times10^{-11}$ m$^2$/sec. Thus, for polymersomes with a diameter, x, of 10 μm, the characteristic time for diffusion, t, is $x^2/D$, or approximately 2 sec. The coated cellulose was then returned to the well and incubated at room temperature for one hour, providing ample time for diffusion; after which one ml of 0.25 M glucose in 1×PBS was used to extract the polymersomes from the cellulose. The polymersome-containing suspension was subjected to centrifugation at 5,000 rpm for 20 min in a 2-ml microcentrifuge tube. The bottom 100 μl was removed, resuspended in 0.9 ml fresh glucose/PBS and centrifuged again at 5,000 rpm for 20 min in a 2-ml microcentrifuge tube. The centrifugation/resuspension cycle was repeated twice more, and, after the final centrifugation, the bottom 40 μl was removed and transferred to an imaging chamber composed of two glass cover slips adhered to each other by a custom-cut gasket of double-sided cellophane tape.

Polymersome loading was quantitated by confocal microscopy, using Nile Red fluorescence to locate the boundaries of polymersomes, and FITC fluorescence to identify the BSA cargo protein. FITC fluorescence was excited with the 488 nm laser line of an argon laser, and mean intensity of FITC fluorescence, inside polymersome boundaries, was determined. The majority of polymersomes obtained by the process described in this example contained strong FITC fluorescence within their lumens, demonstrating successful encapsulation of BSA. Quantitative analyses showed that only about 20% of polymersomes had FITC intensities within the lowest 10% of the fluorescence intensity distribution.

These results show that a simple, diffusion-controlled bench-top process, using a single microtiter well in a 24-well plate, yielded approximately $2\times10^4$ loaded polymersomes within about two hours. The process can be scaled up either by parallelization or by increasing the area of the cellulose and the concentrations and volumes of the coating materials and cargo.

Example 5: Growth of Vesicles on Cellulose Using Triblock Copolymers

Figure 3:
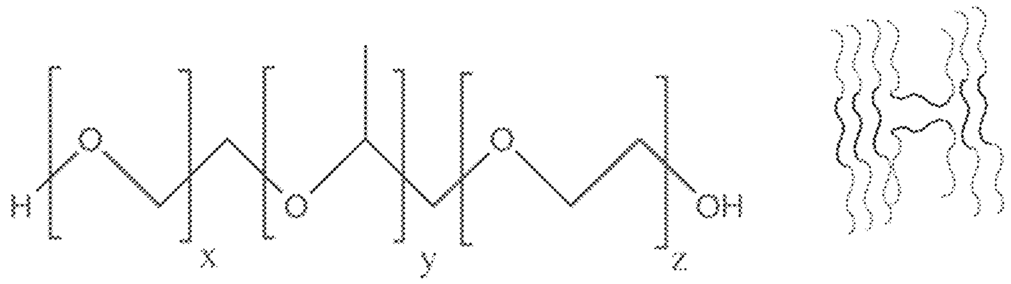
FIG. 3 shows the structure of the triblock copolymer polyoxyethylene-polyoxypropylene-polyoxyethylene ($PEO_5PPO_{67}PEO_5$, trade name Pluronic® L121).

The commercial ABA triblock copolymer polyoxyethylene-polyoxypropylene-polyoxyethylene ($PEO_5PPO_{67}PEO_5$, trade name Pluronic® L121, $M_n$~4400, FIG. 3) forms large polymersomes under limited conditions. It has proven difficult to produce large polymersomes from this polymer due to its low degree of hydrophobicity. Do Nascimento et al. (2016) *Langmuir* 32:5350-5355; Rodriguez-Garcia et al. (2011) *Soft Matter* 7:1532.

To manufacture triblock copolymer-containing vesicles, Pluronic® L121 ($M_n$~4400, FIG. 3) was dissolved in chloroform, along with 0.5 mol % Nile Red, at nominal surface concentrations of 0.6 and 2.0 nmol/mm$^2$. Vesicle growth and extraction were conducted as described in Example 2, except that growth buffer was 0.025M Ficoll 400 (a sucrose polymer with MW~400,000).

The size distribution of polymersomes extracted (same extraction method as described in Example 2) from cellulose coated with Pluronic® L121 at a nominal surface concentration of 0.6 nmol/mm$^2$ was examined by confocal fluorescence microscopy after excitation of Nile Red fluorescence. Among the clearly identified polymersome structures having a diameter greater than 5 μm, 95% had a diameter between 5-10 μm, and approximately 4% were between 10-15 μm in diameter. Analysis of mean fluorescence intensity of the membranes indicated that the polymersomes were predominantly unilamellar.

Polymersomes made from Pluronic® L121 formed optimally on cellulose at a nominal surface concentration between 0.6 and 1 nmol/mm$^2$ at room temperature.

Example 6: Formation of Vesicles on Cellulose Fibers

Previous examples have described formation and growth of vesicles on cellulose paper. In this example, vesicles were assembled on a different form of cellulose, namely cotton; and properties of vesicles assembled on paper and cotton were compared. Both filter paper and cotton fabric are manufactured from cellulose fibers that are obtained from bolls that form around the seeds of the cotton plant (*Gossypium* sp.)[39]. Cellulose fibers from cotton bolls are the highest purity natural source of α-cellulose[39], and is a commodity scale renewable raw material[40]. High purity filter papers consist of cellulose fibers of approximately 1.5 mm-6 mm in length obtained from the short fibers attached to the cotton seed (cotton linters). These short fibers entangle during the papermaking process to form a disordered randomly percolated network[41].

Cotton fabric, also composed of cellulose fibers, has a radically different microstructure than paper. The cellulose fibers used to make cotton fabric are obtained from the staple fibers of the cotton boll[39]. These fibers have lengths of 20 mm or longer and can reach lengths of up to 40 mm[39]. Hundreds of these long cellulose fibers are spun into tightly twisted bundles to form yarn[39]. The yarn is then woven to form an interlaced network[39]. Depending on the weave pattern, the process leaves regular windows of low to no cellulose content between the orthogonal bundles of yarn. Thus, the cellulose fibers in fabric are highly ordered rather than randomly entangled such as those in paper.

Materials

Whatman® Grade 41 Filtration paper, Whatman® Grade 1 Filtration paper, Whatman® Ashless Grade 42 Filtration Paper, glass microscope slides (Thermo Scientific™) and glass cover slips (No. 1 thickness, Thermo Scientific™) were obtained from Thermo Fisher Scientific (Waltham, MA). Unbleached cotton fabric composed of 100% organic cotton was obtained from Amazon Inc. (Organic Cotton Plus (Lubbock, Texas)).

Chemicals

Sucrose (BioXtra Grade, purity≥99.5%), glucose (BioXtra grade, purity≥99.5%) and casein from bovine milk (BioReagent grade) were obtained from Sigma-Aldrich (St. Louis, MO). Chloroform, with 0.75% ethanol as preservative, (ACS grade, purity≥99.8%) was obtained from Thermo Fisher Scientific. Ultrapure water (18.2 MΩ) was obtained using an ELGA Pure-lab Ultra water purification system (Woodridge, IL). 1,2-dioleoyl-sn-glycero-3-phosphocholine (18:1 (Δ9-Cis) PC (DOPC)) and 1-palmitoyl-2-(dipyrrometheneboron difluoride)undecanoyl-sn-glycero-3-phosphocholine (TopFluor®-PC) were obtained from Avanti Polar Lipids, Inc. (Alabaster, AL).

Preparation of Substrates

Cotton fabric, obtained commercially as described above, was cleaned with the non-polar solvent chloroform and the polar solvent ultrapure water to remove non-polar and polar impurities, which might have attached to the fabric during the processes of manufacture and transport. A 10 cm×10 cm piece of cotton fabric was soaked in 50 mL of neat chloroform for 30 minutes. After 30 minutes, the chloroform was discarded and the process repeated. The chloroform was allowed to evaporate and then the fabric was alternately rinsed and soaked in an excess of ultrapure water over the course of 3 hours. After the final rinse, the fabric was dried at ambient temperature.

Laboratory grade filter paper is certified by the manufacturer to be free of impurities. Nonetheless, for consistency with the treatment of the fabric, filter paper was soaked in chloroform for 30 minutes; after which the chloroform was discarded and the process repeated. The chloroform was allowed to evaporate and the paper was then soaked in water for 30 minutes. Due to the low wet strength of the paper, it was soaked in water for only 30 minutes with no agitation, compared to the three-hour soak to which the cotton fabric was subjected. The paper was then dried at ambient temperature. To obtain consistently sized substrates, circular disks of 9.5 mm diameter were punched from the papers using a paper punch (EK Tools Circle Punch, ⅜-Inch). Similar sized pieces of fabric were cut with a pair of scissors.

Growth of GUVs

A 99.5:0.5 mol % solution of DOPC:TopFluor-PC was prepared in neat chloroform at a concentration of 2 mg/mL. Growth conditions were standardized by depositing appropriate volumes of the lipid solution to obtain 3 μg of lipid per 1 mg of cellulose (lipid/cellulose mole ratio~7×10$^4$) on the substrates. The small volume of solvent (10-20 μL) evaporated rapidly. The lipid-coated substrates were then placed in a standard vacuum desiccator for one hour to remove traces of solvent. To grow GUVs, the dry lipid-coated substrates were placed into a 2-mL microcentrifuge tube (e.g., Eppendorf), to which was then added 500 μL of an aqueous solution of sucrose at a concentration of 100 mM, and the tubes were incubated for 60 minutes.

Coverslip-Assisted Harvesting of GUVs

A 100-μL droplet of a 100 mm aqueous solution of sucrose was placed on a glass coverslip. Lipid-coated substrate, prepared as described in the previous paragraph, was transferred into the droplet using forceps. Water remained trapped in the hydrophilic porous cellulose substrates during the transfer, preserving the GUVs. GUVs were harvested by gently aspirating the solution with a cut pipette tip, taking care to avoid touching the surface of the substrate. Suspensions of harvested GUVs, in 100 μL aliquots, were transferred to a clean microcentrifuge tube for storage until use. High and consistent yields of GUVs were obtained in the form of concentrated suspensions, which can be diluted as needed. This method of harvesting differs from the previously-described method involving gravity-induced flow of 1 mL of buffer through filter paper supported on polystyrene well inserts in 24-well plates. Kresse et al. (2016) *Appl. Mater. Interfaces* 8:32102-32107.

Confocal Microscopy and Image Analysis of GUVs

Imaging chambers were constructed by covalently bonding custom-made PDMS gaskets with a square opening (width×length×height=5×5×1 mm) to glass microscope slides. Before use, a chamber was passivated with a solution of 1 mg/mL casein to prevent rupture of the GUVs on the bare glass. Faysal et al. (2017) PLoS One 12:No. e0169487. The passivated chamber was filled with 25 μL of an isomolar solution of glucose, then a 5-μL aliquot of the suspension of harvested GUVs was added. GUVs were allowed to sediment for 3 hours before imaging. Images were captured using an upright confocal laser-scanning microscope (LSM 880, Axio Imager.Z2m, Zeiss, Germany). The TopFluor® dye (Avanti, Alabaster, AL) was excited with a 488 nm argon laser and fluorescence was collected using a 10× Plan- NeoFluar objective with a numerical aperture of 0.3. The entire area of the chamber was imaged using an automated tile scan routine (49 images [850.19 μm×850.19 μm, (2140 pixels×2140 pixels)] with a confocal slice thickness of 13 μm). The routine used an autofocus feature that focused at the plane of the glass slide by locating the plane that reflected laser light maximally. Confocal images were analyzed using a custom MATLAB routine (Mathworks Inc., Natick, MA). The routine thresholded the images and then applied a watershed algorithm to segment the fluorescent GUVs from the background. The native regionprops function was used to obtain the equivalent diameters of the segmented objects.

Scanning Electron Microscopy (SEM) of the Dry Substrates and Confocal Microscopy Imaging of the Hydrated Substrates SEM images of the dry cellulose substrates were obtained using a field emission scanning electron microscope (GeminiSEM 500, Zeiss, Germany). The beam accelerating voltage was 1 kV and secondary electrons were collected from the surface of the substrates using an Everhart-Thornley secondary electron detector. Images were captured at a lateral pixel resolution of 1.09 μm/pixel [1120 μm×840 μm (1024×768)]. For imaging of the hydrated substrates, the cellulose fibers were rendered fluorescent with the cellulose dye Direct Red 23 25 and confocal z-stacks were obtained at a lateral pixel resolution of 0.4 μm/pixel [640.17 μm×640.17 μm (1620 pixels×1620 pixels)] and an axial spacing of 35 μm/slice. Bandpass filtered maximum intensity projections of the z-stacks were obtained, and the diameters of the fibers were measured, using ImageJ (NIH, Bethesda, MD).

GUV Growth Cycle Experiments on Cotton Fabric

After harvesting GUVs at the completion of a cycle of growth, fabric was cleaned before the next cycle of growth. For cleaning after a vesicle growth cycle, fabric was rinsed with 10 mL of ultrapure water and then soaked in ultrapure water under agitation for 30 minutes to remove traces of dissolved salts and sugars remaining from the growth buffer. The fabric was then placed in a 65° C. oven for 1 hour to dry. The dry fabric was soaked in neat chloroform under agitation for 30 minutes. Fabric was removed from the chloroform and residual chloroform was allowed to evaporate, then the fabric was placed in a vacuum chamber for 1 hour to remove all traces of chloroform. Fresh lipid was then deposited on the fabric (as described in the section of this example entitled "Growth of GUVs," above) to start the next cycle of growth.

Properties of the Cellulose Substrates

When the papers were visualized by scanning electron microscopy (SEM), the cellulose fibers in the papers appeared as twisted flattened cylinders with diameters of approximately 15-21 μm. G41 paper had large pores between the fibers; while the apparent pores were smaller and fewer in number in images of the G1 and G42 papers. These microstructural differences were consistent with the reported particle retention capacities and flow rates of the filter papers. SEM images of the cotton fabric showed a highly ordered network of twisted cellulose fibers in the yarn with regions devoid of cellulose fibers between the orthogonal strands of yarn.

Since the growth of GUVs occurs in water, the hydrated substrates were characterized using confocal microscopy. Maximum intensity projections of the three-dimensional confocal z-stacks of the substrates were obtained, and a bandpass filter was applied to the images to highlight the edges of the fibers. Using these methods, the average diameter of the fibers, $d_f$, was determined to be 21±5 μm for G41, 20±6 μm for G1, 16±7 μm for G42, and 16±4 μm for cotton fabric. Thus, G41 and G1 paper have, on average, larger diameter fibers, while G42 paper and the cotton fabric have smaller diameter cellulose fibers.

The Sizes of the GUVs are Bounded by the Average Diameter of the Cellulose Fibers Confocal images of the GUVs harvested from the four different substrates were obtained. Qualitatively, the GUVs appeared similar.

Figure 4:
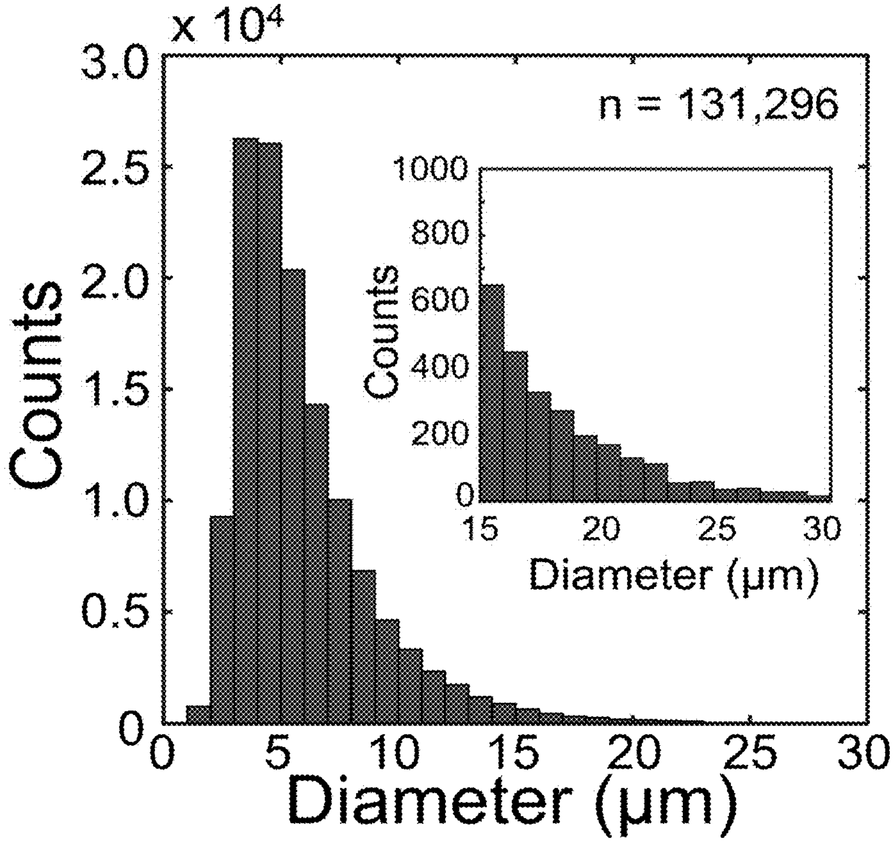
FIG. 4 shows a histogram of vesicle diameters for vesicles made on cotton fabric. The inset shows a zoomed view of a section of the right tail.

The diameters of the GUVs assembled on cotton fabric were quantified using a custom MATLAB image analysis routine. A histogram of the diameters revealed that the distribution of GUV diameters was skewed, with a single well-defined peak and right tail (FIG. 4). In this histogram, n=131,296, and the bin widths are 1 μm. The inset shows a zoomed view of a section of the right tail. Skewed distribution of vesicle sizes obtained through a different technique, gentle hydration of lamellar phospholipid stacks on glass, has been observed previously[13]. Histograms of GUV sizes obtained through electroformation[44-47] and gel-assisted hydration[21,23,24,48] also reveal a right-tailed distribution. Without wishing to be bound by theory, it is possible that skewed distribution of sizes is an intrinsic property of GUVs produced through methods that rely on the vesiculation of lamellar phospholipid stacks (i.e. electroformation, gel-assisted hydration, and cellulose-abetted hydration). Unlike a normal distribution, which is symmetric, the mean, median, and mode of a skewed distribution do not coincide. Thus, representing GUV sizes with arithmetic moments, such as the mean and standard deviation, without further qualification, probably does not accurately reflect the true statistical distribution of the population.

Figure 5:
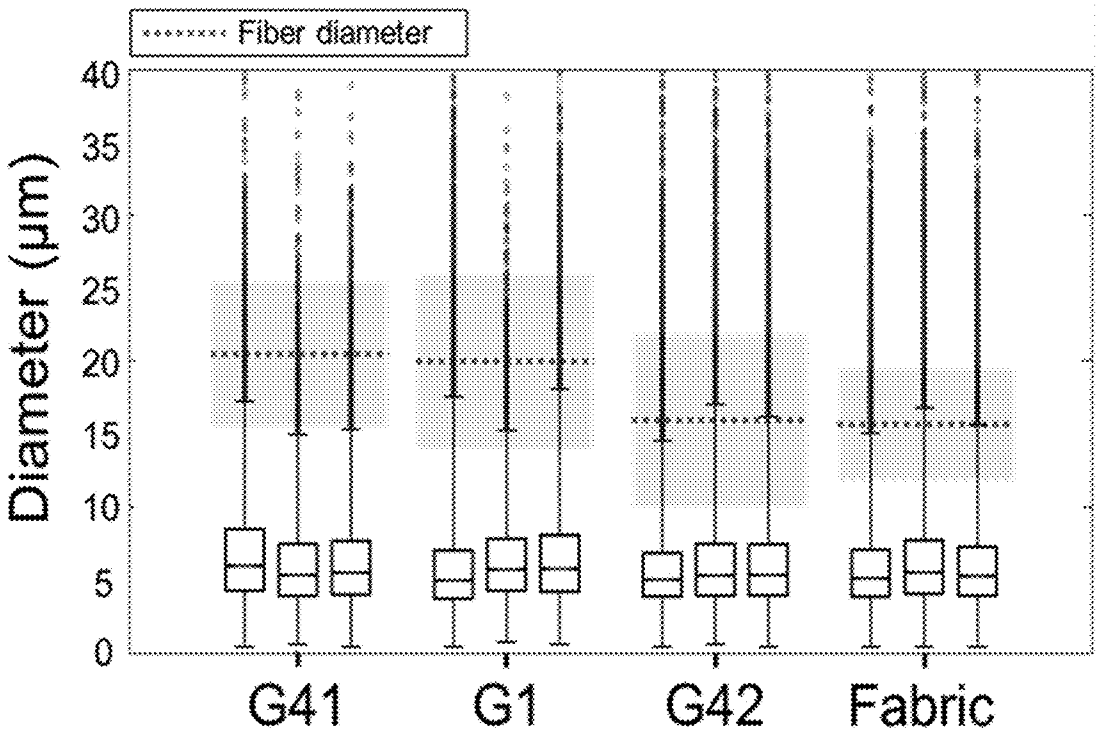
FIG. 5 shows size distributions (expressed as vesicle diameters) for vesicles made on four different types of cellulose: Grade 41 filter paper (G41), Grade 1 filter paper (G1) Grade42 filter paper (G42) and cotton (Fabric).

Size distributions of GUVs assembled on the different substrates were represented as a box and whisker plot to compare the different populations (FIG. 5). The three different boxes shown for each substrate represent three independent experiments performed for each substrate. The lower whisker indicates the minimum size (1 μm so as to include only GUVs and not other structures such as smaller vesicles and lipid nanotubes). The bottom half of the box represents the 25$^{th}$ percentile of the distribution. The line crossing each box indicates the median of the distribution. The top half of the box is the 75$^{th}$ percentile of the distribution. The top whisker indicates the 98$^{th}$ percentile of the GUVs. The dotted lines above the top whisker represent the remaining 2% of the GUVs.

The results of these analyses indicate that sample-to-sample variation in GUV sizes was minimal, and the distribution of GUV sizes was remarkably similar among the three grades of paper and the cotton fabric. The median diameter of the GUVs was between 5 and 6 μm for all four of the substrates, with a mode of 4 μm. Fifty percent of the GUVs had diameters between 4 and 9 μm. From these results, it can be concluded that the microstructure of the cellulose substrates, which varied significantly, does not control the sizes of the GUVs.

As part of this analysis the fiber diameter, $d_f$, of the substrate was plotted as a dashed line crossing the upper whisker in the box plot (FIG. 5). It is apparent that 98% of the GUVs had diameters smaller than the $d_f$ of the substrate upon which they were assembled; with the median diameter of the GUVs being about 25 percent of the average fiber diameter. Although the formation of GUVs with a diameter greater than $d_f$ was statistically rare, due to the high yield of GUVs, approximately 100,000 vesicles (representing approximately 1% of total vesicle number) with diameters ranging from 20-60 μm, in 100-μL suspensions of vesicles assembled on G42 and cotton, were obtained. The distribution of diameters of GUVs on the cellulose fibers prior to harvesting was similar to the distribution of diameters of the harvested GUVs. Longer incubation times, including overnight incubation, did not change the size distribution of the GUVs. From these results, it can be concluded that the diameters of the GUVs are related to the diameter of the cellulose fibers.

Cotton Fabric and G42 Paper Yielded a Larger Number of GUVs

Figure 6:
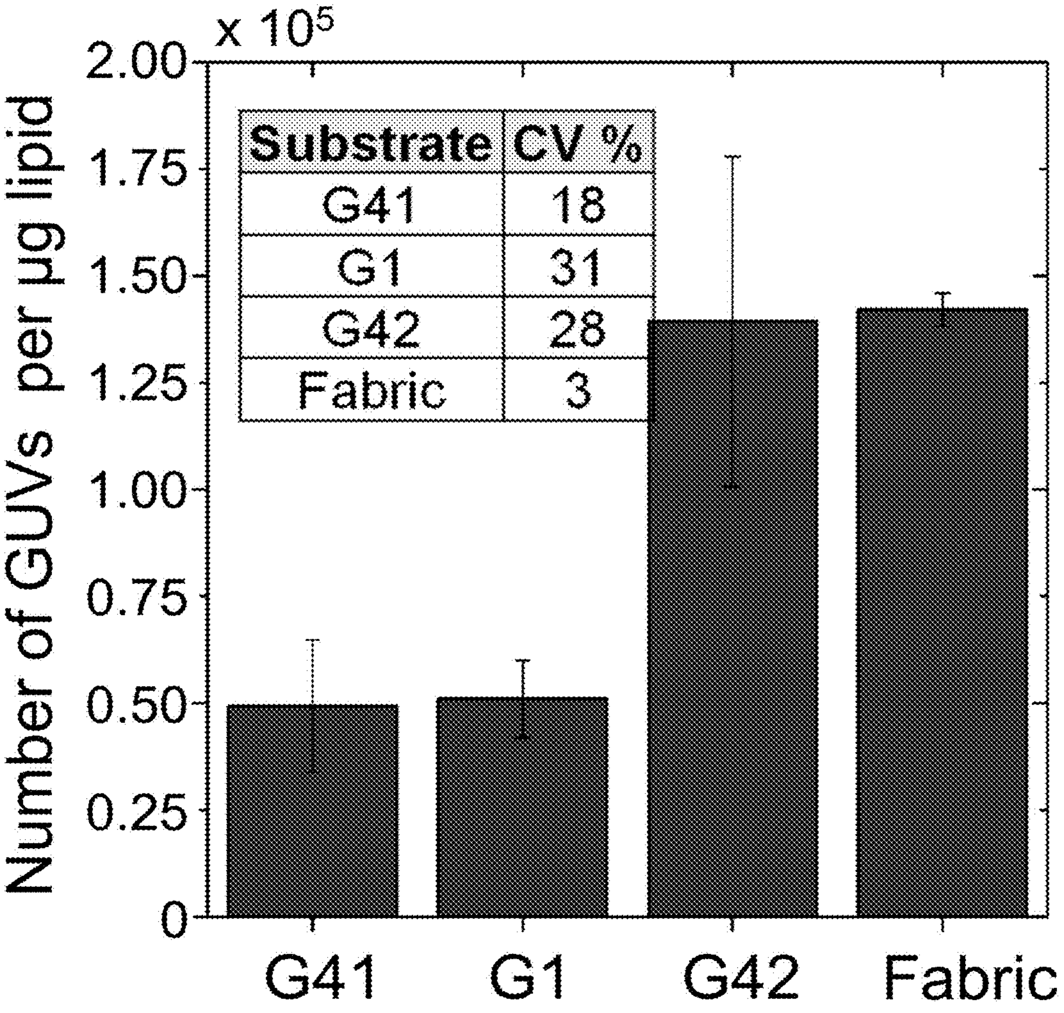
FIG. 6 shows plots of the number of GUVs obtained per microgram of DOPC:TopFluor-PC (lipid) when GUVs were assembled on Grade 41 filter paper (G41), Grade 1 filter paper (G1) Grade42 filter paper (G42) and cotton (Fabric). The inset table provides the coefficient of variation (CV %) for the vesicle number obtained from each of the four substrate samples.

The number of GUVs that were obtained from each substrate was also quantified. To allow comparison between substrates, GUV counts were normalized to the mass of lipid deposited; i.e., the number of GUVs per μg of lipid (DOPC: TopFluor-PC) is reported. The average number of GUVs obtained per μg lipid was similar for GUVs assembled on G41 and G1 paper (FIG. 6). The inset table shows the coefficient of variation, which parameterizes the sample-to-sample variation of GUV yields. The average number of GUVs per microgram of lipid obtained when vesicles were assembled on G42 paper and cotton fabric were similar to each other, and about three times higher than the average number of GUVs obtained from G41 and G1 paper (FIG. 6). Sample-to-sample variation of the number of GUVs harvested from cotton fabric was lower than the sample-to-sample variation of the paper samples (FIG. 6, inset table). This is likely due to the ordered arrangement of cellulose fibers in the fabric. We note that even the lower yielding papers (G41 and G1) exceed the GUV yields reported for electroformation[45].

Compared to G41 and G1 papers, cotton fabric and G42 paper have lower $d_f$. Additionally, G42 paper has a higher particle retention capacity and lower liquid flow rate, reflective of the denser packing of cellulose fibers and smaller pores. Although the cotton fabric contains large windows in which no cellulose is located, between the orthogonal strands of yarn, the cellulose fibers in the yarn were densely packed. Thus, these data suggests that substrates with smaller average fiber diameters and denser packing of cellulose fibers yield a larger number of GUVs per unit mass of lipid.

Cotton Fabric Supports Multiple Cycles of GUV Growth

Paper is an attractive substrate for fabricating GUVs at the laboratory benchtop due to its low cost and disposability. At larger scales, the cost of raw materials, the cost of disposal, and general sustainability, favors reusable substrates. Paper has low wet strength. In contrast, cellulose fabric can withstand repeated mechanical insults such as abrasion and mechanical washing.

Figure 7:
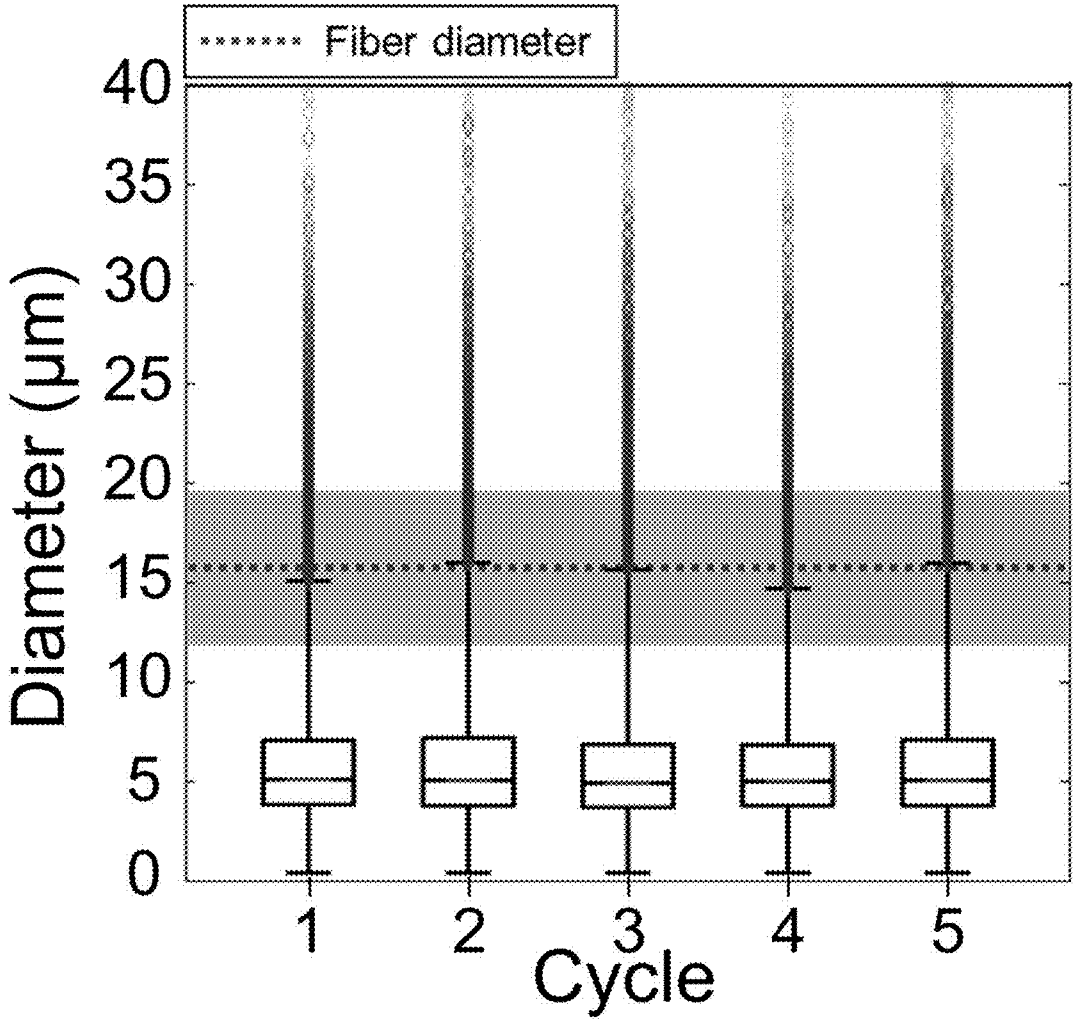
FIG. 7 shows size distributions (expressed as vesicle diameters) for vesicles made on cotton fiber in five sequential cycles of vesicle growth.
Figure 8:
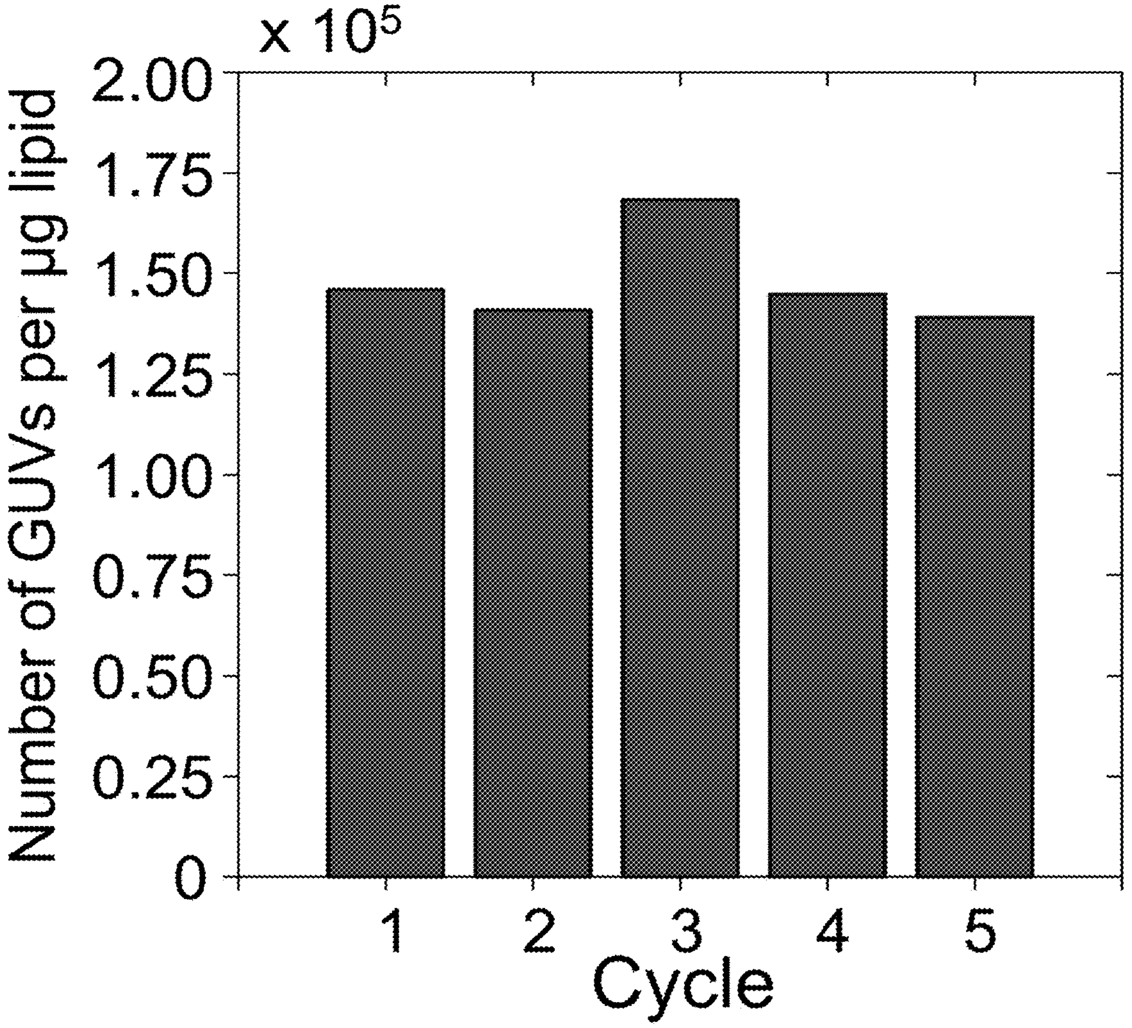
FIG. 8 shows plots of the number of GUVs obtained per microgram of DOPC:TopFluor-PC (lipid) when GUVs were assembled in sequential cycles on cotton fiber.

Therefore, experiments were performed to determine if fabric can support sequential cycles of GUV growth. One cycle of growth consisted of the deposition of lipids, growth for 60 minutes, and then the harvest of the GUVs. Cleaning and drying the fabric after the harvest, and depositing fresh lipids repeated the cycle (see above for detailed procedure). Five cycles were performed on a single piece of fabric. Representative confocal images of GUVs obtained from pristine fabric in the first cycle, and GUVs obtained from the fabric after five cycles showed no differences in vesicle morphology. Quantitative comparisons confirmed that GUV sizes (FIG. 7) and yields (FIG. 8) were similar in each of the five cycles. Other than a slight shrinkage of the yarn, the fabric after the fifth cycle of growth was indistinguishable from fabric imaged after the first cycle of growth. Thus, it is likely that the fabric can support more than 5 cycles of GUV growth.

These experiments indicate that the process of GUV growth does not alter the cellulose fibers as observed by confocal imaging. The cellulose fibers act as a promoter for the rapid formation of GUVs from lamellar phospholipid stacks in aqueous solutions; accelerating the rate of vesiculation of lamellar stacks of phospholipids compared to the rates of vesiculation on glass[13-17] and, as an added benefit, remain unchanged at the end of the process.

Conclusions

All cellulose substrates tested produced populations of GUVs with right-skewed unimodal distributions in diameters. The distribution in sizes was similar among the different substrates and was bounded by the average diameter of the cellulose fibers. GUV yields, however, were different among the substrates; with highest yields obtained using G42 filter paper and cotton fabric, and lowest sample-to-sample variation with cotton fabric. In addition, cotton fabric supports multiple cycles of growth and harvest without any apparent change in the properties of the GUVs produced. These results demonstrate that cotton fabric is a superior substrate for fabricating GUVs due to high yields and minimal sample-to-sample variation, and can be used to grow vesicles, not only from phospholipids as described herein, but also from other lamellar phase forming amphiphiles[26].

Example 7: Formation of Vesicles on Nanofibrillar Cellulose Substrates

Cellulose nanofibrils can obtained from cellulose fibers through mechanical homogenization using shear, pressure, and/or chemical treatments. To obtain cellulose nanofibrils, 60 mL of a 0.7 wt % suspension of nanocellulose in water is casted in a 15 mm diameter petri dish. Li Y-Y et al. (2018). Review of Recent Development on Preparation, Properties, and Applications of Cellulose-Based Functional Materials. *Int J Polym Sci.;* 2018:1-18. doi:10.1155/2018/8973643. The water is allowed to evaporate at room temperature, leaving behind a thin sheet of nanopaper. The nanopaper is rinsed and cleaned thoroughly with chloroform and then water. Alternately commercial tracing paper, which is also mechanically and chemically refined to obtain a dense fibrillar surface, can be used.

To obtain the lipid-coated nanofibrillar cellulose substrate, a 9.5 mm diameter piece of the nanopaper, made as described above, was cut out and then 10 μg of DOPC: TopFluor-PC (99.5:0.5 mol %) in chloroform was deposited onto the surface with a glass syringe. The lipid-coated nanofibrillar cellulose paper was placed in vacuum for 1 hour to drive-off traces of solvent. Upon hydration in 100 microliters of an aqueous solution of 100 mM sucrose, lamellar stacks of amphiphile bilayers formed and vesiculation proceeded over the course of 2 hours. Vesicles were released from the nanofibrillar cellulose surface into the bulk aqueous solution by aspirating the sucrose solution over the nanofibers with a 1000 microliter pipette six times. All experiments were performed at room temperature.

Example 8: Formation of Vesicles on Regenerated Cellulose Membranes

Cellulose can be dissolved using suitable solvents. In the presence of sodium hydroxide, cellulose reacts with carbon disulfide to produce sodium cellulose xanthate. The sodium cellulose xanthate can be extruded into fibers or cast into sheets and, upon neutralization with sulfuric acid ($H_2SO_4$), yields viscose rayon or cellophane. In this example, commercial regenerated cellulose dialysis membranes were used as substrates to form giant vesicles. The membrane was washed for 15 minutes with ultrapure water, for 30 minutes in 10 mM EDTA, for 30 minutes in 10 mM $NaHCO_3$ at 80° C. and again for 15 minutes in ultrapure water. To obtain lipid-coated regenerated cellulose membranes, a 9.5 mm diameter piece of regenerated cellulose membrane was cut and then 10 µg of 1,2-dioleoyl-sn-glycero-3-phosphocholine (DOPC) in chloroform was spread onto the surface with a syringe. The lipid-coated regenerated cellulose membrane was placed in vacuum for 1 hour to drive-off traces of solvent. Upon hydration, the formation of bilayers was immediate and vesiculation proceeded over the course of 2 hours. Fluid shear applied with a pipette released the vesicles from the membrane into the bulk aqueous solution.

Example 9: Formation of Vesicles on Silk Fabric, Nylon Fabric, Polyester Fabric and Rayon Fabric The silk and nylon fabrics were both coated with 50 µg DOPC lipid in isopropanol. The polyester fabric was coated with 100 µg DOPC lipid in isopropanol. Trace isopropanol was allowed to evaporate in a vacuum for 1 hour. The coated fabrics were then hydrated in aqueous buffer for 1 hour, and vesicles were released from the fabric by applying fluid shear with a pipette.

Table 2 shows the molecular structure, the average fiber sizes, the weave pattern, and the moisture regain values of, silk, wool, cotton, rayon, nylon, polyester, and fiberglass. Moisture regain is the amount of water a completely dry fiber will absorb from the atmosphere at a standard temperature of 21° C. and at a relative humidity of 65%. Tabulated values are expressed as a percent of the dry fiber weight. Moisture regain is a proxy for the hydrophilicity or affinity for water of textiles. The regain likely also depends on the microstructure and the specific surface area of the fibers in these microstructurally complicated fibrous porous media. See also Cook, J. G. Handbook of Textile Fibres: Natural Fibres, 5th ed.; Woodhead Publishing: Cambridge, UK, 1984 and Cook, J. G. Handbook of Textile Fibres: Man-Made Fibres, 5th ed.; Woodhead Publishing: Cambridge, UK, 1984.

Figure 10:
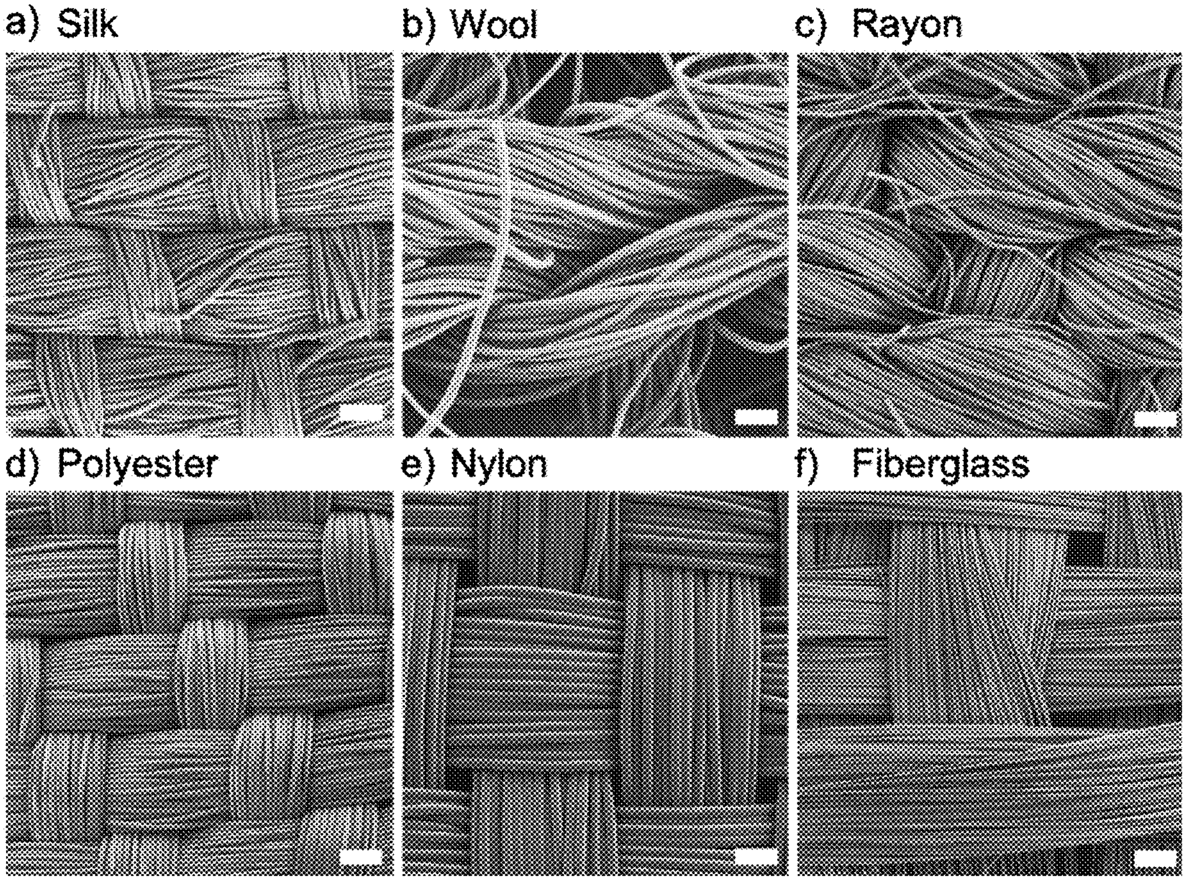
FIGS. 10*a-f* show scanning electron micrographs of fabrics used for growth of vesicles.

FIG. 10 shows scanning electron microscope images of the fabrics. The silk (FIG. 10*a*), rayon (FIG. 10*c*), polyester (FIG. 10*d*), nylon (FIG. 10*e*), and fiberglass (FIG. 10*f*) fabrics had regularly arrayed cylindrical fibers with smooth surfaces. Furthermore, the rayon (FIG. 10*c*), polyester (FIG. 10*d*), nylon (FIG. 10*e*) and fiberglass (FIG. 10*f*) fibers appeared very uniform, reflective of their man-made nature. Although cylindrical, wool (FIG. 10*b*) had a scaly surface and the arrangement of the fibers in the fabric was less regular.

TABLE 2

Properties of fabrics*

| Fabric | Chemical Formula | Fiber diameter, µm (mean ± sd) | Moisture Regain (%) | Fabric Weave |
|---|---|---|---|---|
| Natural | | | | |
| Silk | 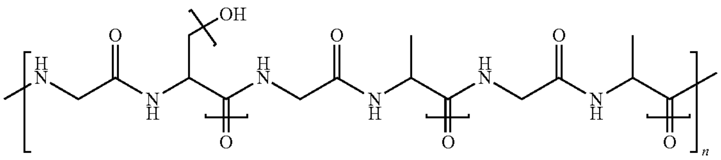 | 10.6 ± 1.7 | 11 | Plain |
| Wool | 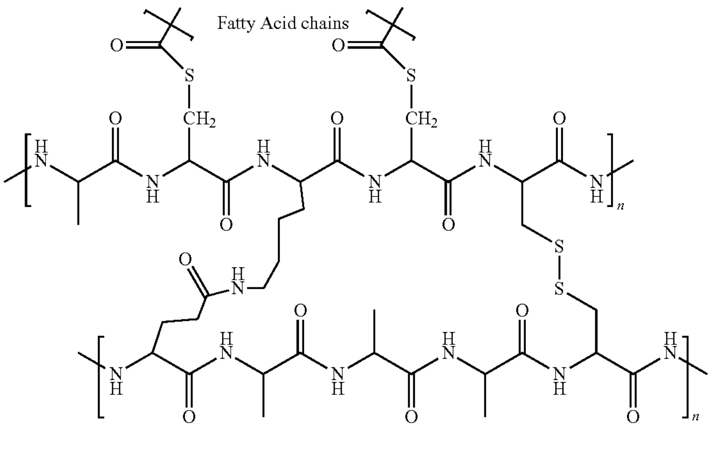 | 18.5 ± 4.8 | 16 | Jersey |

TABLE 2-continued

Properties of fabrics*

| Fabric | Chemical Formula | Fiber diameter, µm (mean ± sd) | Moisture Regain (%) | Fabric Weave |
|---|---|---|---|---|
| Cotton | 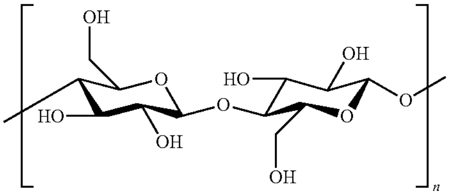 | 15.8 ± 3.7 | 8.5 | Plain |
| Semisynthetic | | | | |
| Rayon | 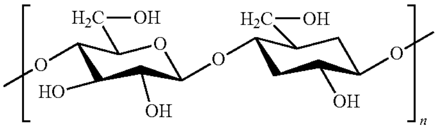 | 12.0 ± 1.5 | 11 | Plain |
| Synthetic | | | | |
| Nylon | 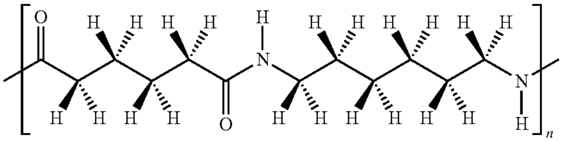 | 22.9 ± 1.3 | 4.0-4.5 | Plain |
| Polyester | 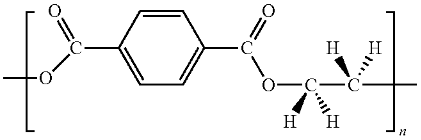 | 12.8 ± 1.4 | 0.4 | Twill |
| Inorganic | | | | |
| Fiberglass (alumino-borosilicate) | 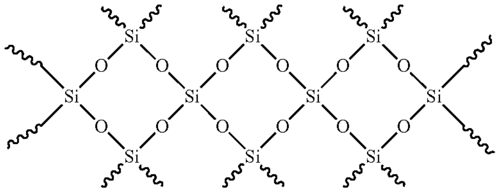 | 4.7 ± 0.4 | — | Satin |

*Values for moisture regain are from Cook, J. G. *Handbook of Textile Fibres: Natural Fibres*, 5th ed.; Woodhead Publishing: Cambridge, UK, 1984 and Cook, J. G. *Handbook of Textile Fibres: Man-made Fibres*, 5th ed.; Woodhead Publishing: Cambridge, UK, 1984. . Fiber diameters were obtained from SEM images.

Example 10: Formation of Vesicles on Silk Fabric

Silk is a natural protein-based fiber. Cocoons of the silkworm *Bombyx mori* are the primary source of commercial silk. Silk fibers are composed of the insoluble protein fibroin. The molecular structure of silk is rich in hydrophilic amide groups (Table 2). Silk has a moisture regain of 8.5% indicating its hydrophilic nature. See, for example, Cook, J. G. *Handbook of Textile Fibres: Natural Fibres,* 5th ed.; Woodhead Publishing: Cambridge, UK, 1984.

Silk (Silk Dupioni, Bright White, 100% silk) was obtained from a local craft store (JoAnn, LLC, Merced, CA). The fabric was cut into 10 cm×10 cm squares. Two fabric squares were placed in a 100 ml glass media bottle containing 100 ml of chloroform (neat) and the contents of the bottle were stirred for 30 min using a magnetic stirrer and a Teflon® stir bar. The process was repeated twice, using fresh chloroform each time; after which the fabric was removed from the bottle and the chloroform allowed to evaporate from the fabric. The fabric squares were then placed into a 1 liter glass media bottle containing 1 liter of ultrapure water. Alternate cycles of soaking and rinsing in water were continued for 3 hours. Fabric squares were then allowed to dry under ambient conditions and stored in clean plastic petri dishes.

For lipid deposition and vesicle (GUV) formation, a 2 mg/ml solution of DOPC:TopFluor-PC (99.5:0.5 mole %) was prepared in chloroform (neat). For this example and Examples 11-15; 1,2-dioleoyl-sn-glycero-3-phosphocholine (18:1 (Δ9-cis) PC (DOPC) and 1-palmitoyl-2-(dipyrrometheneboron difluoride) undecanoyl-sn-glycero-3-phosphocholine (TopFluor-PC) were obtained from Avanti Polar Lipids. Discs of fabric with a diameter of 9.5 mm were cut from the cleaned, dried fabric squares. Lipid solution was deposited on the discs to provide a concentration of 3 µg lipid solution per milligram of fabric substrate. The deposited liquid was allowed to evaporate under ambient conditions, and the dried fabric was then placed in a vacuum chamber for one hour to drive off residual solvent. The fabric discs were then removed from the vacuum and each disc was placed in a microcentrifuge tube to which was added 0.5 ml of sucrose (100 mM in water) after which the tubes were incubated for one hour under ambient conditions to allow vesicle growth.

To harvest vesicles, a 0.1 ml droplet of 100 mM sucrose in water (BioXtra Grade, purity >99.5%, Sigma-Aldrich, St. Louis, MO) was placed on a clean glass cover slip; and the fabric was removed from the microcentrifuge tube and quickly immersed in the droplet. Vesicles were harvested by gently aspirating the droplet into a 1 ml micropipette tip while moving the tip (whose opening had been enlarged by cutting off the end of the tip) systematically over the surface of the fabric disc.

Images of the dry fabrics were obtained by scanning electron microscopy (SEM) using a GeminiSEM 500 field emission scanning electron microscope (Zeiss) with a beam accelerating voltage of 1 kV. Secondary electrons were collected from the surface of the fabric substrate using an Everhart-Thomley secondary electron detector.

For confocal imaging, square imaging chambers (6 mm wide×6 mm long×1 mm high) were fabricated from polydimethylsiloxane (PDMS) bonded onto glass microscope slides. The surfaces of the chamber were passivated with casein (BioReagent grade from bovine milk, Sigma-Aldrich, St. Louis, MO) to prevent rupture of vesicles during imaging and preparation for imaging. Glucose (56 μl of a 100 mM aqueous solution) (BioXtra Grade, purity >99.5%, Sigma-Aldrich, St. Louis, MO) was placed in the chamber and a 4 μl aliquot of harvested vesicle solution was added to the glucose solution. After 3 hours (during which time the sucrose-filled vesicles sedimented to the bottom of the chamber due to their higher density) an upright confocal laser scanning microscope (Zeiss LSM 880 with Airyscan+ FAST, Axio Imager.Z2m) was used to capture single-plane confocal images of the entire area of the chamber using an automated tile scan routine (850.19 μm×850.19 μm, 2140 pixels×2140 pixels per image, 64 images). A 10×EC Plan-Neofluar objective with a numerical aperture, NA=0.3 was used for imaging. The TopFluor dye was excited using a 488 nm argon laser set at 4% power. Confocal z-stacks of GUVs growing on the fibers of the fabric, with axial-spacing of 0.67 μm, were collected using a 20×W Plan-Apochromat water immersion objective with a NA=1.0.

A custom routine written in MATLAB (Mathworks Inc., Natick, MA) was used to analyze the images. The routine used an intensity threshold followed by watershed segmentation to identify fluorescent objects from the background. Li et al. (2018) *Biomacromolecules* 19:849-859. The native regionprops routine tabulated the equivalent diameters and mean fluorescence intensities of the objects. GUVs were distinguished from other lipid structures based on their mean intensities (Li et al., supra) and their size (>1 μm).

Example 11: Formation of Vesicles on Wool

Wool is a natural protein-based fiber. The fleece of sheep are the primary source of commercial wool fibers. Wool fibers are composed of the insoluble protein keratin. The molecular structure of wool is rich in hydrophilic amide groups as well as hydrophobic covalently attached fatty acids (Table 2). Wool has a moisture regain of 16% indicating that the hydrophobic fatty acids do not inhibit the adsorption of moisture. See, for example, Cook, J. G. *Handbook of Textile Fibres: Natural Fibres,* 5th ed.; Woodhead Publishing: Cambridge, UK, 1984.

Wool (100% Merino Wool Interlock—washable) was obtained from Nature's Fabrics (Edinboro, PA). The fabric was cut into 10 cm×10 cm squares. Two fabric squares were placed in a 100 ml glass media bottle containing 100 ml of chloroform (neat) and the contents of the bottle were stirred for 30 min using a magnetic stirrer and a Teflon® stir bar. The process was repeated twice, using fresh chloroform each time; after which the fabric was removed from the bottle and the chloroform allowed to evaporate from the fabric. The fabric squares were then placed into a 1 liter glass media bottle containing 1 liter of ultrapure water. Alternate cycles of soaking and rinsing in water were continued for 3 hours. Fabric squares were then allowed to dry under ambient conditions and stored in clean plastic petri dishes.

For lipid deposition and vesicle (GUV) formation, a 2 mg/ml solution of DOPC:TopFluor-PC (99.5:0.5 mole %) was prepared in chloroform (neat). Discs of fabric with a diameter of 9.5 mm were cut from the cleaned, dried fabric squares. Lipid solution was deposited on the discs to provide a concentration of 1.5 μg lipid solution per milligram of fabric substrate. The deposited liquid was allowed to evaporate under ambient conditions, and the dried fabric was then placed in a vacuum chamber for one hour to drive off residual solvent. The fabric discs were then removed from the vacuum and each disc was placed in a microcentrifuge tube to which was added 0.5 ml of sucrose (100 mM in water) after which the tubes were incubated for one hour under ambient conditions to allow vesicle growth.

To harvest vesicles, a 0.1 ml droplet of 100 mM sucrose in water was placed on a clean glass cover slip; and the fabric was removed from the microcentrifuge tube and quickly immersed in the droplet. Vesicles were harvested by gently aspirating the droplet into a 1 ml micropipette tip while moving the tip (whose opening had been enlarged by cutting off the end of the tip) systematically over the surface of the fabric disc.

Images of the dry fabrics were obtained by scanning electron microscopy (SEM) using a GeminiSEM 500 field emission scanning electron microscope (Zeiss) with a beam accelerating voltage of 1 kV. Secondary electrons were collected from the surface of the fabric substrate using an Everhart-Thomley secondary electron detector.

For confocal imaging, square imaging chambers (6 mm wide×6 mm long×1 mm high) were fabricated from polydimethylsiloxane (PDMS) bonded onto glass microscope slides. The surfaces of the chamber were passivated with casein to prevent rupture of vesicles during imaging and preparation for imaging. Glucose (56 μl of a 100 mM aqueous solution) was placed in the chamber and a 4 μl aliquot of harvested vesicle solution was added to the glucose solution. After 3 hours (during which time the sucrose-filled vesicles sedimented to the bottom of the chamber due to their higher density) an upright confocal laser scanning microscope (Zeiss LSM 880 with Airyscan+ FAST, Axio Imager.Z2m) was used to capture single-plane confocal images of the entire area of the chamber using an automated tile scan routine (850.19 μm×850.19 μm, 2140 pixels×2140 pixels per image, 64 images). A 10×EC Plan-Neofluar objective with a numerical aperture, NA=0.3 was used for imaging. The TopFluor dye was excited using a 488 nm argon laser set at 4% power. Confocal z-stacks of GUVs growing on the fibers of the fabric, with axial-spacing of 0.67 μm, were collected using a 20×W Plan-Apochromat water immersion objective with a NA=1.0.

A custom routine written in MATLAB (Mathworks Inc., Natick, MA) was used to analyze the images. The routine used an intensity threshold followed by watershed segmentation to identify fluorescent objects from the background. Li et al. (2018) *Biomacromolecules* 19:849-859. The native regionprops routine tabulated the equivalent diameters and mean fluorescence intensities of the objects. GUVs were distinguished from other lipid structures based on their mean intensities (Li et al., supra) and their size (>1 μm).

Example 12: Formation of Vesicles on Rayon Fabric

Wet-spinning of a cellulosic solution through a spinneret followed by chemical regeneration of the cellulose polymers results in long fibers of rayon of controlled size and crystallinity. This process converts short cellulose fibers from woody materials into long fibers that resemble cotton or silk. Rayon is a semisynthetic fiber since the feedstock originates from a natural source. Natural bio-derived cellulose has a Cellulose I crystal structure. Regenerated cellulose has a Cellulose II crystal structure. Similar to cotton, rayon is rich in hydrophilic hydroxyl groups (Table 2). Rayon has a moisture regain of 11%. See, for example, Cook, J. G. *Handbook of Textile Fibres: Man-Made Fibres,* 5th ed.; Woodhead Publishing: Cambridge, UK, 1984.

Rayon (Sportswear Modal Fabric, White, 100% rayon) was obtained from a local craft store (JoAnn, LLC, Merced, CA). The fabric was cut into 10 cm×10 cm squares. Two fabric squares were placed in a 100 ml glass media bottle containing 100 ml of chloroform (neat) and the contents of the bottle were stirred for 30 min using a magnetic stirrer and a Teflon® stir bar. The process was repeated twice, using fresh chloroform each time; after which the fabric was removed from the bottle and the chloroform allowed to evaporate from the fabric. The fabric squares were then placed into a 1 liter glass media bottle containing 1 liter of ultrapure water. Alternate cycles of soaking and rinsing in water were continued for 3 hours. Fabric squares were then allowed to dry under ambient conditions and stored in clean plastic petri dishes.

For lipid deposition and vesicle (GUV) formation, a 2 mg/ml solution of DOPC:TopFluor-PC (99.5:0.5 mole %) was prepared in chloroform (neat). Discs of fabric with a diameter of 9.5 mm were cut from the cleaned, dried fabric squares. Lipid solution was deposited on the discs to provide a concentration of 3 μg lipid solution per milligram of fabric substrate. The deposited liquid was allowed to evaporate under ambient conditions, and the dried fabric was then placed in a vacuum chamber for one hour to drive off residual solvent. The fabric discs were then removed from the vacuum and each disc was placed in a microcentrifuge tube to which was added 0.5 ml of sucrose (100 mM in water) after which the tubes were incubated for one hour under ambient conditions to allow vesicle growth.

To harvest vesicles, a 0.1 ml droplet of 100 mM sucrose in water was placed on a clean glass cover slip; and the fabric was removed from the microcentrifuge tube and quickly immersed in the droplet. Vesicles were harvested by gently aspirating the droplet into a 1 ml micropipette tip while moving the tip (whose opening had been enlarged by cutting off the end of the tip) systematically over the surface of the fabric disc.

Images of the dry fabrics were obtained by scanning electron microscopy (SEM) using a GeminiSEM 500 field emission scanning electron microscope (Zeiss) with a beam accelerating voltage of 1 kV. Secondary electrons were collected from the surface of the fabric substrate using an Everhart-Thomley secondary electron detector.

For confocal imaging, square imaging chambers (6 mm wide×6 mm long×1 mm high) were fabricated from polydimethylsiloxane (PDMS) bonded onto glass microscope slides. The surfaces of the chamber were passivated with casein to prevent rupture of vesicles during imaging and preparation for imaging. Glucose (58 μl of a 100 mM aqueous solution) was placed in the chamber and a 2 μl aliquot of harvested vesicle solution was added to the glucose solution. After 3 hours (during which time the sucrose-filled vesicles sedimented to the bottom of the chamber due to their higher density) an upright confocal laser scanning microscope (Zeiss LSM 880 with Airyscan+ FAST, Axio Imager.Z2m) was used to capture single-plane confocal images of the entire area of the chamber using an automated tile scan routine (850.19 μm×850.19 μm, 2140 pixels×2140 pixels per image, 64 images). A 10×EC Plan-Neofluar objective with a numerical aperture, NA=0.3 was used for imaging. The TopFluor dye was excited using a 488 nm argon laser set at 4% power. Confocal z-stacks of GUVs growing on the fibers of the fabric, with axial-spacing of 0.67 μm, were collected using a 20×W Plan-Apochromat water immersion objective with a NA=1.0.

A custom routine written in MATLAB (Mathworks Inc., Natick, MA) was used to analyze the images. The routine used an intensity threshold followed by watershed segmentation to identify fluorescent objects from the background. Li et al. (2018) *Biomacromolecules* 19:849-859. The native regionprops routine tabulated the equivalent diameters and mean fluorescence intensities of the objects. GUVs were distinguished from other lipid structures based on their mean intensities (Li et al., supra) and their size (>1 μm).

Example 13: Formation of Vesicles on Nylon Fabric

Nylon 6,6 is a synthetic fiber made by melt-spinning polyamides that result from the polycondensation of hexamethylenediamine and adipic acid. The molecular structure of Nylon 6,6 is rich in hydrophilic amides. Nylon has a moisture regain of 4.0-4.5% (Table 2). The raw material for nylon originates from petroleum byproducts See, for example, Cook, J. G. *Handbook of Textile Fibres: Man-Made Fibres,* 5th ed.; Woodhead Publishing: Cambridge, UK, 1984.

Nylon (Sport Nylon Fabric, White, 100% nylon) was obtained from a local craft store (JoAnn, LLC, Merced, CA). The fabric was cut into 10 cm×10 cm squares. Two fabric squares were placed in a 100 ml glass media bottle containing 100 ml of chloroform (neat) and the contents of the bottle were stirred for 30 min using a magnetic stirrer and a Teflon® stir bar. The process was repeated twice, using fresh chloroform each time; after which the fabric was removed from the bottle and the chloroform allowed to evaporate from the fabric. The fabric squares were then placed into a 1 liter glass media bottle containing 1 liter of ultrapure water. Alternate cycles of soaking and rinsing in water were continued for 3 hours. Fabric squares were then allowed to dry under ambient conditions and stored in clean plastic petri dishes.

For lipid deposition and vesicle (GUV) formation, a 2 mg/ml solution of DOPC:TopFluor-PC (99.5:0.5 mole %) was prepared in chloroform (neat). Discs of fabric with a diameter of 9.5 mm were cut from the cleaned, dried fabric squares. Lipid solution was deposited on the discs to provide a concentration of 3 μg lipid solution per milligram of fabric substrate. The deposited liquid was allowed to evaporate under ambient conditions, and the dried fabric was then placed in a vacuum chamber for one hour to drive off residual solvent. The fabric discs were then removed from the vacuum and each disc was placed in a microcentrifuge tube to which was added 0.5 ml of sucrose (100 mM in water) after which the tubes were incubated for one hour under ambient conditions to allow vesicle growth.

To harvest vesicles, a 0.1 ml droplet of 100 mM sucrose in water was placed on a clean glass cover slip; and the fabric was removed from the microcentrifuge tube and quickly immersed in the droplet. Vesicles were harvested by gently aspirating the droplet into a 1 ml micropipette tip while moving the tip (whose opening had been enlarged by cutting off the end of the tip) systematically over the surface of the fabric disc.

Images of the dry fabrics were obtained by scanning electron microscopy (SEM) using a GeminiSEM 500 field emission scanning electron microscope (Zeiss) with a beam accelerating voltage of 1 kV. Secondary electrons were collected from the surface of the fabric substrate using an Everhart-Thomley secondary electron detector.

For confocal imaging, square imaging chambers (6 mm wide×6 mm long×1 mm high) were fabricated from polydimethylsiloxane (PDMS) bonded onto glass microscope slides. The surfaces of the chamber were passivated with casein to prevent rupture of vesicles during imaging and preparation for imaging. Glucose (56 μl of a 100 mM aqueous solution) was placed in the chamber and a 4 μl aliquot of harvested vesicle solution was added to the glucose solution. After 3 hours (during which time the sucrose-filled vesicles sedimented to the bottom of the chamber due to their higher density) an upright confocal laser scanning microscope (Zeiss LSM 880 with Airyscan+ FAST, Axio Imager.Z2m) was used to capture single-plane confocal images of the entire area of the chamber using an automated tile scan routine (850.19 μm×850.19 μm, 2140 pixels×2140 pixels per image, 64 images). A 10×EC Plan-Neofluar objective with a numerical aperture, NA=0.3 was used for imaging. The TopFluor dye was excited using a 488 nm argon laser set at 4% power. Confocal z-stacks of GUVs growing on the fibers of the fabric, with axial-spacing of 0.67 μm, were collected using a 20×W Plan-Apochromat water immersion objective with a NA=1.0.

A custom routine written in MATLAB (Mathworks Inc., Natick, MA) was used to analyze the images. The routine used an intensity threshold followed by watershed segmentation to identify fluorescent objects from the background. Li et al. (2018) *Biomacromolecules* 19:849-859. The native regionprops routine tabulated the equivalent diameters and mean fluorescence intensities of the objects. GUVs were distinguished from other lipid structures based on their mean intensities (Li et al., supra) and their size (>1 μm).

Example 14: Formation of Vesicles on Polyester Fabric

Polyester fibers are melt-spun polyethylene terephthalate. Along with hydrophilic carbonyl groups, polyester is rich in hydrophobic aromatic and methyl groups (Table 2). Polyester has a low moisture regain of 0.4%. The raw material for polyester originates from petroleum byproducts. See, for example, Cook, J. G. *Handbook of Textile Fibres: Man-Made Fibres,* 5th ed.; Woodhead Publishing: Cambridge, UK, 1984.

Polyester (Satin Tafetta, White, 100% polyester) was obtained from a local craft store (JoAnn, LLC, Merced, CA). The fabric was cut into 10 cm×10 cm squares. Two fabric squares were placed in a 100 ml glass media bottle containing 100 ml of chloroform (neat) and the contents of the bottle were stirred for 30 min using a magnetic stirrer and a Teflon® stir bar. The process was repeated twice, using fresh chloroform each time; after which the fabric was removed from the bottle and the chloroform allowed to evaporate from the fabric. The fabric squares were then placed into a 1 liter glass media bottle containing 1 liter of ultrapure water. Alternate cycles of soaking and rinsing in water were continued for 3 hours. Fabric squares were then allowed to dry under ambient conditions and stored in clean plastic petri dishes.

For lipid deposition and vesicle (GUV) formation, a 2 mg/ml solution of DOPC:TopFluor-PC (99.5:0.5 mole %) was prepared in chloroform (neat). Discs of fabric with a diameter of 9.5 mm were cut from the cleaned, dried fabric squares. Lipid solution was deposited on the discs to provide a concentration of 3 μg lipid solution per milligram of fabric substrate. The deposited liquid was allowed to evaporate under ambient conditions, and the dried fabric was then placed in a vacuum chamber for one hour to drive off residual solvent. The fabric discs were then removed from the vacuum and each disc was placed in a microcentrifuge tube to which was added 0.5 ml of sucrose (100 mM in water) after which the tubes were incubated for one hour under ambient conditions to allow vesicle growth.

To harvest vesicles, a 0.1 ml droplet of 100 mM sucrose in water was placed on a clean glass cover slip; and the fabric was removed from the microcentrifuge tube and quickly immersed in the droplet. Vesicles were harvested by gently aspirating the droplet into a 1 ml micropipette tip while moving the tip (whose opening had been enlarged by cutting off the end of the tip) systematically over the surface of the fabric disc.

Images of the dry fabrics were obtained by scanning electron microscopy (SEM) using a GeminiSEM 500 field emission scanning electron microscope (Zeiss) with a beam accelerating voltage of 1 kV. Secondary electrons were collected from the surface of the fabric substrate using an Everhart-Thomley secondary electron detector.

For confocal imaging, square imaging chambers (6 mm wide×6 mm long×1 mm high) were fabricated from polydimethylsiloxane (PDMS) bonded onto glass microscope slides. The surfaces of the chamber were passivated with casein to prevent rupture of vesicles during imaging and preparation for imaging. Glucose (56 μl of a 100 mM aqueous solution) was placed in the chamber and a 4 μl aliquot of harvested vesicle solution was added to the glucose solution. After 3 hours (during which time the sucrose-filled vesicles sedimented to the bottom of the chamber due to their higher density) an upright confocal laser scanning microscope (Zeiss LSM 880 with Airyscan+ FAST, Axio Imager.Z2m) was used to capture single-plane confocal images of the entire area of the chamber using an automated tile scan routine (850.19 μm×850.19 μm, 2140 pixels×2140 pixels per image, 64 images). A 10×EC Plan-Neofluar objective with a numerical aperture, NA=0.3 was used for imaging. The TopFluor dye was excited using a 488 nm argon laser set at 4% power. Confocal z-stacks of GUVs growing on the fibers of the fabric, with axial-spacing of 0.67 μm, were collected using a 20×W Plan-Apochromat water immersion objective with a NA=1.0.

A custom routine written in MATLAB (Mathworks Inc., Natick, MA) was used to analyze the images. The routine used an intensity threshold followed by watershed segmentation to identify fluorescent objects from the background.

Li et al. (2018) *Biomacromolecules* 19:849-859. The native regionprops routine tabulated the equivalent diameters and mean fluorescence intensities of the objects. GUVs were distinguished from other lipid structures based on their mean intensities (Li et al., supra) and their size (>1 μm).

Example 15: Formation of Vesicles on Fiberglass Fabric

Fiberglass is solidified extruded molten glass. Fiberglass is hydrophilic due to the presence of many surface hydroxyl group (Table 2). See, for example, Cook, J. G. *Handbook of Textile Fibres: Man-Made Fibres,* 5th ed.; Woodhead Publishing: Cambridge, UK, 1984.

Plain weaved fiberglass fabric (3 oz Fabric Style120 E-Glass) was obtained from Fibre Glast Developments Corp. (Brookville, OH). The fabric was cut into 10 cm×10 cm squares. Two fabric squares were placed in a 100 ml glass media bottle containing 100 ml of chloroform (neat) and the contents of the bottle were stirred for 30 min using a magnetic stirrer and a Teflon® stir bar. The process was repeated twice, using fresh chloroform each time; after which the fabric was removed from the bottle and the chloroform allowed to evaporate from the fabric. The fabric squares were then placed into a 1 liter glass media bottle containing 1 liter of ultrapure water. Alternate cycles of soaking and rinsing in water were continued for 3 hours. Fabric squares were then allowed to dry under ambient conditions and stored in clean plastic petri dishes.

For lipid deposition and vesicle (GUV) formation, a 2 mg/ml solution of DOPC:TopFluor-PC (99.5:0.5 mole %) was prepared in chloroform (neat). Discs of fabric with a diameter of 9.5 mm were cut from the cleaned, dried fabric squares. Lipid solution was deposited on the discs to provide a concentration of 3 μg lipid solution per milligram of fabric substrate. The deposited liquid was allowed to evaporate under ambient conditions, and the dried fabric was then placed in a vacuum chamber for one hour to drive off residual solvent. The fabric discs were then removed from the vacuum and each disc was placed in a microcentrifuge tube to which was added 0.5 ml of sucrose (100 mM in water) after which the tubes were incubated for one hour under ambient conditions to allow vesicle growth.

To harvest vesicles, a 0.1 ml droplet of 100 mM sucrose in water was placed on a clean glass cover slip; and the fabric was removed from the microcentrifuge tube and quickly immersed in the droplet. Vesicles were harvested by gently aspirating the droplet into a 1 ml micropipette tip while moving the tip (whose opening had been enlarged by cutting off the end of the tip) systematically over the surface of the fabric disc.

Images of the dry fabrics were obtained by scanning electron microscopy (SEM) using a GeminiSEM 500 field emission scanning electron microscope (Zeiss) with a beam accelerating voltage of 1 kV. Secondary electrons were collected from the surface of the fabric substrate using an Everhart-Thomley secondary electron detector.

For confocal imaging, square imaging chambers (6 mm wide×6 mm long×1 mm high) were fabricated from polydimethylsiloxane (PDMS) bonded onto glass microscope slides. The surfaces of the chamber were passivated with casein to prevent rupture of vesicles during imaging and preparation for imaging. Glucose (56 μl of a 100 mM aqueous solution) was placed in the chamber and a 4 μl aliquot of harvested vesicle solution was added to the glucose solution. After 3 hours (during which time the sucrose-filled vesicles sedimented to the bottom of the chamber due to their higher density) an upright confocal laser scanning microscope (Zeiss LSM 880 with Airyscan+ FAST, Axio Imager.Z2m) was used to capture single-plane confocal images of the entire area of the chamber using an automated tile scan routine (850.19 μm×850.19 μm, 2140 pixels×2140 pixels per image, 64 images). A 10×EC Plan-Neofluar objective with a numerical aperture, NA=0.3 was used for imaging. The TopFluor dye was excited using a 488 nm argon laser set at 4% power. Confocal z-stacks of GUVs growing on the fibers of the fabric, with axial-spacing of 0.67 μm, were collected using a 20×W Plan-Apochromat water immersion objective with a NA=1.0.

A custom routine written in MATLAB (Mathworks Inc., Natick, MA) was used to analyze the images. The routine used an intensity threshold followed by watershed segmentation to identify fluorescent objects from the background. Li et al. (2018) *Biomacromolecules* 19:849-859. The native regionprops routine tabulated the equivalent diameters and mean fluorescence intensities of the objects. GUVs were distinguished from other lipid structures based on their mean intensities (Li et al., supra) and their size (>1 μm).

Example 16: Comparison of Vesicles Formed on Natural, Semi-Synthetic and Synthetic Fabrics All fabrics promoted vesiculation of GUVs on their fibers.

Figure 11:
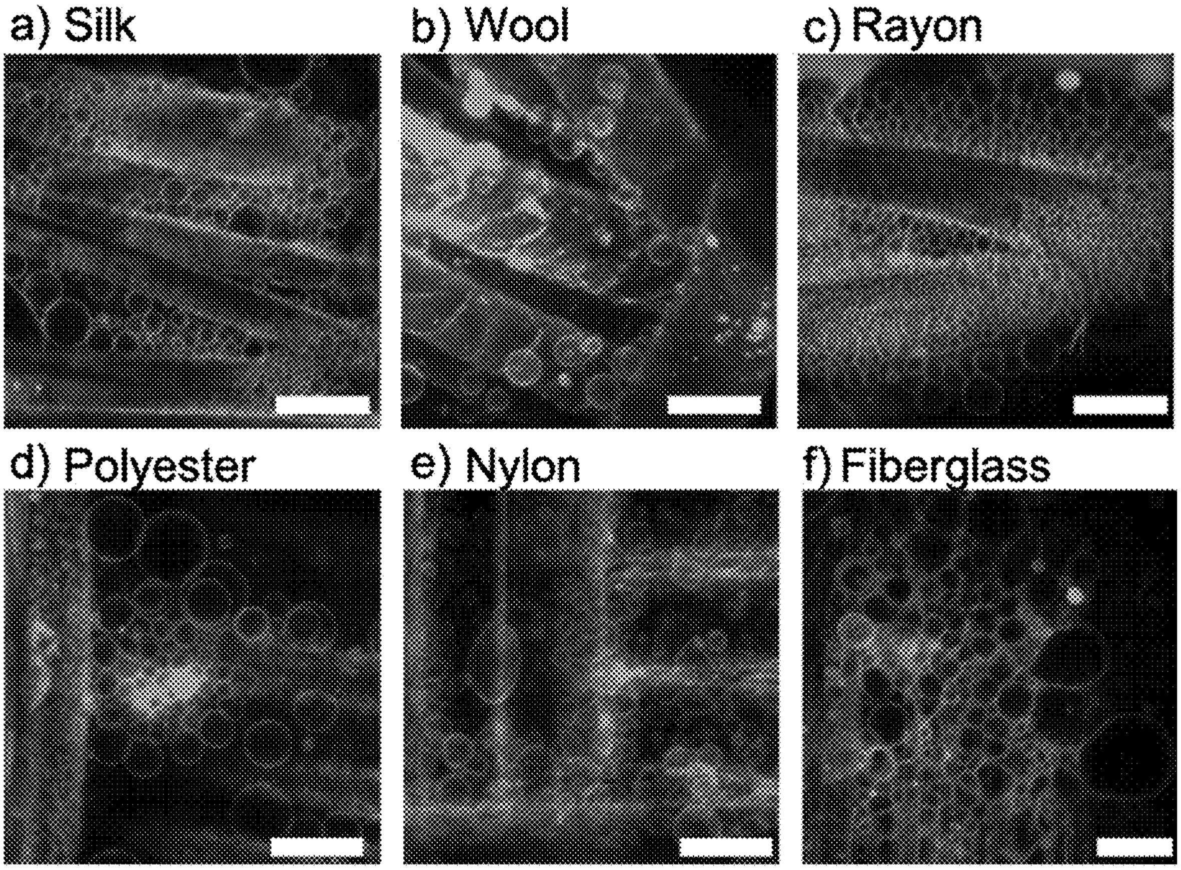
FIGS. 11*a-f* show fluorescent confocal images of lipids on the surfaces of hydrated fabrics after 1 hour.

FIG. 11 shows confocal microscope images of the lipid-coated fabrics one hour after incubation in the aqueous buffer. All the fabrics tested had GUVs growing from the surfaces of their fibers. Most of the GUVs had tethers to the lipid layer coating the fibers. Li et al. (2018) *Biomacromolecules* 19:849-859. These results show that the spontaneous formation of GUVs is not limited to cellulose, but is general to fibers of differing surface chemistries.

Figure 12:
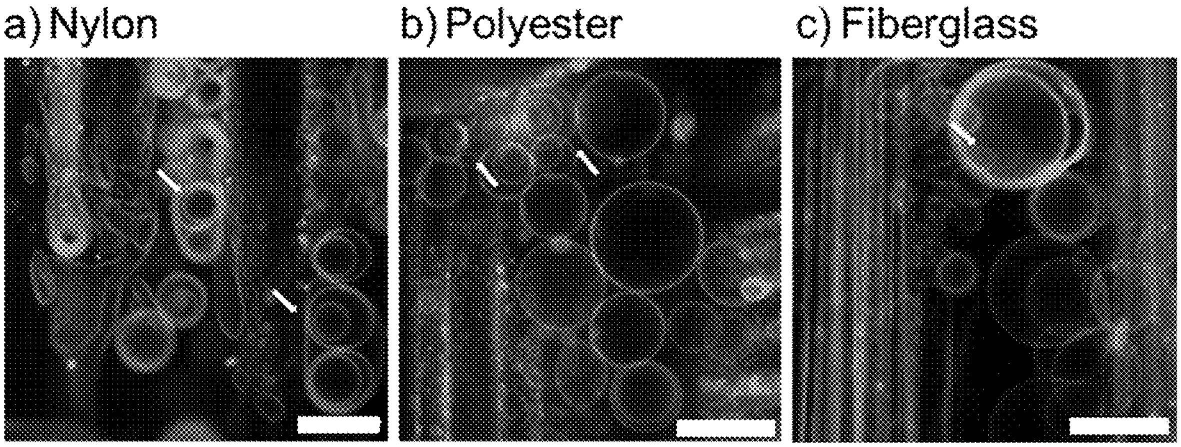
FIGS. 12*a-c* show fluorescent confocal images of lipids on the surfaces of hydrated fabrics after 1 hour.

The configuration and abundance of GUVs, and the nature and abundance of other lamellar structures, differed on the assorted fabrics. Silk and rayon had spherical GUVs that appeared qualitatively similar to those seen on cellulose paper and cellulose fabric. See examples supra. GUVs were highly abundant on these fabrics (silk and rayon), and coated the fibers in stacked layers that filled the pores between the fibers of the fabric. Wool had noticeably fewer GUVs than the other fabrics. Nylon, polyester, and fiberglass fabrics had an intermediate number of GUVs. We observed that GUVs formed only from the lipid layer that coated the fibers. On the other hand, non-GUV, multilamellar lipid structures formed from lipid deposits that spanned the gaps between the fibers (FIG. 12). These lipid deposits were more prevalent on wool, nylon, polyester, and fiberglass than on rayon, silk, or cotton. Thus, along with GUVs, a sizable number of other lamellar structures were present on the wool, nylon, polyester, and fiberglass fabrics. Furthermore, giant polymer vesicles from the amphiphilic diblock copolymer poly(butadiene-b-ethyleneoxide) PBD46PEO30 and the amphiphilic triblock copolymer polyoxyethylene-polyoxypropylene-polyoxyethylene (PEO5PPO67PEO5, Pluronic L121) also formed on all the fabrics, showing that vesicle growth on fibers is general to other lamellar phase-forming amphiphiles.

The Fabrics Produced Different Numbers of GUVs Per Unit Mass of Lipid.

Figure 13:
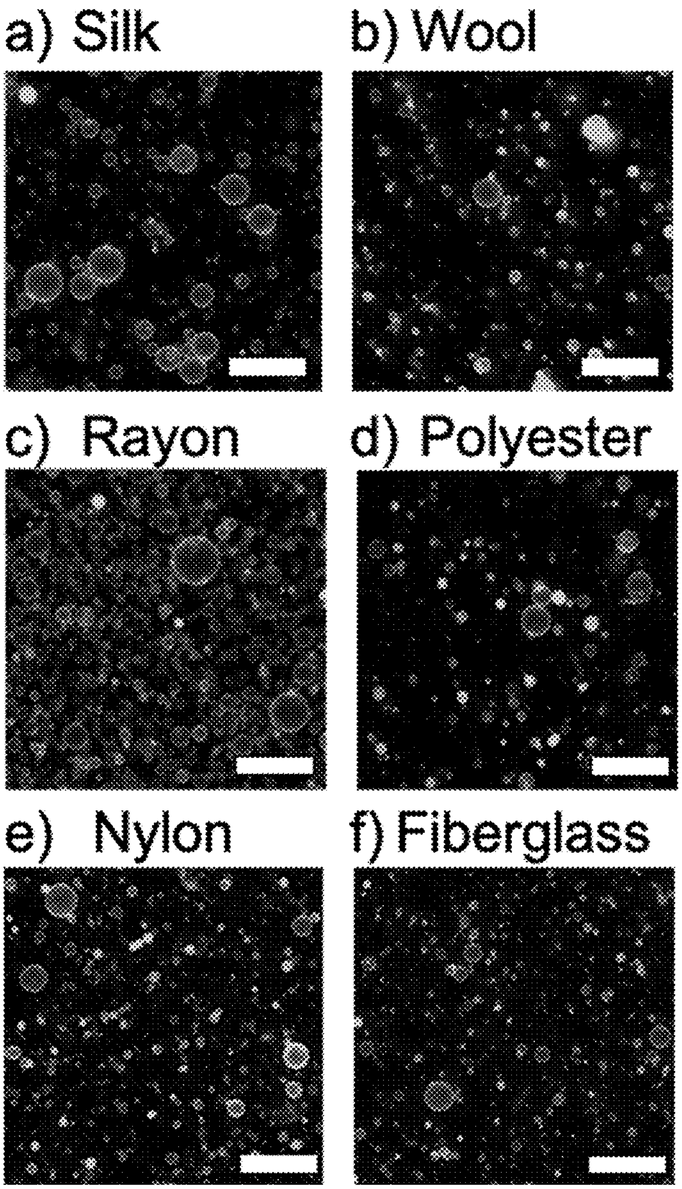
FIGS. 13*a-f* show representative images of harvested GUVs formed on different fibers

Lipid structures were harvested from the fabrics as described above, and, after allowing the structures to sediment for 3 hr in a custom imaging chamber, aliquots from the suspensions were examined by confocal fluorescence microscopy. A fraction of GUVs and other structures remain trapped in the fabric after the harvesting process, as previously observed. Kresse et al. (2016) ACS Appl. Mater. Interfaces 8: 32102-32107; Li et al., supra; Pazzi et al., "Size distributions and yields of giant vesicles assembled on cellulose papers and cotton fabric," Langmuir, In Press. FIGS. 13(*a-f*) shows typical fields of view obtained from a 4 μL aliquot of the harvested solution diluted in 56 μL of isomolar glucose buffer. Structures harvested from silk and rayon, similar to those from cotton fabric and cellulose paper (Pazzi et al., supra), appeared to be predominantly GUVs. Consistent with direct observations of the structures on the fabrics, a larger fraction of lipid aggregates, lipid nanotubes, and debris were present in the samples harvested from wool, nylon, polyester, and fiberglass. For all fabrics, the number of GUVs in a typical field view was sufficient to perform biophysical experiments (e.g., Walde et al. (2010) *ChemBioChem.* 11:848-865; Dimova et al. (2006) *J Phys. Condens. Matter* 18:S1151-51176; Steer et al. (2018) *Langmuir* 34:7561-7574; Dietrich et al. (2001) *Proc. Natl. Acad. Sci. USA* 98:10642-10647; Veatch et al. (2003) *Biophys. J.* 85:3074-3083), albeit some had more lipid debris and other non-GUV structures.

Figure 14:
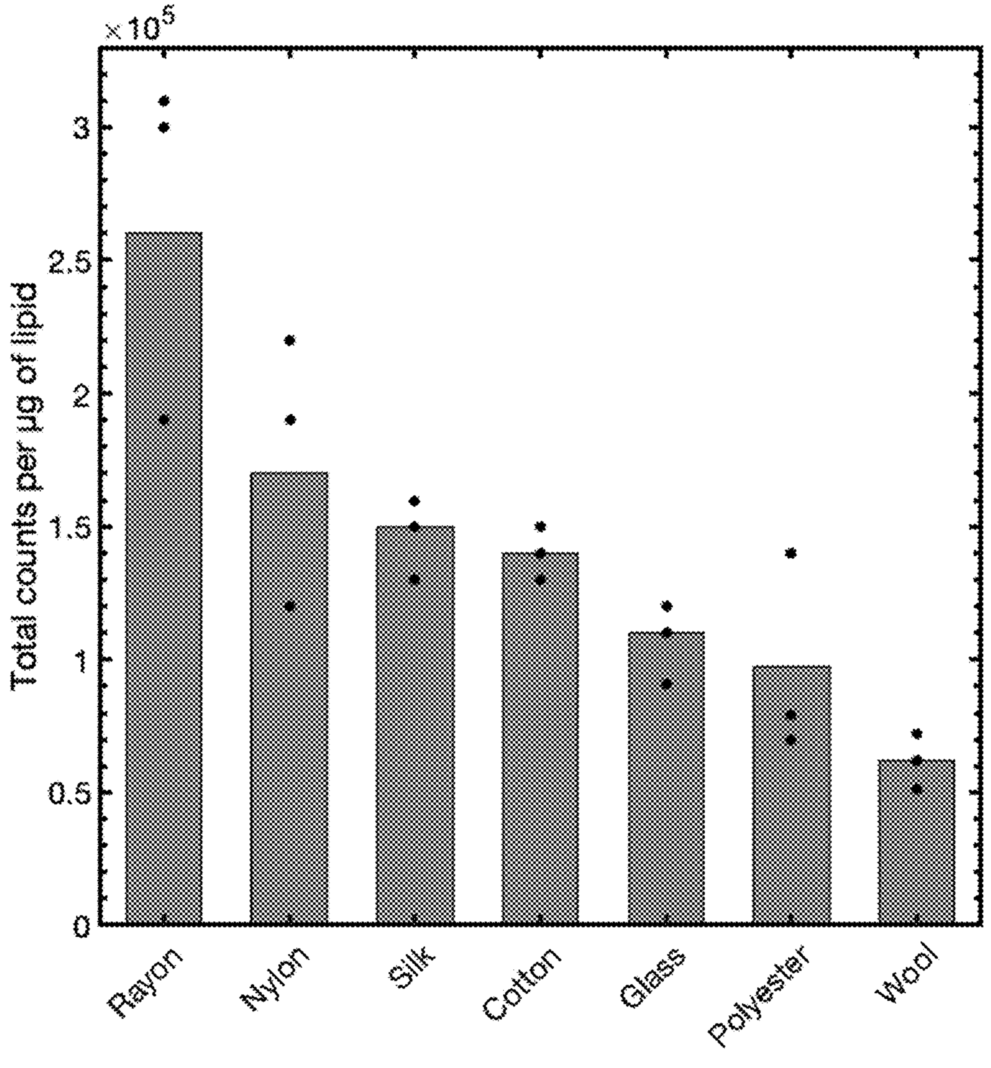
FIG. 14 is a bar plot showing the number of GUVs formed, per microgram of lipid, on different fabrics. Black circles are the data points for each of three experiments conducted with each type of fabric, and the height of the bar indicates the average number of GUVs obtained per microgram of lipid, based on the three data points for each fabric.

To obtain quantitative insight into the sizes and yields of the GUVs, images were analyzed using a custom MATLAB routine (Pazzi et al., supra). Three independent experiments were performed for each type of fabric. Each experiment had large sample sizes ranging from n=$\mathcal{O}(10^4)$ to $\mathcal{O}(10^5)$ GUVs. GUVs were identified based on their fluorescence intensity (Li et al. (2018) supra) and their size (>1 μm diameter). FIG. 14 shows a bar plot of the number of GUVs obtained from the fabrics arranged in descending order from left to right. The height of the bar is the average of the three experiments for each fabric type. The points are the counts from the three independent experiments. To allow comparison between the fabrics, GUV count was normalized to the mass of lipid deposited on each fabric. Overall, rayon produced the highest average number of GUVs per unit mass of deposited lipid at $2.6\times10^5$ GUVs per μg lipid, while wool had the lowest average number of GUVs at $6.2\times10^4$ GUVs per μg of lipid. Rayon, nylon, and polyester had larger sample-to-sample variation in GUV numbers than did the other fabrics.

Similar to what has been observed with cotton fabric (Pazzi et al. (2018) supra), the process of GUV growth did not alter the fibers of the fabrics. All the fabrics supported at least five cycles of GUV growth and harvest, with no measurable changes in the characteristics of the GUVs.

Distribution of GUV Sizes Varied Among the Fabrics.

Figure 15:
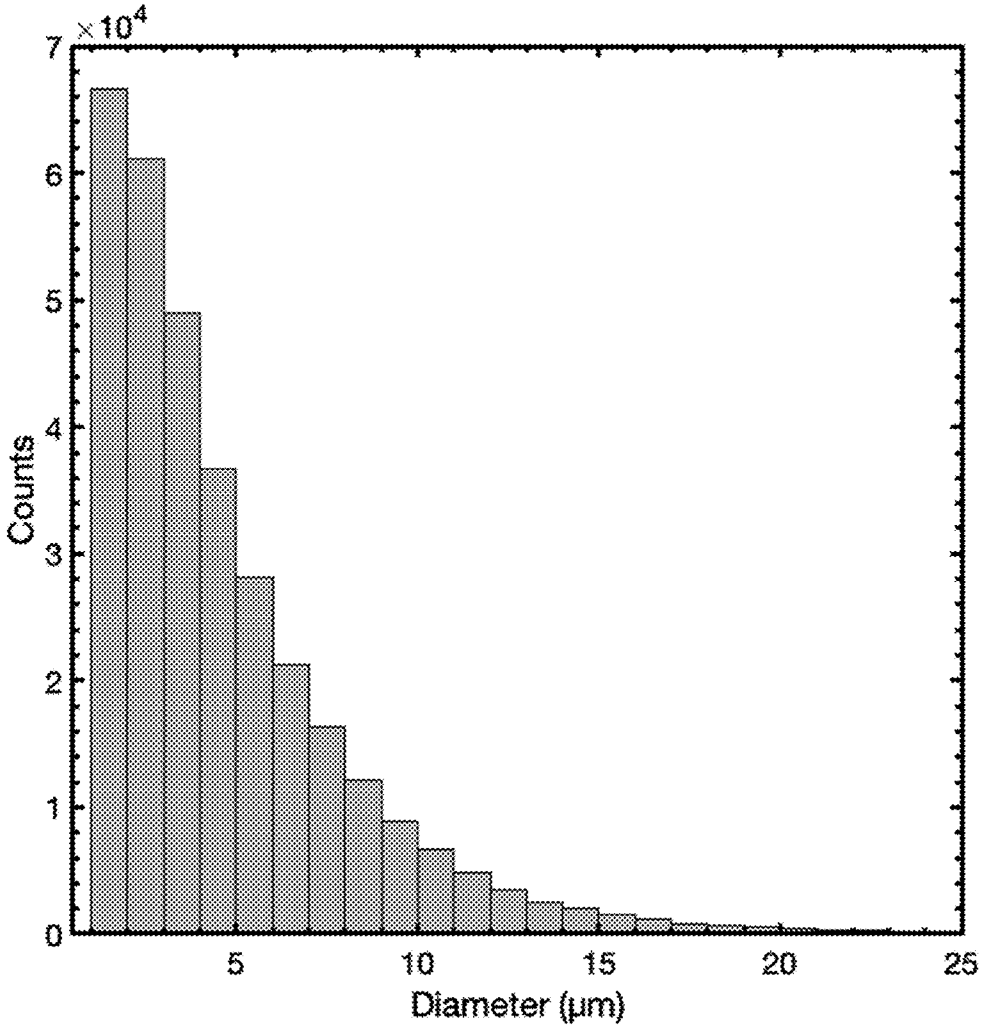
FIG. 15 shows a representative histogram of diameters of GUVs harvested from silk. Bin widths are 1 μm.
Figure 16:
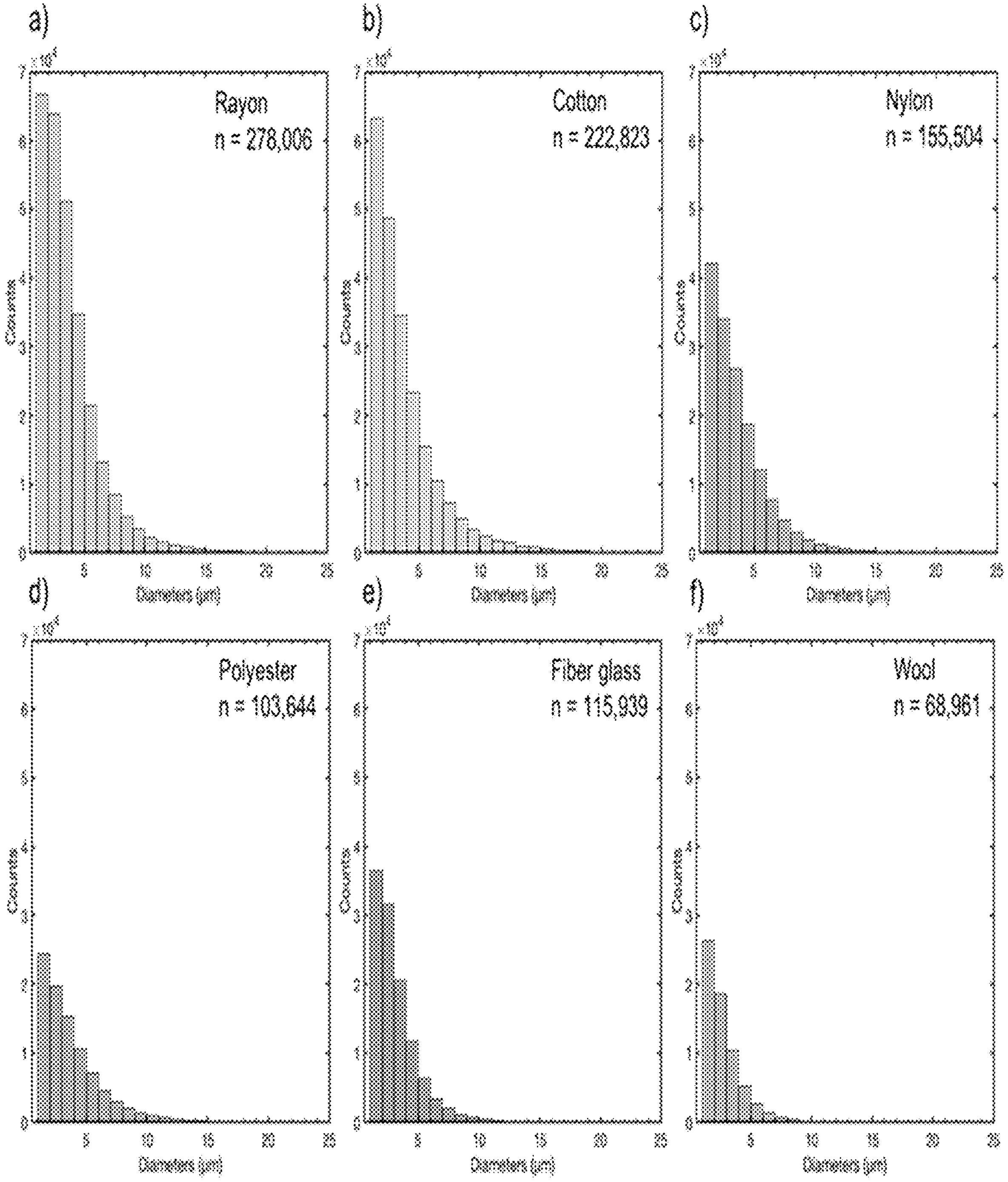
FIG. 16*a-f* show representative histograms of diameters of GUVs harvested from different fabrics.

Sizes of GUVs obtained from the different fabrics were analyzed. FIG. 15 shows a histogram of the diameters of the GUVs harvested from silk. The bin width is 1 μm, and the sample size, n=113,461. The distribution of the diameters was unimodal with a prominent right tail. Smaller GUVs were more abundant than larger GUVs. Populations of GUVs harvested from the other fabrics also showed similar unimodal right-skewed distributions of diameters (FIG. 16). These results further add to the growing body of evidence that populations of GUVs obtained from the vesiculation of lamellar stacks of phospholipids on disparate surfaces such as solid glass, hydrogels and cylindrical fibers have broad and right-skewed distributions in diameters. Reeves & Dowben (1969) *J. Cell. Physiol.* 73:49-60; López Mora et al. (2014) *Chem. Commun.* 50:1953-1955; Movsesian et al. (2018) *Langmuir* 34:9025-9035; Peruzzi et al. (2016) *Langmuir* 32:12702-12709; Greene et al. (2016) *PLoS One* 11:e0158729; Kresse et al., supra, Li et al., supra, Pazzi et al., supra. Without wishing to be bound by any particular theory, the similarity in size distributions suggests the possibility of similar underlying dynamics governing the processes of vesiculation and growth.

FIG. 17 shows empirical cumulative distribution functions of the populations of GUVs obtained from each fabric. The points are the mean cumulative probability from the three experiments. The error bars are the standard deviation from the mean. Median diameters for each population are shown in Table 3. Overall, ninety-eight percent of the GUVs harvested from all the fabrics had diameters <20 μm. Populations of GUVs harvested from silk had the highest fraction of GUVs with larger diameters; with a median diameter of 3.7±0.3 μm. Samples harvested from wool and fiberglass had the smallest fraction of GUVs with larger diameters; with median diameters of 2.7±0.3 μm and 2.5±0.1 μm respectively. Populations of GUVs harvested from cotton and rayon had similar cumulative distribution in diameters; with median diameters of 3.2±0.1 μm. The median diameter of the populations of GUVs harvested from nylon and polyester was 2.8±0.2 μm for both populations.

The cumulative distribution function considers the distribution of diameters of a given population independent of the total size of the population. To account for the significant differences in yield, GUV counts were normalized on a per unit mass basis and the resultant data was expressed on a logarithmic scale for GUV number on the y-axis (FIG. 18). The semilogarithmic axis accommodates the broad range in GUV counts. The points are the average of the counts in each bin from the three experiments for each fabric. Per unit mass of lipid, rayon produced the highest counts of GUVs of all sizes. Silk showed an interesting dichotomy due to the interplay between the distribution in GUV sizes (FIG. 17) and the yield per unit mass of lipid (FIG. 14). Within sample-to-sample variation, both silk and rayon produced similar numbers of GUVs with diameters >10 μm per μg of deposited lipid. However, silk had fewer GUVs of diameters <10 μm per μg of deposited lipid compared to rayon. Cotton produced lower counts of GUVs of all sizes compared to both rayon and silk but out-performed polyester, wool, and fiberglass. Nylon, although producing similar average numbers of GUVs as silk (FIG. 14), had lower numbers of GUVs >5 μm when compared to silk. About 15% of the GUVs from nylon were >5 μm in diameter while about 31% of the GUVs from silk were >5 μm. Wool produced the fewest GUVs per μg of deposited lipid of all sizes. Overall, per unit mass of lipid, rayon and silk produced more GUVs of larger sizes than the other fabric types. Table 3 lists the percentage of large vesicles obtained for each of the fabrics; and Table 4 provides median diameters of GUV populations obtained from each of the different fabrics.

TABLE 3

Percentage large vesicles

| Fabric | % of vesicles greater than 5 μm diameter |
|---|---|
| Silk | 31 |
| Rayon | 20 |
| Cotton | 20 |
| Polyester | 17 |
| Nylon | 15 |
| Glass | 10 |
| Wool | 10 |

TABLE 4

| Median diameters of GUV populations formed on different fabrics | |
|---|---|
| Fabric | Median diameter (μm) |
| Silk | 3.7 + 0.3 |
| Wool | 2.7 + 0.3 |
| Rayon | 3.2 + 0.2 |
| Polyester | 2.8 + 0.2 |
| Nylon | 2.8 + 0.2 |
| Cotton | 3.1 + 0.1 |
| Fiberglass | 2.5 + 0.1 |

TABLE 5

| Order of fabrics in terms of median number of GUVs per unit mass of lipid | |
|---|---|
| Fabric | Median number |
| Rayon | most |
| Nylon | ↓ |
| Silk | ↓ |
| Cotton | ↓ |
| Fiberglass | ↓ |
| Polyester | ↓ |
| Wool | least |

The process of vesicle formation on the fabrics was not unique to DOPC, but was general to other lamellar phase forming amphiphiles such as the triblock copolymer poly-oxyethylene-polyoxypropylene-polyoxyethylene (PEO5PPO67PEO5, Pluronic L121) and the diblock copolymer poly(butadiene-b-ethyleneoxide) PBD46PEO30.

Conclusions

It is shown herein that the formation of GUVs and polymersomes from lamellar films of phospholipids and amphiphilic block copolymers is general to a surprisingly wide variety of fabrics composed of cylindrical fibers of different surface chemistries. All fabrics produced populations of GUVs with right-skewed unimodal distributions in diameters. Quantitative characterization revealed that rayon and silk fabrics produced the highest yield of GUVs with larger sizes. The results provided herein suggest, without being bound by theory, that the mechanism of formation of GUVs on paper, fabrics, and other fibrous porous media depends, to a certain extent, on the physical characteristics of the fibers. The bending of the lamellar stacks to conform to the micrometer-scale curvature of the cylindrical fibers is a common feature in the fabrics. Empirically, differences in the surface chemistry of the fibers appears to affect the sizes and yields of the populations of GUVs. Formation of GUVs on fabrics composed of cylindrical fibers of widely differing chemistries suggests that curvature is a factor in promoting vesicle formation. Accordingly, but without wishing to be bound by theory, it is possible that the curvature of the fibers promotes vesiculation—cylindrical geometry is a common characteristic of the fibers—whereas differences in surface chemistry and configuration of the fibers in the fabrics control the yield and sizes of the vesicles.

Example 17: Delaying and then Triggering Vesicle Formation by Changing the Osmotic Pressure in the Bulk Solution In this example, a method to delay and then trigger vesiculation from an amphiphile-coated substrate in aqueous solution is disclosed. To obtain the lipid-coated nanofibrillar cellulose substrate, a 9.5 mm diameter piece of the nanopaper, made as described above (Example 7), was cut out and then 10 μg of DOPC:TopFluor-PC (99.5:0.5 mol %) in chloroform was deposited onto the surface with a glass syringe. The lipid-coated nanofibrillar cellulose paper was placed in vacuum for 1 hour to drive off traces of solvent. The lipid coated substrate was then placed into a chamber containing 100 microliters of an aqueous solution containing 2 mM Ficoll 400. This concentration of Ficoll acts as an osmolyte that exerts an osmotic pressure greater than 1 kPa on the lipid layer. The lipid-coated nanopaper was incubated in this solution for 12 hours. No vesicles formed on the surface of the paper. Thus, when the osmotic pressure exerted on the amphiphile layer is greater than 1 kPa the amphiphile layer does not vesiculate in a Ficoll solution. The Ficoll 400 was then diluted to a concentration of 0.2 mM by adding 900 microliters of ultrapure water to the chamber. Vesicles formed within 1 minute of dilution. Thus vesicle formation was triggered by diluting the osmolyte to a concentration that results in an osmotic pressure below 1 kPa, which caused vesicles to form. All experiments were performed at room temperature.

Example 18: Delaying and then Triggering Vesicle Formation by Using Temperature In this example, a method to delay and then trigger vesiculation from an amphiphile-coated substrate in aqueous solution, using changes in temperature, is disclosed. To obtain the lipid-coated nanofibrillar cellulose substrate, a 9.5 mm diameter piece of the nanopaper, made as described above (Example 7), was cut out and then 10 μg 1,2-dipentadecanoyl-sn-glycero-3-phosphocholine:TopFluor-PC (99.5:0.5 mol %) in chloroform was deposited onto the surface with a glass syringe. The lipid-coated nanofibrillar cellulose paper was placed in vacuum for 1 hour to drive-off traces of solvent. The lipid coated substrate was then placed into a chamber containing 100 microliters of an aqueous solution containing 100 mM glucose at 25° C., and allowed to incubate for 5 hours. No vesicles were observed on the surface of the nanopaper after 5 hours. When the temperature was increased to 35° C., using a Peltier stage, vesicles formed within 1 minute of the solution reaching 35° C.

Example 19: Method for Applying an Amphiphile Solution to Substrates Through Aerosols, Sprays, Glass Dropper, Pipettes, Soaking A laboratory spray bottle was filled with 10 mL of a solution of 1 mg/mL 0DOPC:TopFluor-PC (99.5:0.5 mol %) in isopropanol, and a piece of cotton fabric 9.5 mm in diameter was sprayed with this solution for a duration of 1 sec. In another experiment, a piece of cotton fabric 9.5 mm in diameter was dipped into a 2 mL solution of 1 mg/mL 0DOPC:TopFluor-PC (99.5:0.5 mol %) in isopropanol. In both cases, the substrate was allowed to soak for 2 minutes and was then removed and allowed to dry.

In additional experiments, 10 microliters of a solution of 1 mg/mL 0DOPC:TopFluor-PC (99.5:0.5 mol %) in isopropanol was deposited on cotton fabric using using a glass dropper or by using a lint roller. All experiments were performed at room temperature.

Example 20: Formation of Vesicles on Nanostructured Cellulose Surfaces

Cellulose filter papers are sheets of randomly percolated cellulose fibers that clarify liquids that flow through them by trapping suspended particulates in micrometer-sized tortuous pores. Alava & Niskanen (2006) *Reports Prog. Phys.* 69:669-723; Smook, G., *Handbook for Pulp and Paper Technologists*, Tappi press, 2016. Due to the inherent tortuosity of these papers, many of the GUVs that form on cellulose fibers remain trapped in the filter paper. Kresse et al. (2016) *ACS Appl. Mater. Interfaces* 8:32102-32107; Li et al. (2018) *Biomacromolecules* doi:10.1021/ascs.biomac.7b01645; Pazzi et al. (2019) *Langmuir* 35:7798-7804. This example describes construction of a cellulose paper with smaller pores (nanocellulose paper), whose use minimizes GUV losses due to trapping and hence maximizes yields. For cellulose sheets formed by random percolation of fibers, fiber cross-over density and pore sizes correlate with the fiber size. Alva & Niskanen, supra. Accordingly, fabricating paper through the percolation of nanoscale fibers results in a nanostructured sheet of cellulose devoid of micrometer-scale pores that trap GUVs.

A nanostructured cellulose paper (nanocellulose, nanopaper) was fabricated for use as a substrate for vesicle formation (PAPYRUS) The properties of the nanocellulose and of the vesicles formed thereon were compared with those of cellulose filter paper and commercially available tracing paper.

Filter paper. Whatman Ashless Grade 42 Filter Paper (42.5 mm diameter, 200 μm thickness), was obtained from Thermo Fischer Scientific (Waltham, MA).

Fabrication of nanopaper. Nanopaper was made from nanocellulose pulp using solution casting in Petri dishes. Klemm et al., supra; Orsolini et al. (2015) *ACS Appl. Mater. Interfaces* doi:10.1021/acsami.5b08308; Zhao et al. (2017) *Nanoscale Horizons* doi:10.1039/C7NH00104E. A 3% (w/v) aqueous slurry of slurry of nanofibrillated cellulose was obtained from the University of Maine Process Development Center. A 150 mm diameter glass Petri dish was filled with 60 mL of a 0.7 wt % aqueous suspension of nanocellulose. Klemm et al., supra; Orsolini et al. (2015) *ACS Appl. Mater. Interfaces* doi:10.1021/acsami.5b08308; Zhao et al. (2017) *Nanoscale Horizons* doi:10.1039/C7NH00104E. The Petri dish was placed in a 65° C. oven for 2 hours to evaporate the water. The resultant dry nanopaper appeared as a thin and transparent sheet with small wrinkles due to the rapid evaporation rate. To smooth out the wrinkles for depositing lipids, the Petri dish was filled with 60 mL of ultrapure water and the water was allowed to slowly evaporate overnight (approximately 12 hours) under ambient conditions. The smoothing step was repeated once more to obtain a smooth piece of nanopaper. Nanocellulose paper fabricated in this fashion was transparent, providing a visual indicator that the paper had minimal air-filled pores that scatter light. Huang et al. (2013) *ACS Nano* 7:2106-2113; Xu et al. (2016) *Nanoscale* 8:12294-12306.

Tracing paper. There is added convenience associated with using widely-available commodity-scale commercial substrates. Since a signature of a densely-packed paper with minimal pores is transparency to light, artist-grade tracing paper (obtained from Amazon, Seattle, WA) was selected as an additional substrate from the myriad extant commercial paper and pulp products. Smook, supra.

Characterization of paper surfaces. The surfaces of filter paper, lab-made nanocellulose paper (produced as described above), and commercial tracing paper were characterized by scanning electron microscopy (SEM) at the micrometer and nanometer length scales. SEM images of the dry substrates were obtained using a field emission scanning electron microscope (GeminiSEM 500, Zeiss, Germany). The substrates were cut into small 2×2 mm squares and mounted on aluminum stubs using double-sided copper tape. A piece of copper tape was placed on top of the substrate at one edge and was connected to the stub to create a conduction path to minimize charging at the surface. The beam accelerating voltage was set to 1 kV. An Everhart-Thornley secondary electron detector was used to collect the secondary electrons that scattered from the surface. The lower magnification images were captured with a lateral pixel resolution of 1.09 μm/pixel [1120 μm×840 μm (1024 pixels×768 pixels)], and the higher magnification images were captured with a lateral pixel resolution of 45 μm/pixel [22.76 μm×17.07 μm (1024 pixels×768 pixels)].

FIGS. 20A-20C show SEM images of the surfaces of the papers at low magnification. As noted previously (Kresse et al. (2016) *ACS Appl. Mater. Interfaces* 8:32102-32107; Pazzi et al. (2019) *Langmuir* 35:7798-7804), large irregular pores that ranged from several micrometers to several hundreds of micrometers in diameter dotted the surface of filter paper (FIG. 20A). In contrast, the surface of the lab-made nanocellulose paper was free of micrometer scale pores and appeared smooth on the micrometer scale (FIG. 20B). The surface of the tracing paper was also free of micrometer scale pores, but exhibited flattened cellulose fibers (indicated by white arrows) on its surface (FIG. 20C). The surface density of cellulose, calculated from the SEM images, was ~90% for filter paper, and ~100% for lab-made nanocellulose paper and commercial tracing paper. These results confirm that both the lab-made nanocellulose paper and the commercial tracing paper meet the desired criteria for a nanostructured cellulose paper that is free of micrometer-scale pores.

Higher magnification images, shown in FIGS. 20D-20F, revealed that all the papers, including the micrometer-scale fibers of the cellulose filter paper, were composed of fibrillar nanocellulose. Nanoscale pores were present between the nanocellulose fibers (arrows in FIGS. 20D-20F. Thus, filter paper is porous at multiple scales while lab-made nanocellulose paper and commercial tracing paper have nanoscale porosity.

Preparation of papers for vesicle formation. G42 filter paper, Nanocellulose paper and tracing paper substrates were prepared for vesicle formation by soaking in chloroform, with gentle agitation, for 30 minutes. The chloroform was discarded and, after a second 30 minute chloroform soak with gentle agitation, the substrate was removed and the chloroform allowed to evaporate. After evaporation of the chloroform, the substrate was placed in ultrapure water for 30 minutes; the water discarded, and a second water soak was conducted. After the second water soak, the substrate was removed to a glass petri dish, which was incubated at 65° C. for two hours. Once dried, the papers were stored at room temperature. Papers treated in this fashion ("cleaned" papers) maintained their structure and did not wrinkle significantly.

Vesicle formation. Vesicles were formed on nanostructured papers by depositing 10 μL of a 1 mg/ml solution of the zwitterionic phospholipid dioleoyl-sn-glycero-3-phosphocholine (DOPC) in chloroform onto the cellulose substrates. The chloroform was allowed to evaporate ambiently before remaining traces of solvent were removed by placing the substrates in a vacuum chamber for at least 1 hour. After removal from the vacuum chamber, 150 μL of a 100 mM sucrose solution was deposited onto the surfaces of the dried substrates and incubated under ambient conditions for 2 hours.

Imaging. For in situ confocal microscopy imaging of the vesicles on the substrates, the lipid-coated substrates, after two hours of vesicle growth, were placed in PDMS gaskets that had been affixed to glass slides (inner diameter× height=12×1 mm) and were hydrated in 150 μL of growth buffer. The chamber was sealed with a glass cover slip and confocal images were obtained by collecting z-stack images using a 10× Plan-NeoFluar objective with a numerical aperture of 0.3. The imaged area was 850.19 μm×850.19 μm (2140 pixels×2140 pixels) and the pinhole was set to 1 Airy Unit, providing a confocal slice thickness of 5.86 μm. To obtain the depth-coded projections, areas of the vesicles on each substrate with dimensions of 200 μm width×200 μm length×88 μm height were selected, and a depth-color coding process was applied to the images using ImageJ (NIH, Bethesda, MD), which false-colored each slice a unique color and summed the slices together to create the depth-coded projections.

FIGS. 20G-20I show confocal images of lipid-coated filter paper, lab-made nanocellulose paper, and tracing paper after 2 hours of incubation in a 100 mM solution of sucrose. The confocal images are at the same scale as the low magnification SEM images (FIGS. 20A-20C) providing spatial correlation of the configuration of the GUVs with the microstructure of the paper surfaces. GUVs formed as a dense layer that covered the entire surface of the lab-made nanocellulose paper (FIG. 20H) and commercial tracing paper (FIG. 20I). The GUVs were stratified in the axial direction by size: smaller GUVs were present closer to the surface of the paper and larger GUVs were located further away from the surface. All the GUVs however had tethers to the lipid film on the nanostructured paper substrate. On regular filter paper, GUVs were only present on the discrete micrometer-scale fibers including on fibers deep within the filter paper (FIG. 20G). The nanocellulose paper and tracing paper surfaces had GUVs of a wide range of sizes from 1 μm up to supergiant vesicles ~150 μm in diameter. On regular filter paper, GUVs larger than 60 μm were extremely rare.

Observations of the dynamics of vesicle formation (by time-lapse photography) on the surfaces of both the lab-made nanocellulose paper and tracing paper showed that large vesicles formed due to the merging of vesicular buds on the contiguous areas of the film of lipids. Since the lipid films are on discrete micrometer-sized cellulose fibers on filter paper, GUV diameters were limited to approximately the diameter of the fibers on filter paper. Pazzi & Subramaniam (2018) *Langmuir* 35:7798-7804. This result shows the importance of the contiguity of the lipid films for obtaining GUVs of larger diameters.

Figure 21:
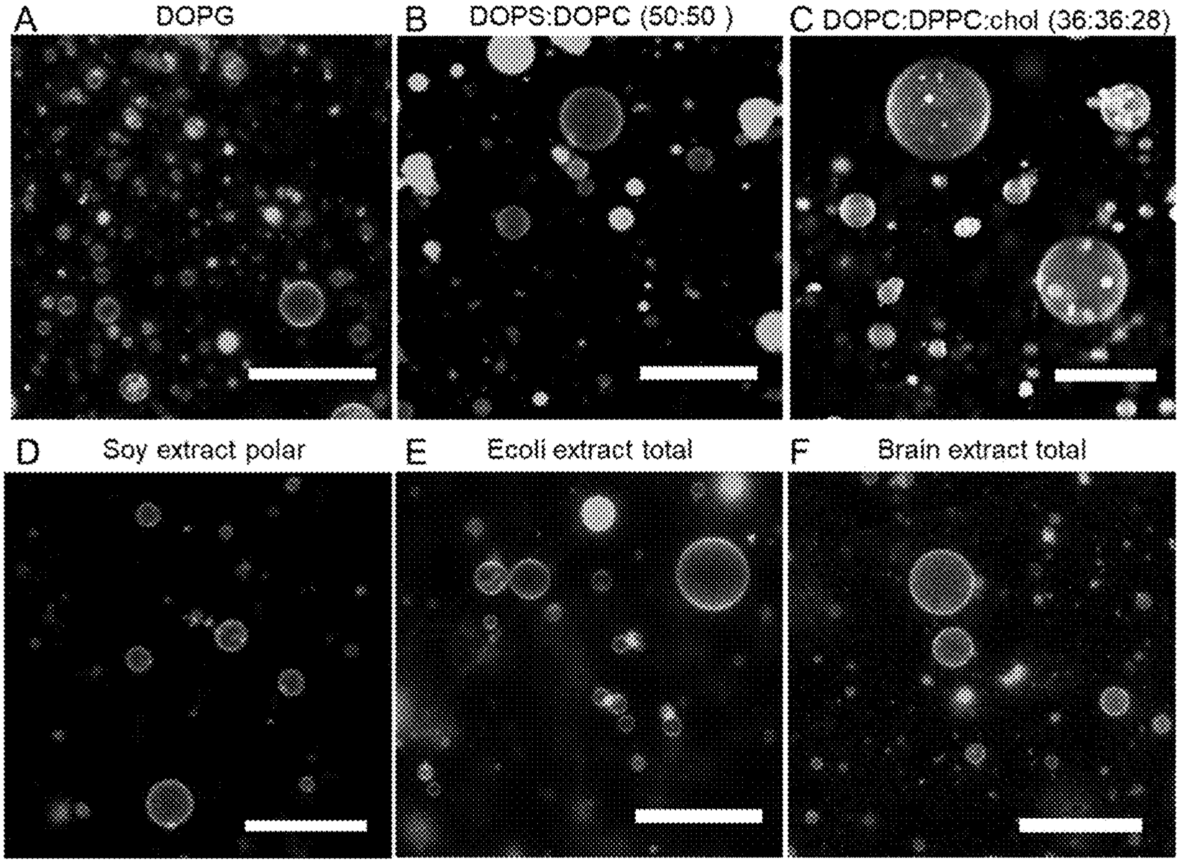

Similar to filter paper, lab-made nanocellulose paper and commercial tracing paper promoted the formation of GUVs from a wide variety of amphiphile types such as fatty acids, phospholipids, amphiphilic diblock and triblock copolymers and complex mixtures including extracts of plasma membranes and lipid compositions that require high growth temperatures (FIG. 21).

Example 21: Comparison of GUVs Formed on Different Substrates in Low Salt and High Salt Solutions The methods for vesicle formation described herein (denoted "PAPYRUS") on nanostructured papers and other types of cellulose were compared to existing thin-film hydration methods for vesicle formation. these included electroformation on ITO-coated glass slides, gel-assisted hydration on agarose-covered glass slides, and a modified form of gentle hydration on glass slides.

The comparisons were conducted under three conditions: (1) growth of GUVs using DOPC in low salt solutions (zwitterionic membranes in low salt solutions), (2) growth of GUVs using DOPC in high salt solutions (zwitterionic membranes in high salt solutions), and (3) growth of GUVs using a mixture of 97 mol % DOPC doped with 3 mol % PEG2000-PE in high salt solutions (PEG-stabilized membranes in high salt solutions). These particular conditions were chosen because (a) most of the data available on the growth of GUVs is on GUVs grown in low salt solutions (Walde et al. (2010) *ChemBioChem* 11:848-865; Stein et al. (2017) *Frontiers in Physiology* 8:1-16), (b) growth of GUVs in high salt solutions having an ionic strength corresponding to concentration of ions in physiological fluids is highly desirable and is known to be challenging, and (c) PEG-modified lipids are reported to increase the yields of GUVs in high salt solutions. Yamashita et al. (2002) *Biochim. Biophys.* 1561:129-134.

For low salt conditions, vesicles were formed in 100 mM sucrose. For high salt conditions (±PEG), vesicles were formed in standard phosphate buffered saline (standard PBS: 137 mM sodium chloride, 2.7 mM potassium chloride, 10 mM sodium phosphate, pH 7.4-7.6) supplemented with 100 mM sucrose. For each technique, five independent repeats were conducted (N=5) to allow statistical testing to account for sample-to-sample variations. Statistical significance was determined by performing one-way analysis of variance (ANOVA) on the fractional yields of GUVs measured from the five independent repeats per technique (group) for each of the three conditions. If ANOVA showed a statistically significant difference, Tukey's Honestly Significant Difference (HSD) post-hoc tests were conducted between the groups. One-way ANOVAs and post-hoc HSD tests were also performed to determine the statistical significance of the differences in fractional yields of the techniques under the three different conditions of growth (low salt, high salt and high salt/PEG). See Tables 6-17.

For the low salt condition, the following methods and substrates were used: PAPYRUS on filter paper, PAPYRUS on nanocellulose paper, PAPYRUS on tracing paper, PAPYRUS on dextran-tracing paper, electroformation on ITO-coated glass slides, gel-assisted hydration on agarose-covered glass slides, and modified gentle hydration on glass slides. PAPYRUS on filter paper, electroformation, and gel-assisted hydration were performed as described. Pazzi et al. (2018) *Langmuir* 35:7798-7804; Walde et al. (2010) *ChemBioChem* 11:848-865; Stein et al. (2017) supra; Horger et al. (2009) J. Amer. Chem. Soc. 131:1810-1819.

Dextran tracing paper. Tracing paper was doped with dextran (dextran-tracing paper) to mimic the dissolution of polymers from the insoluble nanocellulose matrix. The dextran-tracing paper was fabricated so that the dextran concentration on the surface of the paper approximated the surface concentration of agarose molecules on the surface of the glass cover slips used for agarose gel-assisted hydration. Low melting temperature agarose has an average molecular weight of 100,000 (Roberts et al. (2011) *J. Biomed. Mater. Res.—Part B Appl. Biomater.* 99B:158-169). Due to its porosity, a piece of tracing with an area equivalent to that of a glass coverslip (22 mm×22 mm) absorbs ~120 μL of water. Accordingly, 420 μL of a 1% (w/v) solution (in ultrapure water) of dextran (MW 100,000) was deposited onto cleaned pieces of tracing paper (i.e., tracing paper washed twice each with chloroform and water, as described in Example 20). The coated sheets of tracing paper were placed onto a sheet of Parafilm® and moved to a hot plate set at 40° C. where the paper was allowed to dehydrate for 3 hours.

PAPYRUS on filter paper, nanocellulose, tracing paper and dextran-tracing paper. Filter paper (Whatman G42), nanostructured cellulose (nanocellulose or nanopaper) and tracing paper were fabricated and cleaned as described in Example 20. Circular disks with a diameter of 9.5 mm of each of the four cellulose substrates (G42 filter paper, nanocellulose paper, tracing paper and dextran tracing paper) were punched out from the cleaned cellulose substrates using a circle hole punch (EK Tools Circle Punch, ⅜ in.). Lipids were deposited on the substrates by spreading 10 μL of the lipid solution onto the substrates and the lipid-coated substrates were placed into a standard vacuum desiccator for 1 hour to remove traces of solvent. Then the lipid-coated substrates were moved into individual wells in a 48-well plate. With a pipette, 150 μL of a 100 mM sucrose solution (low salt or high salt) was slowly expelled at the bottom corner of the well to fully immerse the substrate in solution. The lipid-coated substrates were allowed to incubate in the solution for 2 hours. To harvest the vesicles from the substrate, the 150 μL of solution was gently aspirated with a cut pipette tip 6 times. Excessive aspiration was avoided since the large vesicles are more susceptible to breakage from the shear forces, and unlike on filter paper or cotton fabric, the vesicles are more easily detached. In addition, during aspiration, the pipette tip was not brought into contact with the surface; which minimizes the removal of nanotubes or other unwanted lipid aggregates from the substrate.

Electroformation. Electroformation was conducted essentially as described. Herold et al. (2012) *Langmuir* 28:5518-5521. Indium tin oxide (ITO) coated-glass slides (25×25 mm squares, surface resistivity of 8-12 Ω/sq) were obtained from Sigma-Aldrich (St. Louis, MO). Briefly, 10 μL of lipid solution was deposited onto a 9.5 mm diameter circular area at the center of a clean indium tin oxide (ITO)-coated glass slide. The lipid-coated ITO-coated glass slide was then placed in a standard vacuum desiccator for 1 hour to remove traces of solvent. A circular PDMS (polydimethylsiloxane) gasket (inner diameter×height=12×1 mm) was affixed to the surface of the slide to construct a barrier around the lipid film, forming a chamber. Next, 150 μL of a solution (low salt or high salt) was added inside the gasket and a second ITO-coated glass slide was placed atop the gasket to form a closed-sandwiched chamber. The ITO surfaces were connected to the leads of a function generator (33120A Agilent) with conductive copper tape. A sinusoidal AC field at a field strength of 1.5 V/mm peak-to-peak and frequency of 10 Hz was then applied for 2 hours. After completion of growth, the chamber was disassembled by gently removing the top ITO slide. GUVs were detached from the surface of the slide by gently aspirating the solution within the chamber using a cut pipette tip.

ITO-covered slides degrade with each use, resulting in lower yields and smaller vesicle sizes, and thus require a mild annealing to reverse the effects of aging. Herold et al., supra. (This rapid degradation of an expensive substrate is a further disadvantage of electroformation.) Before use, ITO-covered slides were cleaned by sonicating for 10 minutes, sequentially, in acetone, ethanol and ultrapure water. The slides were then dried and annealed in air at 150° C. for 20 minutes.

Gel-assisted hydration. Gel-assisted hydration was performed essentially as described. Horger et al. (2009) *J. Amer. Chem. Soc.* 131:1810-1819. Briefly, low gelling temperature agarose powder (congealing temperature 26-30° C.) was dissolved at a concentration of 1% (w/v) in ultrapure water. Once the agarose was dissolved, 300 μL of the agarose solution was spread onto square glass cover slips (22 mm×22 mm) that were placed on Parafilm®. The coated glass cover slips were moved to a hot plate set to 40° C. where the agarose gel was allowed to dehydrate for 3 hours. Once the agarose gel was dehydrated, 10 μL of lipid solution was spread onto a 9.5 mm diameter area of the agarose film, and the film was placed under vacuum for 1 hour. To hydrate, a circular PDMS ring (inner diameter×height=12×1 mm) was affixed onto the agarose film, 150 μL of solution (low salt or high salt) was added, and the chamber was carefully covered with a glass cover slip.

Modified gentle hydration. Ten microliters of a 1 mg/ml solution of DOPC:TopFluor-PC (99.5:0.5 mol %) lipid, in neat chloroform, was spread onto a 9.5 mm diameter circular area at the center of a premium plain glass microscope slide (75 mm×25 mm) using a glass syringe (Hamilton). The lipid mixture was spread gently with the needle of the syringe to obtain a thin film with a greenish hue. The lipid-coated glass slide was placed in a standard vacuum desiccator for 1 hour to remove traces of solvent. A circular PDMS gasket (inner diameter×height=12×1 mm) was affixed to the slide to construct a barrier around the lipid film. Next, 150 μL of solution (low salt, high salt, or high salt/PEG) was added and the chamber was carefully covered with a glass cover slip. After 2 hours of vesicle growth, the cover slip was removed, and GUVs were detached from the surface of the slides by gently aspirating the solution using a cut pipette tip. The GUV suspensions were stored in a microcentrifuge tube until further use.

Conventional gentle hydration is typically performed with up to 20 mol % of anionic lipids and incubation times of up to 24-48 hours. Akashi et al. (1996) *Biophys. J* 71:3242-3250. The use of a shorter incubation time for modified gentle hydration in these experiments provides a baseline measure for the spontaneous formation of GUVs from zwitterionic and PEG-modified multibilayer stacks on an inert and impermeable surface.

Stepped PAPYRUS. For formation of vesicles under high salt conditions, an additional two-step method ("stepped PAPYRUS") was used in which deposition occurred under low salt conditions (100 mM sucrose) and the ionic strength was then increased to high salt conditions (PBS). Steps were similar to the procedures for vesicle formation on tracing paper except the paper was hydrated in 100 mM sucrose on a glass slide in a circular PDMS gasket (inner diameter× height=12×1 mm) for 10 minutes. After this initial step, 7.5 μL of 20×PBS stock solution was gently expelled beneath the paper and a glass cover slip was placed to cover the chamber and continue growth (in this second step) for 2 hours.

Characterization of GUVs. GUVs formed under low salt, high salt and high salt/PEG conditions were harvested from all substrates in identical fashion and imaged by confocal microscopy. GUVs with diameters ranging from 1 μm up to 150 μm were observed in the harvested solutions. Qualitatively, the number of isolated GUVs harvested from the substrates in high salt conditions appeared lower than the number of GUVs harvested from the substrates in low salt conditions. In high salt solutions, flocs of GUVs were present in populations harvested from agarose gel, dextran-tracing paper, and stepped-PAPYRUS. The number of flocs were reduced in populations of GUVs made using PEG-modified lipids. Flocs, which were easily identifiable, were not included in the quantitative analysis.

Size comparisons. Histograms of the diameters of GUVs formed under certain of the different conditions described above are shown in FIG. 22. The shapes of the GUV size histograms for vesicles made by PAPYRUS on nanostructured paper and by gentle hydration were similar, as were the histograms for sizes of vesicles made by all other techniques tested: asymmetric with a prominent right tail. None of the techniques resulted in the production of a monodisperse population of GUVs. The number of GUVs in each bin decreased monotonically as a function of increasing diameter.

The median diameter of the GUVs ranged between 2 μm to 3 μm. GUVs larger than 15 micrometers made up less than 2% of the population of GUVs obtained from all the techniques. This fraction, translates to 1,551 GUVs per μg lipid for PAPYRUS on nanocellulose paper, 1,717 GUVs per μg lipid for PAPYRUS on tracing paper, 1,301 GUVs per μg lipid for agarose gel-assisted hydration, 1,147 GUVs per μg lipid for electroformation, and 468 GUVs per μg lipid for gentle hydration. Compared to the distribution of sizes of GUVs grown in low salt solutions, a lower number of GUVs of larger sizes were obtained after vesicle formation in high salt solutions.

PAPYRUS on tracing paper produced higher or equal numbers of GUVs in all bins compared to the other techniques.

Calculation of Fractional yield. The moles of lipid that are deposited on the substrate ($mol_d$) is determined by $$mol_d = \frac{M}{m}$$

where M is the mass of deposited lipid in grams, and m is the molecular weight.

From this amount of lipids, N GUVs are formed and harvested into a volume of solution $V_h$. The moles of lipids in the membrane of a spherical giant unilamellar vesicle i of area $A_1$ is:

$$mol_i = \frac{2\left(4\pi\left(\frac{d_i}{2}\right)^2\right)}{N_A A_{hg}}$$

In this equation, $N_A$ is Avagadro's number, $A_{hg}$ is the lipid headgroup area, and $d_i$ is the diameter of vesicle i. The factor of 2 accounts for the fact that there are 2 lipid leaflets in a bilayer.

The total moles of lipid in N tGUVs from a harvested suspension is thus:

$$mol_{tot} = \frac{2\pi}{N_A A_{hg}} \sum_{i=1}^{N} (d_i)^2$$

Constants were collected and moved out of the summation.

Thus, the effective yield is $$Efficency = \frac{2\pi m}{N_A A_{hg} M} \sum_{i=1}^{N} (d_i)^2$$

For quantification of vesicle numbers and diameters, an aliquot of volume $V_{al}$ is taken from a harvested suspension $V_h$. The final expression for the efficiency is thus:

$$Efficency = \frac{2\pi m V_h}{N_A A_{hg} M V_{al}} \sum_{i=1}^{n} (d_i)^2$$

Note that the sum is now over the number of all vesicles counted in the imaging chamber, n. The efficiency is multiplied by 100 to provide a percentage. Accordingly, the fractional yield Y of GUVs, for each method, was obtained from the diameters of GUVs produced by that method using Equation 1:

$$Y = \frac{2\pi m V_h}{N_A A_{hg} M V_{al}} \sum_{i=1}^{n} (d_i)^2 \times 100\% \tag{1}$$

with M being the mass of lipid deposited on the substrate, m the molecular weight of the lipid, $V_{al}$ the volume of the aliquot in the imaging chamber, $V_h$ the volume of the harvested GUV suspension, n the number of GUVs in the imaging chamber, and $d_i$ the diameter of vesicle i. FIG. 23 shows a three-dimensional bar plot of the mean fractional yields of GUVs obtained from each of the techniques tested under the three conditions (low salt, high salt and high salt/PEG).

Fractional yields under low salt conditions. The mean fractional yields for vesicles having zwitterionic membranes (i.e., vesicles made using DOPC) in low salt solutions are shown in the rear-most set of bars in FIG. 23. For modified gentle hydration, the mean fractional yield was 16±1%. In ascending order of fractional yields, the mean yields from PAPYRUS on filter paper, electroformation, PAPYRUS on dextran-tracing paper, agarose gel-assisted hydration, PAPYRUS on nanocellulose paper, and PAPYRUS on tracing paper were 5±1%, 21±2%, 29±3%, 29±5%, 30±5%, and 30±4% respectively (FIG. 23). A balanced one-way ANOVA showed that the differences between at least one of the mean fractional yields was statistically significant [$F(6, 28)=39$, $p=2.49\times10^{-12}$]. HSD post-hoc tests showed that the higher mean fractional yields of GUVs obtained through agarose gel-assisted hydration ($p=3.79\times10^{-5}$), PAPYRUS on nanocellulose paper ($p=1.50\times10^{-5}$), PAPYRUS on tracing paper ($p=1.11\times10^{-5}$), and PAPYRUS on dextran tracing paper ($p=8.83\times10^{-5}$) were statistically significant compared to gentle hydration. These results demonstrate quantitatively that, in low salt solutions, agarose gel-assisted hydration, PAPYRUS on nanocellulose paper, PAPYRUS on tracing paper, and PAPYRUS on dextran-tracing paper improves the yield of GUVs compared to the spontaneous vesiculation of multibilayer stacks of DOPC. See Tables 6 and 7.

The lower mean fractional yield of GUVS obtained by PAPYRUS on filter paper compared to modified gentle hydration was statistically significant ($p=2.45\times10^{-4}$). This result confirms the substantial effect that trapping exerts on the fractional yield of GUVs, as discussed in Example 20. Thus, use of papers and fabrics with large pores can retain vesicles, and the molecules that they encapsulate, within the paper. The mean fractional yield of GUVs obtained from PAPYRUS on tracing paper and PAPYRUS on nanopaper were statistically indistinguishable ($p=1.00$). This result confirms that the formation of GUVs on lab-made nanocellulose paper and commercial tracing papers, both of which are nanostructured cellulose papers with no micrometer scale pores, were similar. Further, the mean fractional yields of PAPYRUS on tracing paper, PAPYRUS on nanocellulose paper, PAPYRUS on dextran-tracing paper, and agarose gel-assisted hydration were statistically indistinguishable from each other.

Interestingly, electroformation did not provide a statistically significant higher yield than did gentle hydration (p=0.43) across the range of vesicle sizes considered to be GUVs (>1 μm). However, electroformation does produce a higher fraction of GUVs of larger diameters compared to gentle hydration. Furthermore, electroformation had a statistically significant lower fractional yield than agarose gel-assisted hydration (p=0.00681), PAPYRUS on nanopaper (p=0.00265), PAPYRUS on tracing paper (p=0.00191), and PAPYRUS on dextran tracing-paper (p=0.0169). This likely indicates that the electric field promotes merging of smaller vesicular buds to form GUVs of larger diameters. The total yield of GUVs obtained by electroformation is, however, similar to that obtained by gentle hydration. This result is notable since PAPYRUS on nanopaper, PAPYRUS on tracing paper, and PAPYRUS on dextran tracing-paper do not require costly conductive substrates, specialized electronic equipment, or access to electricity, and do not cause the peroxidation of lipids.

Fractional yields under high salt conditions. The mean fractional yields of GUVs for zwitterionic membranes in high salt solutions were significantly lower for all of the techniques (FIG. 23, middle row of bars). Many of the fractional yields were well below 5%. The mean fractional yield for gentle hydration was 0.8±0.8%, for electroformation was 1.1±0.5%, for PAPYRUS on tracing paper was 0.7±0.2%, for agarose gel-assisted hydration was 2.2±0.4%, for dextran-tracing paper was 2.1±1.2%, and for stepped-PAPYRUS was 5.6±2.0%. A balanced one-way ANOVA showed that the differences between at least one of the mean fractional yields was statistically significant [F(5, 24)=5.8, p=0.0012]. HSD post-hoc tests showed that only the higher mean fractional yield of stepped-PAPYRUS was statistically significant when compared to the other techniques. See Tables 8 and 9. Thus, in high salt solutions, none of electroformation, agarose-gel assisted hydration, PAPYRUS on dextran-tracing paper, and tracing paper hydrated directly in PBS provided an increased fractional yield of isolated GUVs compared to gentle hydration, a noteworthy contrast to the results obtained in low salt solutions.

Fractional yields under high salt/PEG conditions. Incorporating PEG-modified lipid into the membrane led to statistically significant increases in the mean fractional yields of isolated GUVs obtained in high salt solutions for all the techniques except for modified gentle hydration and PAPYRUS on tracing paper (FIG. 23, front-most set of bars). The mean fractional yields for gentle hydration, PAPYRUS on tracing paper, electroformation, agarose gel-assisted hydration, PAPYRUS on dextran-tracing paper, and stepped-PAPYRUS were 0.8±0.5%, 2.3±1.2%, 4.7±1.0% 10.4±2.1%, 7.7±1.6%, and 29.3±1.8%, respectively. A balanced one-way ANOVA showed that the differences between at least one of the mean fractional yields was statistically significant [F(5, 24)=197, p=$1.14\times10^{-18}$]. HSD post-hoc tests showed that all the techniques had statistically significant increases in yield of isolated GUVs compared to modified gentle hydration. See Tables 10 and 11. The yields of GUVs from agarose gel-assisted hydration and PAPYRUS on dextran-tracing paper were statistically indistinguishable (p-value=0.14). The higher yield obtained using these two techniques, compared to that obtained using PAPYRUS on tracing paper hydrated directly in PBS was statistically significant (p=$9.63\times10^{-7}$) (p=$4.58\times10^{-4}$). Note that the yield of PEG-modified GUVs from agarose gel-assisted hydration was 2.8 times lower than the yield in low salt-solutions (p=$7.29\times10^{-6}$). In contrast, the fractional yield between stepped-PAPYRUS on tracing paper in high salt solutions and PAPYRUS on nanostructured papers in low salt solutions were statistically indistinguishable (p-value=0.607). These results demonstrate that, among all techniques tested, PAPYRUS on nanostructured paper produced quantitatively higher yields in low salt solutions and stepped-PAPYRUS on nanostructured papers produced quantitatively higher yields in high salt solutions.

The bulky hydrophilic PEG chains attached to the headgroups of PEG-modified lipids are known to increase repulsive hydration forces between bilayers. A larger hydration repulsion force causes the equilibrium interlamellar spacing to increase in multibilayer stacks, though it is unclear if larger equilibrium spacings translates to increased vesicle formation. Use of PEG-modified lipids in gentle hydration, in which the dominant contribution to vesicle formation is interbilayer repulsion, did not result in statistically significant increases in the fractional yields of GUVs in high salt solutions compared to non-PEG modified lipids. Thus, the results indicate that increased hydration repulsion is insufficient to cause appreciable vesiculation when electrostatic repulsions are short-ranged, consistent with the observations of others. Shohda et al. (2015) *Biochem. Biophys. Reports* 3:76-82; Horger et al. (2009) *J Am. Chem. Soc.* 31:1810-1819.

In contrast, PEG-modified lipids increased the fractional yields of isolated GUVs for the agarose gel-assisted hydration, stepped-PAPYRUS, and dextran-tracing paper techniques. This increase in fractional yields correlated with reduced amounts of flocculated GUVs. These results indicate that PEG-modified lipids increase the yield of isolated GUVs in high salt solutions by acting as a steric corona that prevents membranes from flocculating. Israelachvili, J. N. *Intermolecular and Surface Forces: Third Edition* (2011). doi:10.1016/C2011-0-05119-0. Images of the surface of the substrate supports the view that the primary role of PEG in increasing the yields of isolated GUVs in high salt solutions is by preventing flocculation. For example, extensive regions of flocculated GUVs were apparent for zwitterionic membranes on tracing paper after addition of the concentrated stock of salts. The PEG-modified membranes on the other hand remained as isolated GUVs after addition of the concentrated stock solution of salts.

In conclusion, paper-abetteted lipid hydration on nanostructured papers results in the highest fractional yield of giant vesicles among extant techniques under both low salt and high salt conditions. Along with the quantitative improvements, nanostructured paper-based PAPYRUS is cost effective, does not require electrical power or specialized equipment, and is easy to implement both on the benchtop and at larger scales.

Example 22: Cost Comparison for Production of GUVs Using Different Thin Film Hydration Techniques Along with quantitatively superior yields under both low salt and high salt solutions, calculations of substrate costs reveal the significant advantages of using PAPYRUS on nanostructured paper for scaling up the production of GUVs. Note that to a first approximation, the production of GUVs scales as a function of the surface area of the substrate for all thin-film hydration techniques.

Substrate costs were calculated using the lowest posted prices from the websites of large multinational suppliers of scientific materials. FIG. 24 shows the substrate cost per vesicle for growth in low salt solutions and the substrate cost per vesicle for growth in high salt solutions. Nanopaper-based PAPYRUS has the lowest cost per vesicle of all sizes for growth in both low salt and high salt solutions. For example, producing a single 100 μm diameter GUV using electroformation and agarose gel-assisted hydration in low salt solutions costs USD 0.16 and USD 0.002, respectively. The cost is more than 100,000× lower for PAPYRUS on tracing paper (USD 0.0000013).

Example 23: Economics of Scaling Up the Production of GUVs Using Thin Film Hydration Techniques A prototypical example of producing 1 liter of artificial blood is used to estimate characteristic numbers and sizes of GUVs. A healthy adult male has approximately 5.5 L of blood which consists primarily of erythrocytes with a mean corpuscular volume (MCV) of 91 $\mu m^3$ and concentration of $4.92\times10^{12}$ erythrocytes/L. The MCV translates to an equivalent mean spherical diameter of 5.6 μm. Obtaining a liter of GUVs with a diameter between 5.0 and 5.9 μm at a concentration typical of blood using the gentle hydration technique requires a glass surface area of 790 $m^2$ at a cost of approximately USD 210,000 for growth in low salt solutions. Due to the lower yield, gentle hydration would require a glass surface area of 17,000 $m^2$ at a cost of approximately USD 4,600,000 if growth was conducted in physiological saline. (All substrate area and dollar amounts are rounded to 2 significant figures.) Electroformation would require a substrate area of 530 $m^2$ at a cost of approximately USD 20,000,000 for growth in low salt solutions and an area of 4,300 $m^2$ at a cost of approximately USD 98,000,000 for growth in physiological saline (i.e., high salt). If polymer contamination is acceptable, a liter of artificial blood produced through agarose-gel assisted hydration would require a substrate area of 620 $m^2$ at a cost of USD 190,000 for growth in low salt solutions and a substrate area of 1,300 $m^2$ and USD 400,000 for growth in physiological saline. Production using PAPYRUS on dextran-tracing paper has a lower substrate cost of USD 8,900 since both dextran and tracing paper are cheaper than low melting temperature agarose and glass cover slips.

Furthermore, the cost of producing artificial blood using PAPYRUS on nanostructured paper is several orders of magnitude lower than that of electroformation or agarose gel-assisted hydration. A liter of artificial blood would require a piece of tracing paper 250 $m^2$ in area at a cost of USD 190 for growth in sucrose, and an area of 210 $m^2$ at a cost of USD 160 for stepped-PAPYRUS in physiologically saline. Substrate cost alone disfavors gentle hydration, electroformation, and agarose gel-assisted hydration for producing GUVs at large scales.

In addition to being the least expensive single-use substrate, the high tensile strength of nanocellulose (Klemm et al. (2011) *Angew. Chemie—Int. Ed.* 50:5438-5466) makes tracing paper resilient to mechanical insults. FIG. 25 shows that a single piece of tracing paper can be cleaned and reused at least five times with no change in the fractional yield of the harvested GUVs. FIG. 26 shows that confocal images of vesicles formed on tracing paper after five cycles of vesicle growth were indistinguishable from images of vesicles formed during the first cycle. (See Example 6 for methods of cyclic growth.) Thus, the tracing paper could likely be reused many more than five times, further lowering fixed substrate costs. In contrast, ITO-coated slides degrade with each use and gel molecules have to be reapplied since they dissolve into solution.

TABLE 6

ANOVA table of mean fractional yields of GUVs obtained by different thin-film hydration techniques under low salt conditions

| Source | SS | df | MS | F | Prob > F, (p-value) |
|---|---|---|---|---|---|
| Columns | 2810.72 | 6 | 468.453 | 38.96 | 2.50E−12 |
| Error | 336.65 | 28 | 12.023 | | |
| Total | 3147.36 | 34 | | | |

TABLE 7 p-values from posthoc Tukey HSD tests of mean fractional yields of GUVs obtained by different thin-film hydration techniques under low salt conditions#

| Group 1 | Group 2 | p-value | |
|---|---|---|---|
| Gentle Hydration | Filter Paper | 0.000245 | *** |
| Gentle Hydration | Electroformation | 0.428 | NS |
| Gentle Hydration | Agarose Gel | 3.79E−05 | *** |
| Gentle Hydration | Dextran Tracing Paper | 8.83E−05 | *** |
| Gentle Hydration | Nanocellulose Paper | 1.50E−05 | *** |
| Gentle Hydration | Tracing Paper | 1.11E−05 | *** |
| Filter Paper | Electroformation | 1.18E−07 | *** |
| Filter Paper | Agarose Gel | 3.72E−08 | *** |
| Filter Paper | Dextran Tracing Paper | 3.73E−08 | *** |
| Filter Paper | Nanocellulose Paper | 3.71E−08 | *** |
| Filter Paper | Tracing Paper | 3.71E−08 | *** |
| Electroformation | Agarose Gel | 0.00769 | ** |
| Electroformation | Dextran Tracing Paper | 0.0169 | * |
| Electroformation | Nanocellulose Paper | 0.00313 | ** |
| Electroformation | Tracing Paper | 0.00231 | ** |
| Agarose Gel | Dextran Tracing Paper | 1.00 | NS |
| Agarose Gel | Nanocellulose Paper | 1.00 | NS |
| Agarose Gel | Tracing Paper | 1.00 | NS |
| Dextran Tracing Paper | Nanocellulose Paper | 0.993 | NS |
| Dextran Tracing Paper | Tracing Paper | 0.985 | NS |
| Nanocellulose Paper | Tracing Paper | 1.00 | NS |

#Techniques tested were PAPYRUS on nanocellulose paper, PAPYRUS on tracing paper, modified gentle hydration, agarose gel-assisted hydration, electroformation, and PAPYRUS on filter paper in low salt solutions.
NS not significant,
* $p < 0.05$,
** $p < 0.01$
*** $p < 0.0001$

TABLE 8

ANOVA table of mean fractional yields of GUVs obtained by different thin-film hydration techniques under high salt conditions

| Source | SS | df | MS | F | Prob > F (p-value) |
|---|---|---|---|---|---|
| Columns | 147.067 | 5 | 29.4134 | 5.79 | 0.0012 |
| Error | 122.011 | 24 | 5.0838 | | |
| Total | 269.078 | 29 | | | |

TABLE 9 p-values from posthoc Tukey HSD tests of mean fractional yields of GUVs obtained by different thin-film hydration techniques under high salt conditions#

| Group 1 | Group 2 | p-value | |
|---|---|---|---|
| Gentle Hydration | Tracing Paper | 1.00 | NS |
| Gentle Hydration | Agarose Gel | 0.722 | NS |
| Gentle Hydration | Dextran-Tracing Paper | 0.453 | NS |
| Tracing Paper | Agarose Gel | 0.687 | NS |
| Tracing Paper | Dextran-Tracing Paper | 0.419 | NS |
| Agarose | Dextran-Tracing Paper | 0.998 | NS |
| Stepped-Tracing Paper | Gentle Hydration | 0.000303 | *** |
| Stepped-Tracing Paper | Tracing Paper | 0.000263 | *** |
| Stepped-Tracing Paper | Agarose Gel | 0.0772 | NS |
| Stepped-Tracing Paper | Dextran-Tracing Paper | 0.182 | NS |

#Techniques tested were PAPYRUS on nanocellulose paper, PAPYRUS on tracing paper, modified gentle hydration, agarose gel-assisted hydration, electroformation, and PAPYRUS on filter paper in low salt solutions.
NS not significant,
* $p < 0.05$,
** $p < 0.01$
*** $p < 0.0001$

TABLE 10

ANOVA table of mean fractional yields of GUVs obtained by different thin-film hydration techniques under high salt/PEG conditions

| Source | SS | df | MS | F | Prob > F, (p-value) |
|---|---|---|---|---|---|
| Columns | 2718.15 | 5 | 543.63 | 197.02 | 1.15E−18 |
| Error | 66.22 | 24 | 2.759 | | |
| Total | 2784.37 | 29 | | | |

TABLE 11 p-values from posthoc Tukey HSD tests of mean fractional yields of GUVs obtained by different thin-film hydration techniques under high salt/PEG conditions#

| Group 1 | Group 2 | p-value | |
|---|---|---|---|
| Gentle Hydration | Tracing Paper | 0.660 | NS |
| Gentle Hydration | Agarose Gel | 5.73E−08 | *** |
| Gentle Hydration | Dextran-Tracing Paper | 1.15E−05 | *** |
| Tracing Paper | Agarose Gel | 9.63E−07 | *** |
| Tracing Paper | Dextran-Tracing Paper | 4.58 − 04 | *** |
| Agarose | Dextran-Tracing Paper | 0.137 | NS |
| Stepped-Tracing Paper | Gentle Hydration | 2.07E−08 | *** |
| Stepped-Tracing Paper | Tracing Paper | 2.07E−08 | *** |
| Stepped-Tracing Paper | Agarose Gel | 2.07E−08 | *** |
| Stepped-Tracing Paper | Dextran-Tracing Paper | 2.07E−08 | *** |

#Techniques tested were PAPYRUS on nanocellulose paper, PAPYRUS on tracing paper, modified gentle hydration, agarose gel-assisted hydration, electroformation, and PAPYRUS on filter paper in low salt solutions.
NS not significant,
* $p < 0.05$,
** $p < 0.01$
*** $p < 0.0001$

TABLE 12

ANOVA table and table of posthoc Tukey HSD tests of mean fractional yield of GUVs by modified gentle hydration under different conditions#
Gentle Hydration

| Source | SS | df | MS | F | Prob > F, (p-value) |
|---|---|---|---|---|---|
| Columns | 774.69 | 2 | 387.34 | 960.79 | 5.71E−14 |
| Error | 4.84 | 12 | 0.403 | | |
| Total | 779.53 | 14 | | | |

| Group 1 | Group 2 | P-value | |
|---|---|---|---|
| DOPC in sucrose | DOPC in PBS | 2.67E−09 | *** |
| DOPC in sucrose | PEG-lipid in PBS | 2.67E−09 | *** |
| DOPC in PBS | PEG-lipid in PBS | 0.695 | NS |

#sucrose: low salt conditions; PBS: high-salt conditions;
NS not significant,
* $p < 0.05$,
** $p < 0.01$
*** $p < 0.0001$.

TABLE 13

ANOVA table and table of posthoc Tukey HSD tests of mean fractional yield of GUVs by electroformation under different conditions#
Electroformation

| Source | SS | df | MS | F | Prob > F, (p-value) |
|---|---|---|---|---|---|
| Columns | 1071.87 | 2 | 535.934 | 266.03 | 1.15E−10 |
| Error | 24.17 | 12 | 2.015 | | |
| Total | 1096.04 | 14 | | | |

| Group 1 | Group 2 | p-value | |
|---|---|---|---|
| DOPC in sucrose | DOPC in PBS | 2.77E−09 | *** |
| DOPC in sucrose | PEG-lipid in PBS | 4.22E−09 | *** |
| DOPC in PBS | PEG-lipid in PBS | 0.00414 | ** |

#sucrose: low salt conditions; PBS: high-salt conditions;
NS not significant,
* $p < 0.05$,
** $p < 0.01$
*** $p < 0.0001$.

TABLE 14

ANOVA table and table of posthoc Tukey HSD tests of mean fractional yield of GUVs by gel-assisted hydration under different conditions#
Agarose Gel-Assisted Hydration

| Source | SS | df | MS | F | Prob > F, (p-value) |
|---|---|---|---|---|---|
| Columns | 1821.11 | 2 | 910.55 | 70.3 | 2.36E−07 |
| Error | 155.43 | 12 | 12.952 | | |
| Total | 1976.53 | 14 | | | |

| Group 1 | Group 2 | p-value | |
|---|---|---|---|
| DOPC in sucrose | DOPC in PBS | 2.22E−07 | *** |

TABLE 14-continued

ANOVA table and table of posthoc Tukey HSD tests of mean fractional yield of GUVs by gel-assisted hydration under different conditions#
Agarose Gel-Assisted Hydration

| | | | |
|---|---|---|---|
| DOPC in sucrose | PEG-lipid in PBS | 7.29E−06 | *** |
| DOPC in PBS | PEG-lipid in PBS | 0.0192 | * |

#sucrose: low salt conditions; PBS: high-salt conditions;
NS not significant,
* $p < 0.05$,
** $p < 0.01$
*** $p < 0.0001$.

TABLE 15

ANOVA table and table of posthoc Tukey HSD tests of mean fractional yield of GUVs by PAPYRUS on dextran-tracing paper under different conditions#
Dextran Tracing Paper

| Source | SS | df | MS | F | Prob > F, (p-value) |
|---|---|---|---|---|---|
| Columns | 1929.77 | 2 | 964.89 | 156.41 | 2.54E−09 |
| Error | 74.03 | 12 | 6.169 | | |
| Total | 2003.8 | 14 | | | |

| Group 1 | Group 2 | p-value | |
|---|---|---|---|
| DOPC in sucrose | DOPC in PBS | 5.56E−09 | *** |
| DOPC in sucrose | PEG-lipid in PBS | 4.52E−09 | *** |
| DOPC in PBS | PEG-lipid in PBS | 0.0123 | * |

#sucrose: low salt conditions; PBS: high-salt conditions;
NS not significant,
* $p < 0.05$,
** $p < 0.01$
*** $p < 0.0001$.

TABLE 16

ANOVA table and table of posthoc Tukey HSD tests of mean fractional yield of GUVs by one-step PAPYRUS on tracing paper under different conditions#
Tracing Paper One Step

| Source | SS | df | MS | F | Prob > F, (p-value) |
|---|---|---|---|---|---|
| Columns | 2730.55 | 2 | 1365.28 | 237.8 | 2.22E−10 |
| Error | 68.89 | 12 | 5.74 | | |
| Total | 2799.45 | 14 | | | |

| Group 1 | Group 2 | p-value | |
|---|---|---|---|
| DOPC in sucrose | DOPC in PBS | 3.16E−09 | *** |
| DOPC in sucrose | PEG-lipid in PBS | 3.56E−09 | *** |
| DOPC in PBS | PEG-lipid in PBS | 0.660 | NS |

#sucrose: low salt conditions; PBS: high-salt conditions;
NS not significant,
* $p < 0.05$,
** $p < 0.01$
*** $p < 0.0001$.

TABLE 17

ANOVA table and table of posthoc Tukey HSD tests of mean fractional yield of GUVs by stepped PAPYRUS on tracing paper under different conditions#
Stepped Tracing Paper

| Source | SS | df | MS | F | Prob > F, (p-value) |
|---|---|---|---|---|---|
| Columns | 1696.32 | 2 | 848.16 | 237.8 | 2.22E−10 |
| Error | 107.24 | 12 | 8.936 | | |
| Total | 1803.56 | 14 | | | |

| Group 1 | Group 2 | p-value | |
|---|---|---|---|
| DOPC in sucrose | DOPC in PBS | 1.15E−07 | *** |
| DOPC in sucrose | PEG-lipid in PBS | 0.849 | NS |
| DOPC in PBS | PEG-lipid in PBS | 1.91E−07 | *** |

#sucrose: low salt conditions; PBS: high-salt conditions;
NS not significant,
* $p < 0.05$,
** $p < 0.01$
*** $p < 0.0001$.

Example 24: Loading of Hydrophilic Molecules into Vesicles

Ten μl of a 1 mg/ml solution of FITC-dextran and FITC was deposited on a 9.5 mm diameter circle of cleaned tracing paper and the paper was allowed to dry. 19 μl of a 1 mg/ml solution of DOPC was applied to the paper and the paper was again allowed to dry. The paper was then placed in 150 μl of 100 mM sucrose for two hours. Vesicles were harvested from the paper by gentle fluid flow from a pipette tip and viewed by fluorescence confocal microscopy.

FIG. 27A shows a schematic of the procedure. FIG. 27B shows confocal images of vesicles with fluorescent lumens, indicating that the FITC-loaded dextran was incorporated into vesicles.

Example 25: Functionalizing the Surface of Fabric Fibers with Water Soluble Compounds that are Loaded into the Vesicles and that Remain Bound to the Fibers after Repeated Hydration and Dehydration Steps In this example, a fabric was functionalized with a water-soluble molecule (FITC-dextran) before a solution of amphiphile is deposited onto the fabric. The fabric was then exposed to water, dried, and then exposed to water again. The process was repeated 3 times. The fabric was then imaged with a confocal microscope to determine if the vesicles that are formed entrap FITC-dextran.

Accordingly, 10 μL of a 1 mg/mL solution of FITC-Dextran in water was placed onto a circular piece of silk fabric 9.5 mm in diameter and allowed to dry for 30 minutes on a hot plate set at 40° C. Then 10 μL of a 1 mg/mL solution of DOPC: Rhodamine-PE (99.5:0.5 mol %) in chloroform was placed onto the dry dextran-covered silk. The chloroform was allowed to evaporate. The dry silk fabric was then wetted with 50 μL of water and allowed to incubate for 10 minutes and then imaged with a confocal microscope.

FIG. 28A shows the presence of many dextran-filled vesicles on the fibers of silk. The concentration of dextran inside the vesicles was much higher than the concentration of dextran in the surrounding water as evidenced by the high fluorescence intensity inside the vesicles. The water was allowed to evaporate to dryness for 30 minutes, before 50 μL of water was added to the fabric and allowed to incubate for 10 minutes and then imaged with a confocal microscope. Vesicles reformed on the fibers and entrapped the dextran as before (FIG. 28B). The drying and rehydration process was repeated a third time and vesicles again reformed on the fibers (FIG. 28C). Thus, vesicles that entrap high concentrations of dextran (a hydrophilic, water-soluble molecule) remain associated with the fibers of the fabric at each hydration step.

Example 26: Controlling the Size of Vesicles and their Release from Substrates by Controlling the Tortuosity of the Pores on the Substrates In this example, the number of vesicles that are released from the substrate was controlled by treating the surface of regular filter paper with different surface concentrations of nanocellulose.

Pure filter paper is a surface with 0 $g/mm^2$ of nanocellulose and pure nanopaper is a surface with 10.4 $g/mm^2$ of nanocellulose. Nanohybrid papers (NHP) of surface density of 2.6 $g/mm^2$ and 5.2 $g/mm^2$ were fabricated by vacuum filtration, as follows. A circular piece of grade 1 Whatman™ filter paper of size 70 mm in diameter was placed into a vacuum funnel and 40 ml of nanocellulose slurry was poured onto the filter paper circle. To obtain NHP with a surface density of 2.6 $g/mm^2$, a 0.025 wt/v % slurry was used. To obtain NHP with a surface density of 5.2 $g/mm^2$, a 0.05 wt/v % slurry was used. The filter paper and suspension were held under vacuum for 30 minutes until the paper was completely dry and a mat of nanocellulose fibers remained at the surface of the filter paper. FIGS. 29A-29D show SEM images of the various papers. Pure filter paper (FIG. 29A) had large pores. Pure nanopaper (FIG. 29D) had no pores. NHP paper (FIGS. 29B and 29C) had intermediate porosities.

FIGS. 29E-29H show confocal images of DOPC vesicles on the paper after 2 hours of growth in a 100 mM solution of sucrose. Pure filter paper had the smallest vesicle sizes and vesicles were present within the pores of the paper (FIG. 29E). Pure nanocellulose paper had the largest size of vesicles and vesicles were present only on the surface of the nanocellulose paper (FIG. 29H). The vesicles formed on NHP paper had intermediate size characteristics (FIGS. 29F and 29G).

Vesicles were harvested from these papers and the number of vesicles released, and their sizes, were quantified. FIG. 30A shows the number of vesicles released from the various papers by fluid shear. Pure filter paper released the lowest number of vesicles, indicating that many of the vesicles remain trapped in the paper. Nanocellulose paper released the highest number of vesicles, indicating that many of the vesicles were released into solution. The NHP papers had intermediate numbers of released vesicles that correlated with the surface concentration of NHP.

FIG. 30B shows that the sizes of the vesicles that are released are higher for the nanocellulose papers and the NHP papers compared to filter paper. Thus, this example shows that both the size of the vesicles formed, and the amount of vesicles released, can be controlled by changing the surface concentration of nanocellulose.

Example 27: Use of Soluble Polymers to Facilitate Vesicle Formation in High Salt Conditions The yield of vesicles formed on tracing paper is extremely low if the tracing paper is hydrated directly in solutions with >10 mM of monovalent salts (high salt solutions). One means of increasing yield, described elsewhere herein, is to begin vesicle growth under low salt conditions, then increase the salt concentration after vesicle growth has begun.

Another method for increasing vesicle yields under high-salt conditions, described in this example, is to treat the insoluble tracing paper substrate with soluble polymers. To this end, 420 μL of a 1 mg/mL solution of polymer was deposited onto a 9.5 mm diameter circle of tracing paper. The polymers tested were hyaluronic acid sodium salt from *Streptococcus equi* (1 mg/ml in water), carboxymethylcellulose (1 mg/ml in water), Ficoll (1 mg/ml in water) and dextran (1 mg/ml in water).

Figure 31:
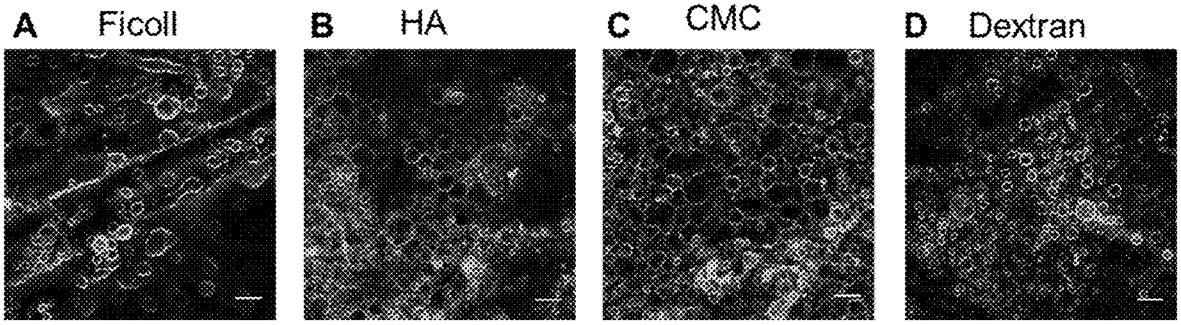

The papers were placed on a 40° C. hotplate for 1 hour to evaporate the water. After evaporation, 10 μL of a 1 mg/mL solution of DOPC:TopFluorPC (99:5:0.5 mol %) in chloroform was deposited on the polymer-coated papers. The papers were hydrated with 150 μL of a 1× solution of standard phosphate buffered saline (PBS) for 2 hours. The papers were then imaged with a confocal fluorescent microscope. FIG. 31 shows that the surfaces of papers coated with each of the four polymers were covered with a high density of vesicles, indicating that the soluble polymers dissolve and are encapsulated into the vesicles. This method thus provides a means to load the vesicles with therapeutic polymers such as hyaluronic acids, or lubricating polymers, such as carboxymethylcellulose.

REFERENCES

The following references, cited herein, are provided solely to assist in understanding the disclosure, and are not to be considered to be prior art.

(1) Walde, P.; Cosentino, K.; Engel, H.; Stano, P. Giant Vesicles: Preparations and Applications. *ChemBioChem.* 2010, 848-865.

(2) Dimova, R.; Aranda, S.; Bezlyepkina, N.; Nikolov, V.; Riske, K. A; Lipowsky, R. A practical guide to giant vesicles. Probing the membrane nanoregime via optical microscopy. *J. Phys. Condens. Matter* 2006, 18, S1151-S1176.

(3) Steer, D.; Leung, S. S. W.; Meiselman, H.; Topgaard, D.; Leal, C. Structure of lung-mimetic multilamellar bodies with lipid compositions relevant in pneumonia. *Langmuir* 2018, 34, 7561-7574.

(4) Dietrich, C.; Volovyk, Z. N.; Levi, M.; Thompson, N. L.; Jacobson, K. Partitioning of Thy-1, GM1, and cross-linked phospholipid analogs into lipid rafts reconstituted in supported model membrane monolayers. *Proc. Natl. Acad. Sci. U.S.A.* 2001, 98, 10642-10647.

(5) Veatch, S. L.; Keller, S. L. Separation of liquid phases in giant vesicles of ternary mixtures of phospholipids and cholesterol. *Biophys. J* 2003, 85, 3074-3083.

(6) Roodbeen, R.; Van Hest, J. C. M. Synthetic cells and organelles: Compartmentalization strategies. *BioEssays.* 2009, 1299-1308.

(7) Blain, J. C.; Szostak, J. W. Progress Toward Synthetic Cells. *Annu. Rev. Biochem.* 2014, 83, 615-640.

(8) Schmitt, C.; Lippert, A. H.; Bonakdar, N.; Sandoghdar, V.; Voll, L. M. Compartmentalization and Transport in Synthetic Vesicles. Front. Bioeng. *Biotechnol.* 2016, 4, 1-12.

(9) York-Duran, M. J.; Godoy-Gallardo, M.; Labay, C.; Urquhart, A. J.; Andresen, T. L.; Hosta-Rigau, L. Recent advances in compartmentalized synthetic architectures as drug carriers, cell mimics and artificial organelles. *Colloids Surfaces B Biointerfaces* 2017, 152, 199-213.

(10) Mulla, Y.; Aufderhorst-Roberts, A.; Koenderink, G. H. Shaping up synthetic cells. *Phys. Biol.* 2018, 15.

(11) Walde, P. Building artificial cells and protocell models: Experimental approaches with lipid vesicles. *BioEssays.* 2010, 296-303.

(12) Xu, C.; Hu, S.; Chen, X. Artificial cells: from basic science to applications. *Mater. Today* 2016, 19, 516-532.

(13) Reeves, J. P.; Dowben, R. M. Formation and properties of thin-walled phospholipid vesicles. *J Cell. Physiol.* 1969, 73, 49-60.

(14) Needham, D.; Evans, E. Structure and mechanical properties of giant lipid (DMPC) vesicle bilayers from 20 C below to 10 C above the liquid crystal-crystalline phase transition at 24 C. *Biochemistry* 1988, 27, 8261-8269.

(15) Bagatolli, L. A.; Parasassi, T.; Gratton, E. Giant phospholipid vesicles: Comparison among the whole lipid sample characteristics using different preparation methods—A two photon fluorescence microscopy study. *Chem. Phys. Lipids* 2000, 105, 135-147.

(16) Akashi, K.; Miyata, H.; Itoh, H.; Kinosita, K. Preparation of giant liposomes in physiological conditions and their characterization under an optical microscope. *Biophys. J.* 1996, 71, 3242-3250.

(17) Kubsch, B.; Robinson, T.; Steinkihler, J.; Dimova, R. Phase behavior of charged vesicles under symmetric and asymmetric solution conditions monitored with fluorescence Microscopy. *J Vis. Exp.* 2017, No. 128, 1-17.

(18) Angelova, M. I.; Dimitrov, D. S. Liposome electroformation. Faraday Discuss. *Chem. Soc.* 1986, 81, 303-311.

(19) Horger, K. S.; Estes, D. J.; Capone, R.; Mayer, M. Films of agarose enable rapid formation of giant liposomes in solutions of physiologic ionic strength. *J. Am. Chem. Soc.* 2009, 131, 1810-1819.

(20) Weinberger, A.; Tsai, F. C.; Koenderink, G. H.; Schmidt, T. F.; Itri, R.; Meier, W.; Schmatko, T.; Schroder, A.; Marques, C. Gel-assisted formation of giant unilamellar vesicles. *Biophys. J.* 2013, 105, 154-164.

(21) López Mora, N.; Hansen, J. S.; Gao, Y.; Ronald, A. A.; Kieltyka, R.; Malmstadt, N.; Kros, A. Preparation of size tunable giant vesicles from cross-linked dextran(ethylene glycol) hydrogels. *Chem. Commun.* 2014, 50, 1953-1955.

(22) Mora, N. L.; Gao, Y.; Gutierrez, M. G.; Peruzzi, J.; Bakker, I.; Peters, R. J. R. W.; Siewert, B.; Bonnet, S.; Kieltyka, R. E.; van Hest, J. C. M.; et al. Evaluation of dextran(ethylene glycol) hydrogel films for giant unilamellar lipid vesicle production and their application for the encapsulation of polymersomes. *Soft Matter* 2017, 13, 5580-5588.

(23) Movsesian, N.; Tittensor, M.; Dianat, G.; Gupta, M.; Malmstadt, N. Giant lipid vesicle formation using vapor-deposited charged porous polymers. *Langmuir* 2018, 34, 9025-9035.

(24) Peruzzi, J.; Gutierrez, M. G.; Mansfield, K.; Malmstadt, N. Dynamics of hydrogel-assisted giant unilamellar vesicle formation from unsaturated lipid systems. *Langmuir* 2016, 32, 12702-12709.

(25) Kresse, K. M.; Xu, M.; Pazzi, J.; Garcia-Ojeda, M.; Subramaniam, A. B.; Garcia-Ojeda, M.; Subramaniam, A. B. Novel application of cellulose paper as a platform for the macromolecular self-assembly of biomimetic giant liposomes. *ACS Appl. Mater. Interfaces* 2016, 8, 32102-32107.

(26) Li, A.; Pazzi, J.; Xu, M.; Subramaniam, A. B. Cellulose abetted assembly and temporally-decoupled loading of cargo into vesicles synthesized from functionally diverse lamellar phase forming amphiphiles. *Biomacromolecules* 2018, 19, 849-859.

(27) Dominak, L. M.; Keating, C. D.; Dominak, L. M. Polymer encapsulation within giant lipid vesicles. *Langmuir* 2007, 23, 7148-7154.

(28) Tsai, F. C.; Stuhrmann, B.; Koenderink, G. H. Encapsulation of active cytoskeletal protein networks in cell-sized liposomes. *Langmuir* 2011, 27, 10061-10071.

(29) Dominak, L. M.; Omiatek, D. M.; Gundermann, E. L.; Heien, M. L.; Keating, C. D. Polymeric crowding agents improve passive biomacromolecule encapsulation in lipid vesicles. *Langmuir* 2010, 26, 13195-13200.

(30) Estes, D. J.; Mayer, M. Giant liposomes in physiological buffer using electroformation in a flow chamber. *Biochim. Biophys. Acta—Biomembr.* 2005, 1712, 152-160.

(31) Peterlin, P.; Arrigler, V. Electroformation in a flow chamber with solution exchange as a means of preparation of flaccid giant vesicles. *Colloids Surfaces B Biointerfaces* 2008, 64, 77-87.

(32) Nieth, A.; Verseux, C.; Bamert, S.; Suss, R.; Romer, W. A first step toward liposome-mediated intracellular bacteriophage therapy. *Expert Opin. Drug Deliv.* 2015, 5247, 1-14.

(33) Singla, S.; Harjai, K.; Raza, K.; Wadhwa, S.; Katare, O. P.; Chhibber, S. Phospholipid vesicles encapsulated bacteriophage: A novel approach to enhance phage biodistribution. *J. Virol.* Methods 2016, 236, 68-76.

(34) Buddingh', B. C.; Van Hest, J. C. M. Artificial Cells: Synthetic compartments with life-like functionality and adaptivity. *Acc. Chem. Res.* 2017, 50, 769-777.

(35) Paleos, C. M.; Tsiourvas, D.; Sideratou, Z.; Pantos, A. Formation of artificial multicompartment vesosome and dendrosome as prospected drug and gene delivery carriers. *J. Control. Release* 2013, 170, 141-152.

(36) Stachowiak, J. C.; Richmond, D. L.; Li, T. H.; Brochard-Wyart, F.; Fletcher, D. A. Inkjet formation of unilamellar lipid vesicles for cell-like encapsulation. *Lab Chip* 2009, 9, 2003-2009.

(37) Szoka, F.; Papahadjopoulos, D. Comparative properties and methods of preparation of lipid vesicles (liposomes). *Ann. Rev Biophys. Bioeng* 1980, 9, 467-508.

(38) Dominak, L. M.; Keating, C. D. Macromolecular Crowding Improves Polymer Encapsulation within Giant Lipid Vesicles. *Langmuir* 2008, 2, 13565-13571.

(39) *Cotton: Science and Technology,* 1st ed.; Gordon, S., Hsieh, Y. L., Eds.; Woodhead Publishing: Cambridge, 2007.

(40) Li, Y.-Y.; Wang, B.; Ma, M.-G.; Wang, B. Review of recent development on preparation, properties, and applications of cellulose-based functional materials. *Int. J Polym. Sci.* 2018, 2018, 1-18.

(41) Alava, M.; Niskanen, K. The physics of paper. *Reports Prog. Phys.* 2006, 69, 669-723.

(42) Dullien, F. *Porous Media: Fluid Transport and Pore Structure,* 2nd ed.; Brenner, H., Ed.; Academic Press: San Diego, 1991.

(43) Bogaty, H.; T., C. F. Measurement of rate of flow of water through filter paper. *J. Res. Natl. Bur. Stand.* (1934). 1944, 33, 353-362.

(44) Rodriguez, N.; Pincet, F.; Cribier, S. Giant vesicles formed by gentle hydration and electroformation: A comparison by fluorescence microscopy. *Colloids Surfaces B Biointerfaces* 2005, 42, 125-130.

(45) Pereno, V.; Carugo, D.; Bau, L.; Sezgin, E.; Bernardino De La Sema, J.; Eggeling, C.; Stride, E. Electroformation of giant unilamellar vesicles on stainless steel electrodes. *ACS Omega* 2017, 2, 994-1002.

(46) Zupanc, J.; Drasler, B.; Boljte, S.; Kralj-Iglic, V.; Iglic, A.; Erdogmus, D.; Drobne, D. Lipid vesicle shape analysis from populations using light video microscopy and computer vision. *PLoS One* 2014, 9, 1-14.

(47) Dimitrov, D. S.; Angelova, M. I. Lipid swelling and liposome formation on solid surfaces in external electric fields. 1987, 56, 48-56.

(48) Greene, A. C.; Henderson, I. M.; Gomez, A.; Paxton, W. F.; VanDelinder, V.; Bachand, G. D. The role of membrane fluidization in the gel-assisted formation of giant polymersomes. *PLoS One* 2016, 11, e0158729.

(49) Faysal, K. M. R.; Park, J. S.; Nguyen, J.; Garcia, L.; Subramaniam, A. B. Lipid bilayers are long-lived on solvent cleaned plasma-oxidized poly(dimethyl) siloxane (ox-PDMS). *PLoS One* 2017, 12, 1-16.

(50) Lu, C.; Lu, Y. H.; Shen, Y. G.; Mai, Y. W. Log-normal nanograin-size distributions in nanostructured composites. *Philos. Mag. Lett.* 2008, 88, 829-836.

(51) Teran, A. V.; Bill, A.; Bergmann, R. B. Time-evolution of grain size distributions in random nucleation and growth crystallization processes. *Phys. Rev. B—Condens. Matter Mater. Phys.* 2010, 81, 1-19.

(52) Kostoglou, M.; Lioumbas, J.; Karapantsios, T. A population balance treatment of bubble size evolution in free draining foams. *Colloids Surfaces A Physicochem. Eng. Asp.* 2015, 473, 75-84.

(53) Tenchov, B. G.; Yanev, T. K. Weibull distribution of particle sizes obtained by uniform random fragmentation. *J Colloid Interface Sci.* 1986, 111, 1-7.

(54) Hosoda, K.; Matsuura, T.; Suzuki, H.; Yomo, T. Origin of lognormal-like distributions with a common width in a growth and division process. *Phys. Rev. E—Stat. Nonlinear, Soft Matter Phys.* 2011, 83, 1-5.

(55) Best, A. C. The size distribution of raindrops. *Quarterly Journal of the Royal Meteorological Society.* 1950, pp 16-36.

(56) Letters, E. Truncated power laws: a tool for understanding aggregation patterns in animals? 2000, 90-94.

(57) Bergmann, R. B.; Bill, A. On the origin of logarithmic-normal distributions: An analytical derivation, and its application to nucleation and growth processes. *J Cryst. Growth* 2008, 310, 3135-3138.

(58) Limpert, E.; Stahel, W. A.; Abbt, M. Log-normal Distributions across the Sciences: Keys and Clues. 2001, 51, 341-352.

What is claimed is:

1. A method for making a vesicle-coated substrate, the method comprising:

(a i) dispersing an amphiphilic molecule in a solvent;

(a ii) coating a paper substrate with a polymer selected from one of carboxymethylcellulose, dextran and polypeptides;

(b) contacting the dispersed amphiphilic molecule of (a i) with the fibrous-substrate;

(c) removing the solvent; and (d) incubating the amphiphile-coated substrate in a growth buffer solution having a temperature that is less than the transition temperature of the amphiphilic molecule, wherein the ionic strength of the growth buffer is less than 10 mM monovalent salt and increased during the incubation to higher than 10 mM monovalent salt, and wherein vesiculation is induced by increasing the temperature of the growth buffer to a temperature greater than the transition temperature of the amphiphile, wherein vesicles encapsulates hydrophilic molecules within their lumen, and wherein the encapsulated hydrophilic molecules are protected until they are released from the vesicles.

2. The method of claim 1, wherein the amphiphilic molecule is selected from the group consisting of a phospholipid, a sphingolipid, a fatty acid, a quaternary ammonium surfactant, a ceramide, a fatty alcohol, an amphiphilic polymer, a diblock polymer or a triblock polymer.

3. The method of claim 1, further comprising, prior to step (d), introducing a compound into the growth buffer solution.

4. The method of claim 1, further comprising, in step (a), dispersing a second molecule in the solvent.

5. The method of claim 4, wherein the second molecule is hydrophilic and the solvent is water.

* * * * *